(12) United States Patent
Ulrich et al.

(10) Patent No.: US 6,956,963 B2
(45) Date of Patent: Oct. 18, 2005

(54) IMAGING FOR A MACHINE-VISION SYSTEM

(75) Inventors: Franz W. Ulrich, Minneapolis, MN (US); Leonard H. Bieman, Waterford, MI (US)

(73) Assignee: Ismeca Europe Semiconductor SA, La Chaux-de-Fonds (CH)

( * ) Notice: Subject to any disclaimer, the term of this patent is extended or adjusted under 35 U.S.C. 154(b) by 589 days.

(21) Appl. No.: 09/757,834

(22) Filed: Jan. 8, 2001

(65) Prior Publication Data

US 2003/0039388 A1 Feb. 27, 2003

Related U.S. Application Data

(63) Continuation of application No. PCT/US99/15411, filed on Jul. 8, 1999.
(60) Provisional application No. 60/092,089, filed on Jul. 8, 1998.

(51) Int. Cl.[7] .................................................. G06K 9/00
(52) U.S. Cl. ...................................... 382/154; 382/145
(58) Field of Search ................................ 382/152, 154, 382/145, 141, 149, 147; 356/237.2; 702/35; 348/36, 87, 125, 126

(56) References Cited

U.S. PATENT DOCUMENTS

| | | | |
|---|---|---|---|
| 3,069,654 A | 12/1962 | Hough | 340/146.3 |
| 4,064,888 A | 12/1977 | Diebel | 134/182 |
| 4,212,073 A | 7/1980 | Balasubramanian | 364/562 |
| 4,370,300 A | 1/1983 | Mori et al. | 422/108 |
| 4,494,874 A | 1/1985 | DiMatteo et al. | 356/376 |
| 4,559,902 A | 12/1985 | Mason et al. | 119/2 |
| 4,565,314 A | 1/1986 | Scholz | 228/180.2 |
| 4,639,139 A | 1/1987 | Wyant et al. | 356/359 |
| 4,641,972 A | 2/1987 | Halioua et al. | 356/376 |

(Continued)

FOREIGN PATENT DOCUMENTS

| | | | |
|---|---|---|---|
| EP | 0638801 | 2/1995 | G01N/21/88 |
| WO | 98/02716 | 1/1998 | G01B/11/03 |

OTHER PUBLICATIONS

"About Boulder Nonlinear Systems", *Boulder Nonlinear Systems, Inc.*, http://www.bnonlinear.com/AboutBNS.htm, (2000),pp. 1–4.

(Continued)

*Primary Examiner*—John B Strege
(74) *Attorney, Agent, or Firm*—Lemaire Patent Law Firm, P.L.L.C.; Charles A. Lemaire

(57) ABSTRACT

Manufacturing lines include inspection systems for monitoring the quality of parts produced. Manufacturing lines for making semiconductor devices generally inspect each fabricated part. The information obtained is used to fix manufacturing problems in the semiconductor fab plant. A machine-vision system for inspecting devices includes a light source for propagating light to the device and an image detector that receives light from the device. Also included is a light sensor assembly for receiving a portion of the light from the light source. The light sensor assembly produces an output signal responsive to the intensity of the light received at the light sensor assembly. A controller controls the amount of light received by the image detector to a desired intensity range in response to the output from the light sensor. The image detector may include an array of imaging pixels. The imaging system may also include a memory device which stores correction values for at least one of the pixels in the array of imaging pixels. To minimize or control thermal drift of signals output from an array of imaging pixels, the machine-vision system may also include a cooling element attached to the imaging device. The light source for propagating light to the device may be strobed. The image detector that receives light from the device remains in a fixed position with respect to the strobed light source. A translation element moves the strobed light source and image detector with respect to the device. The strobed light may be alternated between a first and second level.

33 Claims, 38 Drawing Sheets

U.S. PATENT DOCUMENTS

| | | | |
|---|---|---|---|
| 4,705,395 A | 11/1987 | Hageniers | 356/1 |
| 4,729,536 A | 3/1988 | Scala | 248/429 |
| 4,742,552 A | 5/1988 | Andrews | 382/41 |
| 4,869,636 A | 9/1989 | Reid et al. | 414/331 |
| 4,907,701 A | 3/1990 | Kobayashi et al. | 209/576 |
| 4,965,665 A | 10/1990 | Amir | 358/101 |
| 4,967,066 A | 10/1990 | Beraldin et al. | 250/205 |
| 4,967,284 A | 10/1990 | Yoshida et al. | 358/300 |
| 4,991,968 A | 2/1991 | Yonescu et al. | 356/376 |
| 5,039,868 A * | 8/1991 | Kobayashi et al. | 250/559.08 |
| 5,060,065 A | 10/1991 | Wasserman | 358/106 |
| 5,085,502 A | 2/1992 | Womack et al. | 356/376 |
| 5,251,156 A | 10/1993 | Heier et al. | 364/559 |
| 5,285,397 A | 2/1994 | Heier et al. | 364/559 |
| 5,355,221 A | 10/1994 | Cohen et al. | 356/359 |
| 5,379,107 A | 1/1995 | Hanssen et al. | 356/376 |
| 5,398,113 A | 3/1995 | de Groot | 356/360 |
| 5,426,302 A | 6/1995 | Marchman et al. | 250/306 |
| 5,460,758 A * | 10/1995 | Langer et al. | 264/401 |
| 5,465,152 A | 11/1995 | Bilodeau et al. | 356/371 |
| 5,469,249 A * | 11/1995 | Magyar et al. | 356/4.07 |
| 5,546,189 A | 8/1996 | Svetkoff et al. | 356/376 |
| 5,561,525 A | 10/1996 | Toyonaga et al. | 356/360 |
| 5,574,668 A | 11/1996 | Beaty | 364/558 |
| 5,574,801 A | 11/1996 | Collet-Beillon | 382/150 |
| 5,621,218 A | 4/1997 | Tanaka | 250/559.34 |
| 5,621,530 A | 4/1997 | Marrable, Jr. | 356/394 |
| 5,636,025 A | 6/1997 | Bieman et al. | 356/374 |
| 5,646,733 A | 7/1997 | Bieman | 356/376 |
| 5,680,215 A | 10/1997 | Huber et al. | 356/371 |
| 5,691,810 A | 11/1997 | Bilodeau et al. | 356/237.1 |
| 5,719,952 A | 2/1998 | Rooks | 382/150 |
| 5,740,280 A | 4/1998 | Leonardi et al. | 382/240 |
| 5,745,176 A | 4/1998 | Lebens | 348/370 |
| 5,753,903 A | 5/1998 | Mahaney | 250/205 |
| 5,859,698 A | 1/1999 | Chau et al. | 356/237 |
| 5,909,285 A | 6/1999 | Beaty et al. | 356/394 |
| 5,943,125 A | 8/1999 | King et al. | 356/237.1 |
| 6,011,620 A | 1/2000 | Sites et al. | 356/239.1 |
| RE36,560 E | 2/2000 | Svetkoff et al. | 356/376 |
| 6,022,124 A | 2/2000 | Bourn et al. | 362/247 |
| 6,025,905 A | 2/2000 | Sussman | 356/3.01 |
| 6,069,701 A | 5/2000 | Hashimoto et al. | 356/376 |
| 6,072,898 A | 6/2000 | Beaty et al. | 382/146 |
| 6,075,216 A | 6/2000 | Nakamura et al. | 209/573 |
| 6,119,927 A | 9/2000 | Ramos et al. | 228/254 |
| 6,139,243 A | 10/2000 | Jackson et al. | 414/405 |
| 6,173,070 B1 | 1/2001 | Michael et al. | 382/145 |
| 6,177,682 B1 | 1/2001 | Barkulovic et al. | 250/559.44 |
| 6,181,472 B1 | 1/2001 | Liu | 359/618 |
| 6,222,187 B1 | 4/2001 | Shivanandan | 250/330 |
| 6,249,347 B1 | 6/2001 | Svetkoff et al. | 356/376 |
| 6,260,000 B1 | 7/2001 | Karasaki et al. | 702/155 |
| 6,282,462 B1 | 8/2001 | Hopkins | 700/259 |
| 6,285,787 B1 * | 9/2001 | Kawachi et al. | 382/209 |
| 6,320,680 B1 * | 11/2001 | Rhoads | 358/497 |
| 6,341,016 B1 | 1/2002 | Malione | 356/603 |

OTHER PUBLICATIONS

Bains, S., "Technology—Device steers white light through wide angles", *EE Times*, (1999), 2 pages.

Ballard, D.H., "Generalizing the Hough Transform to Detect Arbitrary Shapes", *Pattern Recognition*, 13(2), Pergamon Press, pp. 183–194, (1981).

Davies, E.R., *Machine Vision: Theory, Algorithms, Practicalities, 2nd Edition*, Academic Press, San Diego, pp. 195–210, (1997).

Yang, H.S., et al., "Determination of the Identity, Postiton and Orientation of the Topmost Object in a Pile: Some Further Experiments", *IEEE International Conference on Robotics and Automation*, 1, San Francisco. CA, 293–298, (1986).

* cited by examiner

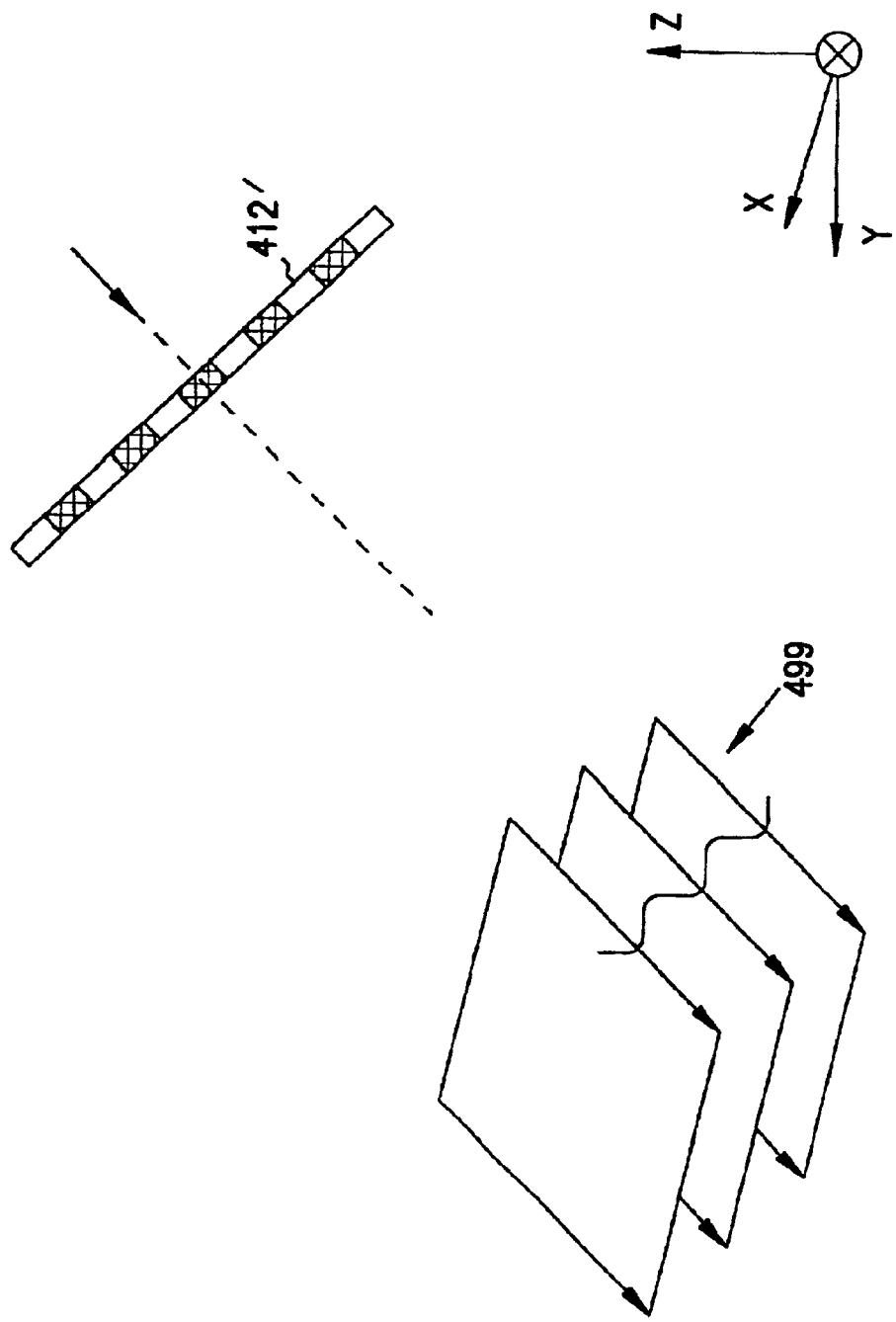

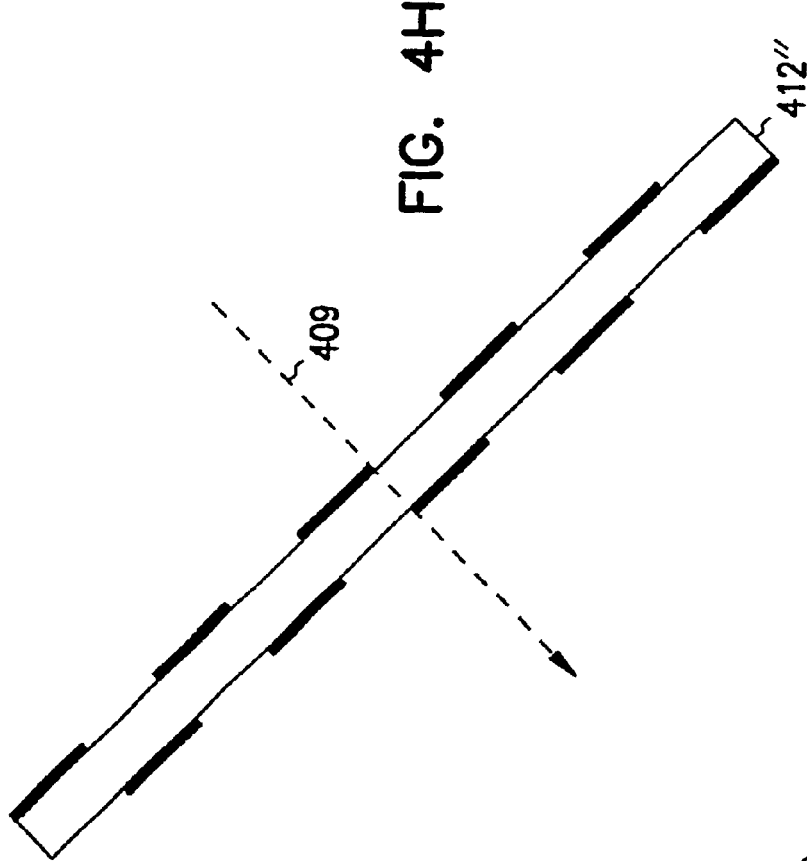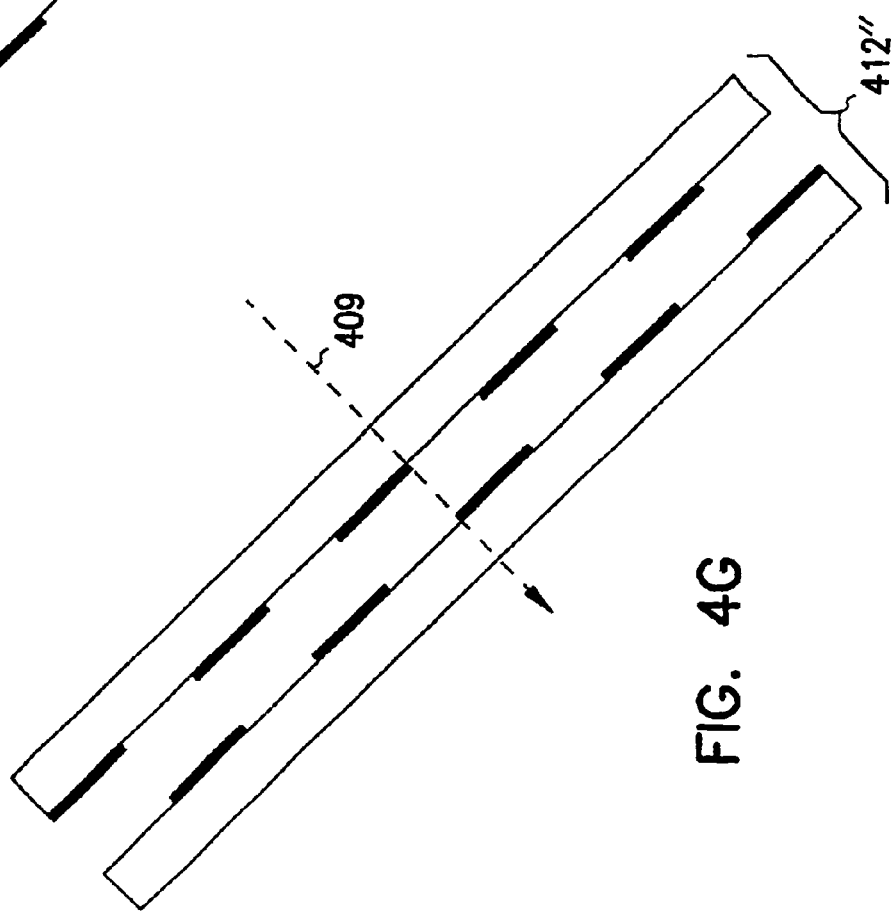

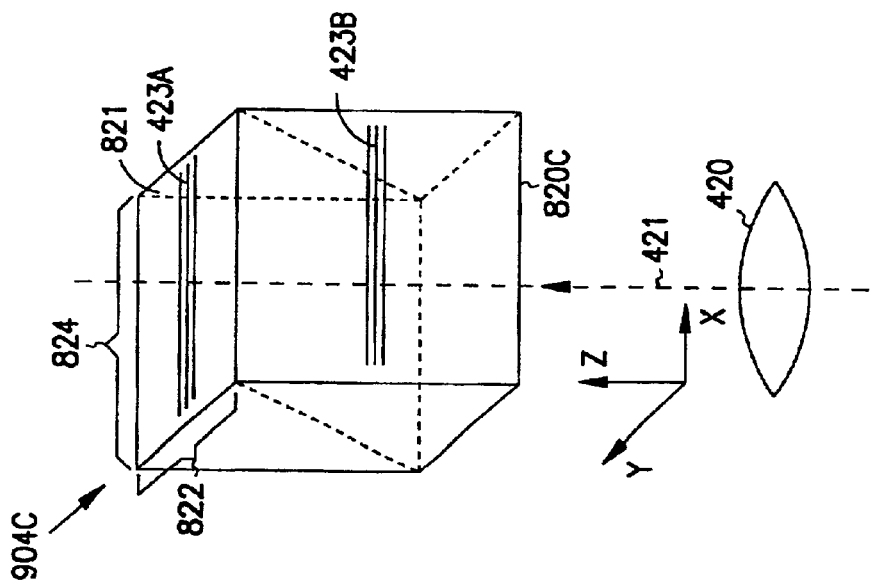
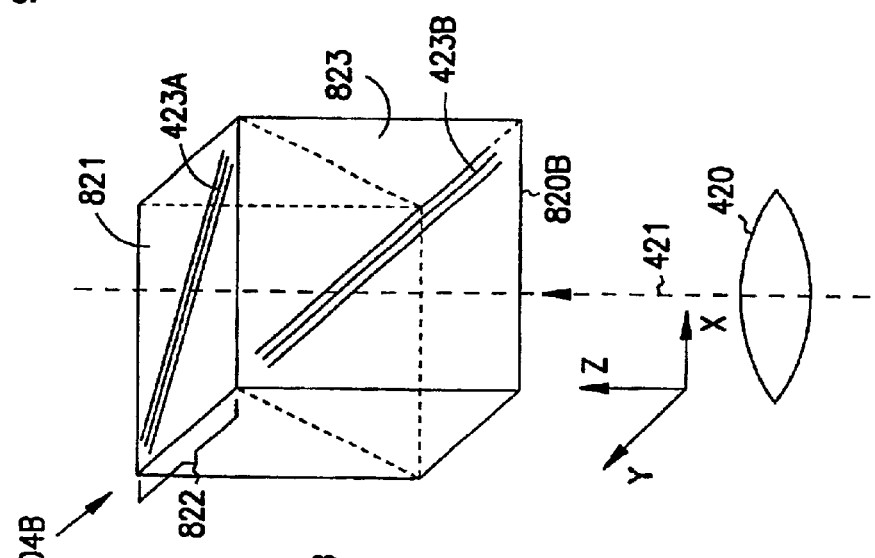
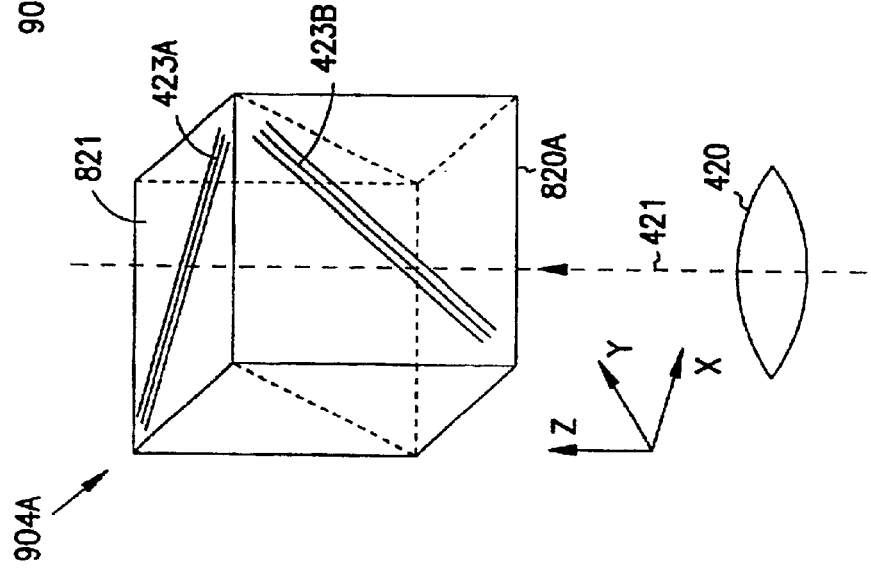

| PIXEL # | CORRECTION VALUE (CONDITION A LIGHT SOURCE A) | CORRECTION VALUE (CONDITION B LIGHT SOURCE A) | CORRECTION VALUE (CONDITION A LIGHT SOURCE B) | |
|---|---|---|---|---|
| • | • | • | • | • |
| • | • | • | • | • |
| • | • | • | • | • |
| • | • | • | • | • |
| X | Y | Z | W | Q |

TABLE LOOKUP 1410

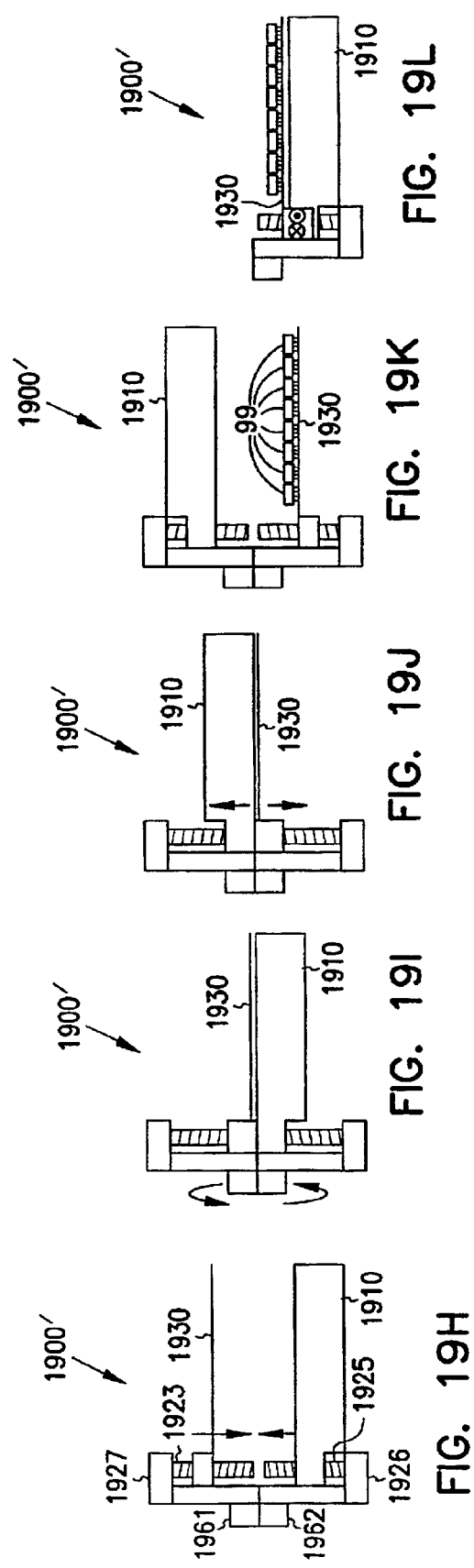

IMAGING FOR A MACHINE-VISION SYSTEM

CROSS REFERENCE TO RELATED APPLICATION

This application is a continuation under 35 U.S.C. 111(a) of International Application No. PCT/US99/15411, filed Jul. 8, 1999, which claims priority under 119(e) from U.S. Provisional Application Ser. No. 60/092.089, filed Jul. 8, 1998, which applications are incorporated herein by reference.

FIELD OF THE INVENTION

This invention relates to the field of machine vision, and more specifically to a method and apparatus of obtaining three-dimensional inspection data for electronic parts in a manufacturing environment. The invention relates to circuitry used to control the illumination of the lamps and preventing bias and gain drift due to variances in temperature.

BACKGROUND OF THE INVENTION

There is a widespread need for inspection data for electronic parts in a manufacturing environment. One common inspection method uses a video camera to acquire two-dimensional images of a device-under-test.

Height distribution of a surface can be obtained by projecting a light stripe pattern onto the surface and then reimaging the light pattern that appears on the surface. One technique for extracting this information based on taking multiple images (3 or more) of the light pattern that appears on the surface while shifting the position (phase) of the projected light stripe pattern is referred to as phase shifting interferometry, as disclosed in U.S. Pat. Nos. 4,641,972 and 4,212,073.

The multiple images are usually taken using a CCD (charge-coupled device) video camera with the images being digitized and transferred to a computer where phase-shift analysis, based on images being used as "buckets," converts the information to a contour map (i.e., a three-dimensional representation) of the surface.

The techniques used to obtain the multiple images are based on methods that keep the camera and viewed surface stationary with respect to each other while moving the projected pattern.

One technique for capturing just one bucket image using a line scan camera is described in U.S. Pat. No. 4,965,665.

U.S. Pat. Nos. 5,398,113 and 5,355,221 disclose white-light interferometry systems which profile surfaces of objects.

In U.S. Pat. No. 5,636,025, an optical measuring system is disclosed which includes a light source, gratings, lenses, and camera. A mechanical translation device moves one of the gratings in a plane parallel to a reference surface to effect a phase shift of a projected image of the grating on the contoured surface to be measured. A second mechanical translation device moves one of the lenses to effect a change in the contour interval. A first phase of the points on the contoured surface is taken, via a four-bucket algorithm, at a first contour interval. A second phase of the points is taken at a second contour interval. A control system, including a computer, determines a coarse measurement using the difference between the first and second phases. The control system further determines a fine measurement using either the first or second phase. The displacement or distance, relative to the reference plane, of each point is determined, via the control system, using the fine and coarse measurements.

Current vision inspection systems have many problems. Among the problems are that the intensity of the light received at a light receiver may vary. When the intensity of the light varies at the receiver, it is very difficult to correlate signals that are generated by the receiver. Another problem is that the light receiver may vary in temperature. Many of the receivers use a charge coupled device (also called a CCD). A charged coupled device or CCD is a high speed, high density computer storage medium in which the transfer of stored charges provides the information. The stored charges produce signals which provide image information received. CCDs tend to heat up as they operate. As the CCDs heat, the signals produced shift or vary. Typically, there are currents associated with dark areas and currents associated with light areas. Part of correlating the data obtained includes a subtraction of the current associated with a dark area. This is used to find the absolute value of the current associated with a light area. Dark currents approximately double with every 7° C. rise in temperature. When the currents associated with dark areas get too large, the current shows up as noise. The elimination of noise is another problem which complicates processing of the image. Within a CCD there are many individual sources of light. These light sources, typically LEDs, may also vary on a pixel-by-pixel or source-by-source basis since the gain and bias may differ as a result of manufacturing variances. This too adds to the difficulty in correlating data obtained from one sensor or another sensor since light of different intensities is being produced by the source.

Another problem is that infrared light may also adversely effect the sensor. Infrared light can vary the signal strength read by the sensor. Yet another problem associated with machine vision systems is that an image is captured using a substantially constant source of light. In order to get an adequate image, the image must be captured over a relatively long time frame. The result is the same as occurs when there is low levels of light and the object to photograph is moving fast. The image is blurred or smeared.

To overcome the problems stated above as well as other problems, there is a need for an improved machine-vision system and more specifically there is a need for a circuit or circuits which can be used to control lamp brightness or the aperture associated with a CCD. There is also a need for temperature control of the sensor to prevent or lessen the effects of thermal drift on the bias or gain of the signal output from the sensor. In addition, there is a need for a system which allows for correction of a CCD or other light sources on a pixel-by-pixel basis so that manufacturing tolerances are accounted for. There is also need for a device that controls the amount of infrared light that is received at a sensor so as control the bias or gain of the signal output from the sensor. In addition, there is a need for a device which facilitates automated high-speed three-dimensional inspection of objects.

SUMMARY OF THE INVENTION

A machine-vision system for inspecting a device includes a light source for propagating light to the device and an image detector that receives light from the device. Also included is a light sensor assembly for receiving a portion of the light from the light source. The light sensor assembly produces an output signal responsive to the intensity of the light received at the light sensor assembly. A controller controls the amount of light received by the image detector to a desired intensity range in response to the output from the light sensor. The light sensor assembly includes a beam splitter positioned between the light source and the device, and a light sensor positioned to receive light from the beam splitter. The beam splitter filters infrared light from the light source. The controller controls the light intensity by controlling the power supply for the light source or by controlling the amount of light received by the image detector as the image detector acquires an image. The image detector can be an array of imaging pixels. The controller controls the amount of light received by the image detector by controlling the amount time the array of imaging pixels receives light to acquire an image. The imaging system may also include a memory device which stores correction values for at least one of the pixels in said array of imaging pixels. The correction value can be controlled by the controller.

The machine-vision system for inspecting a device may also include a cooling element attached to the imaging device. The cooling element removes heat produced by the image detector to keep the image detector within a selected temperature range. The cooling element may, be a thermoelectric semiconductor. The thermoelectric semiconductor unit may include a temperature sensor for sensing the temperature of the array of semiconductor imaging pixels. The cool portion of the thermoelectric semiconductor is attached to the array of semiconductor imaging pixels and forms a thermally conductive path between the array of semiconductor imaging pixels and the thermoelectric semiconductor unit. A controller controls the amount of power input to the thermoelectric semiconductor to keep the image detector within a selected temperature range.

The machine-vision system for inspecting a device may also include a strobed light source for propagating light to the device. The image detector that receives light from the device remains in a fixed position with respect to the strobed light source. A translation element moves the strobed light source and image detector with respect to the device. The machine-vision system may include a ring light source. The machine-vision system may also include a strobed light controller which controls the strobed light source to produce light having a first level and to produce light having a second level. The strobed light controller controls the strobed light source to produce light having a first level alternated with light having a second level. The strobed light controller may control the strobed light source and the strobed ring light source. The image detector is comprised of a first line of pixels and a second line of pixels.

A method for acquiring physical information associated with of a device using a machine-vision station having a light source and having an image detector includes the steps of projecting light from the light source to the device, receiving light reflected from the device into the image detector, and controlling the amount of light received at the image detector to a value within a desired range. The step of controlling the amount of light received at the image detector includes the steps of sensing the light projected from the light source, and controlling the amount of power input to the light source in response to the value produced by said sensing step. Another way of controlling the amount of light received at the image detector includes the steps of sensing the light projected from the light source, and controlling the length of time the image detector is exposed to reflected light in response to the value produced by said sensing step. Another way to control the amount of light received at the image detector further comprises the steps of sensing the reflected light from the device, and controlling the amount of power input to the light source in response to the value produced by the sensing step. A variable aperture may also be used to control the intensity of light received at the sensor. Heat can also be removed from the image detector to keep the image detector within a selected temperature range. This prevents thermal drift of the signals output from the image detector.

Another method for acquiring physical information associated with of a device uses a machine-vision station having a light source and having an image detector. The method includes the steps of fixing the relationship between the light source and the image detector, moving the light source and the image detector with respect to the device, projecting strobed light from the light source to the device, and receiving light reflected from the device into an image detector. The step of projecting strobed light from the light source to the device further comprises the steps of producing a first level of strobed light from the light source, and producing a second level of strobed light from the light source. The strobed light may be produced by a ring light. The strobed light may be alternated between a first and second level. The inspection systems described above may be used in any manufacturing system or environment. Once such manufacturing system or environment is a semiconductor part fabrication unit which fabricates part or a whole portion of a semiconductor device.

Advantageously, this invention solves or lessens many of the problems associated with current vision inspection systems. A feedback loop is used to control the intensity of the light received at a light receiver. This reduces the variability of the light intensity received at the light receiver. This eases the task of correlating signals generated by the receiver. Within a CCD the individual sources of light may be controlled to control the gain and bias resulting from manufacturing variances. This also eases the task of correlating data obtained from one sensor or another sensor since light of different intensities is not being produced by the source. A thermoelectric device is added to the light receiver to moderate temperature changes. This reduces signal shift or variation. An infrared filter in the path before the sensor also aids in keeping the signal from the sensor correlatable since the effects of IR light are reduced. In addition, the source of light is strobed to eliminate blurred or smeared images.

BRIEF DESCRIPTION OF THE DRAWINGS

FIG. 4F shows a projection pattern element 412' of another embodiment, and represents a square-wave pattern near the element.

FIG. 4G shows a projection pattern element 412" of another embodiment, and represents a square-wave pattern near the element.

FIG. 4H shows a projection pattern element 412" of another embodiment, and represents a square-wave pattern near the element.

FIG. 9A shows a sensor 904A having a beamsplitter 820A.

FIG. 9B shows a sensor 904B having a beamsplitter 820B.

FIG. 9C shows a sensor 904C having a beamsplitter 820C.

FIG. 14B is a table lookup which is housed within memory and used to apply correction values to the values associated with the pixels of a trilinear array.

FIGS. 19H, 19I, 19J, 19K, 19L are sideviews of the tray inverter mechanism of FIGS. 19C–19G, respectively.

DETAILED DESCRIPTION OF THE PREFERRED EMBODIMENT

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Machine-vision and optical-feature-recognition techniques can be used to distinguish parts that deviate from a predetermined intended aspect of an ideal device. In this description, a "device" is meant to be any device of manufacture or object, for example an integrated circuit package, electronic part, semiconductor, molded plastic part, aluminum wheel, gemstone or even an egg or strawberry, which can be inspected. Typically, according to the present invention, a manufacturing operation will use two-dimensional and three dimensional information acquired from inspection of the device to distinguish "good" parts from "bad" parts, and can discard the bad parts and insert previously inspected good parts in their place. The devices under test are placed into pocketed trays or into cartons for ease of handling and transport, and inspection will take place of the devices while the devices are in the pocketed trays, according to the present invention.

U.S. Pat. No. 5,646,733 to Bieman describes a method and system that include an optical head which is moved relative to an object at a machine-vision station. A projected pattern of light (e.g., a pattern of stripes or lines) is scanned across the surface of an object to be inspected to generate an imagable light signal to acquire three- dimensional information associated with the object. The optical head includes at least one pattern projector which projects a pattern of lines and an imaging subsystem which includes a trilinear-array camera as a detector. The camera and the at least one pattern projector are maintained in fixed relation to each other. The trilinear-array camera includes three linear detector elements, each having for example about 1000 to 4000 pixels, which extend in a direction parallel with the pattern of lines. The geometry of the optical head is arranged in such a way that each linear detector element picks up a different phase in the line pattern. As the optical head is scanned across the surface of interest, the detector elements are continuously read out. Depth at each point on the surface is calculated from the intensity readings obtained from each of the detector elements that correspond to the same point on the surface. In this way, the phases of the pattern are calculated from the three intensity readings obtained for each point.

System Overview

Figure 1:
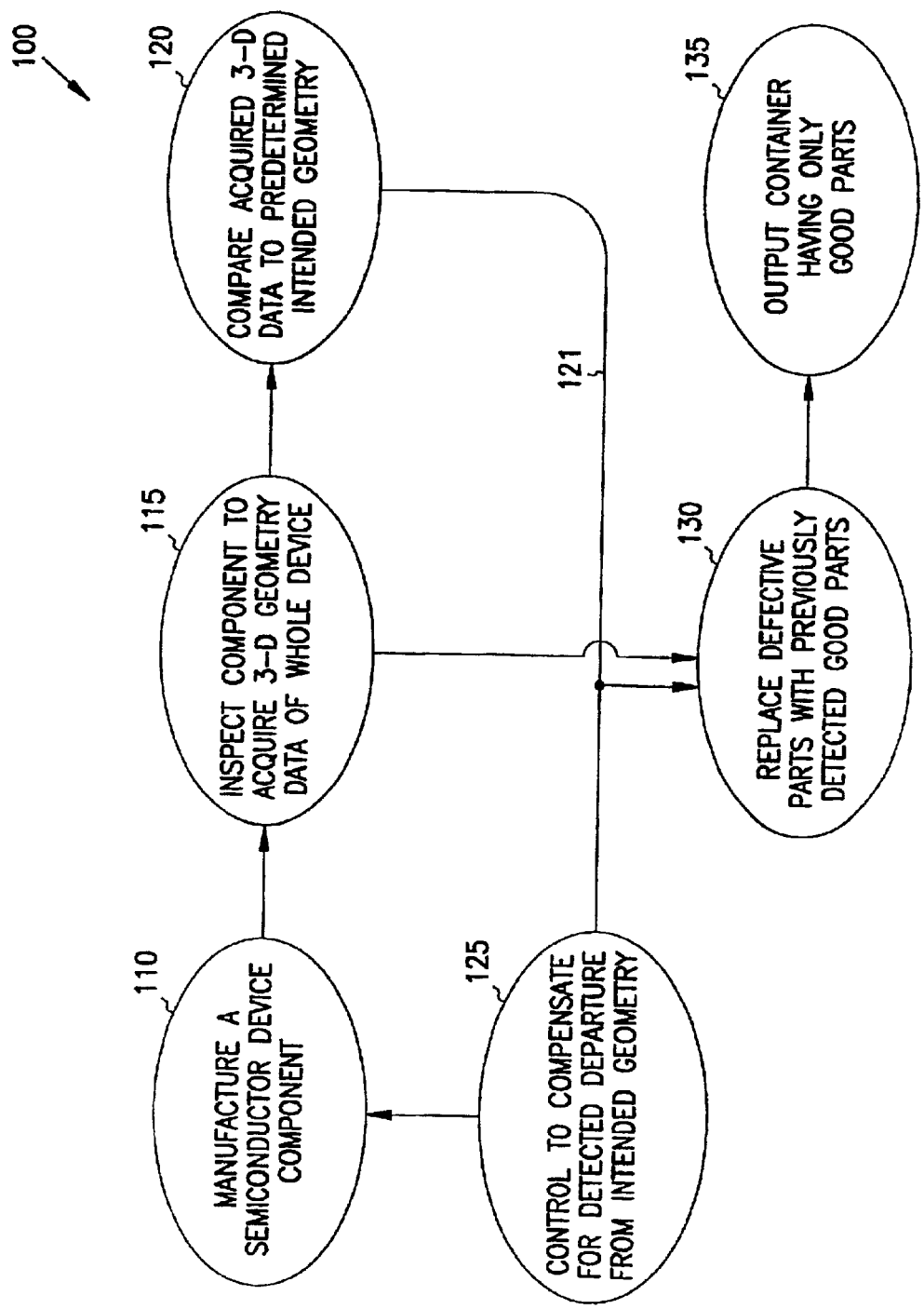
FIG. 1 shows an embodiment of the present invention, a system 100 for the manufacture and inspection of devices.

FIG. 1 is a schematic representation of a high-speed automated inspection system 100 and its associated method, according to one embodiment of the present invention. At station 110, a manufacturing process or step produces or modifies a device. In one embodiment, the device 99, along with a plurality of other devices are placed in a pocketed tray. In other embodiments, other containers are used. In still other embodiments, devices to be inspected are attached to continuous plastic strips that are, e.g., unwound from a reel in order to be inspected, inspected in line as the devices move across the camera, and then rewound onto a reel after inspection. In yet other embodiments, devices are moved on a conveyor-belt line under the scanning camera, with no tray, strip, or other container. Thus, where ever the inspection of devices in trays is discussed herein, it is to be understood that other embodiments that inspect devices using other containers, or devices attached to strips, or even devices without any container, are contemplated as alternative embodiments.

Figure 4A:
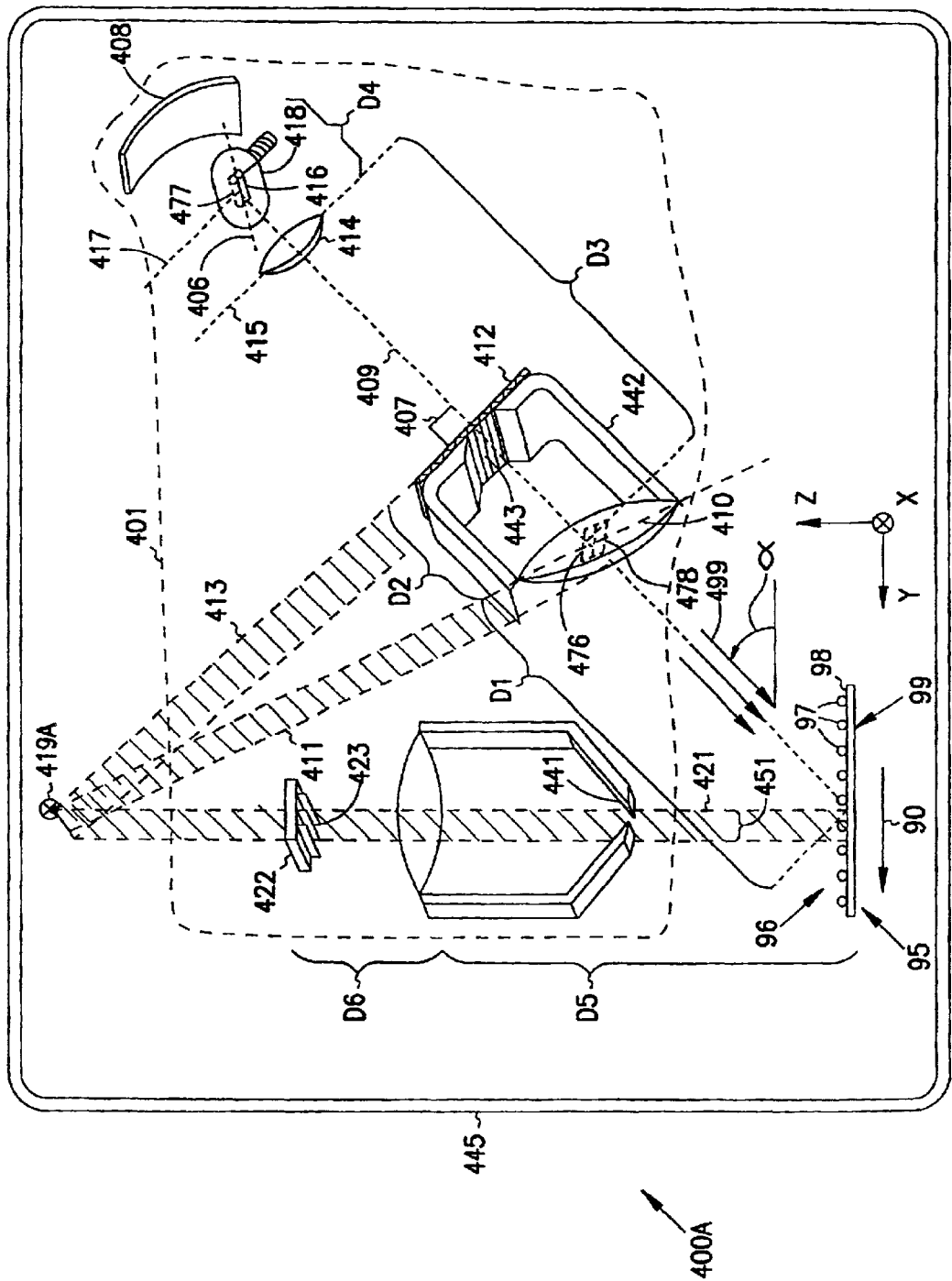
FIG. 4A shows one embodiment of a machine-vision head 401 for inspecting a device 99.

At station 115, the tray of devices is scanned to acquire two-dimensional (2D) and/or three-dimensional (3D) data representing the geometry of every device in the tray. In one embodiment, a CCD camera having digital output is used in station 15. In one such embodiment, the digital output of the CCD represents a 2D image of device 99. In another embodiment, a 3D scanning Moire interferometry sensor such as sensor 400A of FIG. 4A is used to acquire 3D dimensions (i.e., the X, Y, and Z dimensions of various features of device 99), and/or intensity measurements (i.e., the brightness, color, or reflectivity of various features of device 99). The acquired 2D and/or 3D and/or intensity data is processed at station 120, and compared to data of a predetermined intended geometry. In one embodiment, this comparison distinguishes good devices from bad devices, and a signal 121 is output. In one embodiment, signal 121 is used at station 125 as a control to compensate for the detected departure from the intended geometry, thus providing feedback into the manufacturing step at station 110, in order to improve quality and yield of the manufacturing system. In another embodiment, signal 121 is used at station 130 to control the replacement of defective or substandard parts with good parts from a previously inspected tray of parts. At station 135, trays or containers of all-good parts are output from the system.

In one such exemplary system, at station 110, semiconductor parts (such as microprocessors) are manufactured, wherein the semiconductor parts have one major surface (the "connector side") that has a pattern of solder-ball connectors (a ball-grid array, or BGA). It is desirable to have the balls each located at a predetermined X and Y coordinate, and each having a predetermined Z-dimension height (within a predetermined tolerance) such that the "tops" of the balls are coplanar to within a predetermined tolerance. It is also desirable to have the substrate that the balls are connected to also be planar. The major surface opposite the connector side (the "label side") is typically marked with an identification label. In one such embodiment, the devices are inspected at inspection station 115 on their connector side, then the devices are flipped over (e.g., into another tray) and inspected on their label side. In this embodiment, the inspected tray of parts are then passed to the replacement station 130, and a pick-and-place mechanism (in one embodiment, a vacuum-actuated robotic arm) removes defective parts according to data from signal 121, and replaces them with good parts from a previously inspected, partially filled tray of good parts. Thus trays having complete populations of all-good parts are output at station 135.

In another such exemplary system, at station 110, objects to be inspected (for example eggs) are placed into pocketed trays (for example, egg cartons). At station 115, the objects are inspected (e.g., for size, shape, and visible defects for example blotches or cracks). In such a system, the feedback and control through station 125 are omitted. Signal 121 is used to control the replacement of defective objects, and/or the sorting of objects into trays or containers according to size, shape, color, or other criteria. Thus the present invention can be used both in manufacturing environments as well as in the sorting and packaging of non-manufactured objects such as eggs or gemstones which may be collected from nature or other non-manufactured source.

Figure 2:
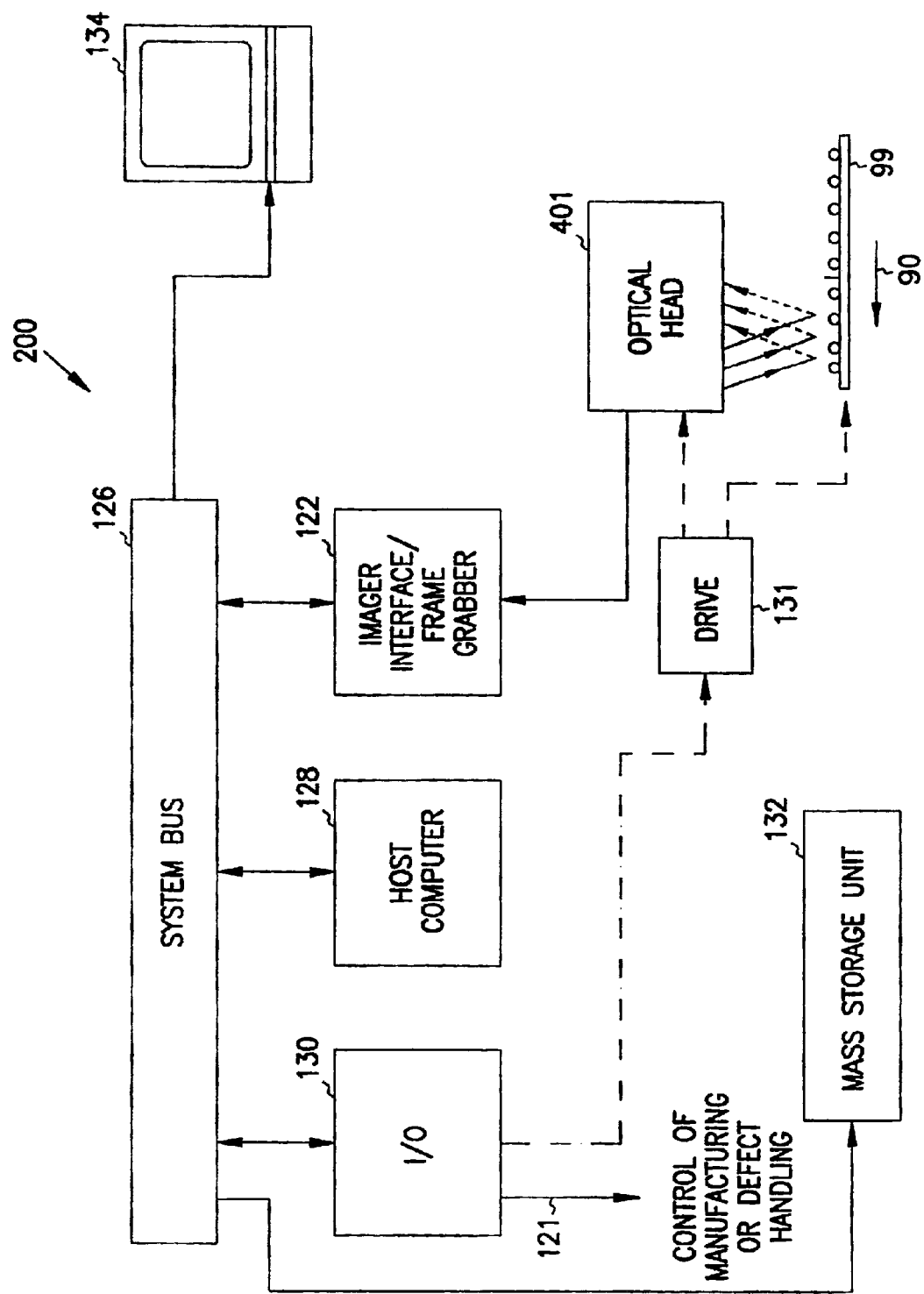
FIG. 2 shows an embodiment of the present invention, a computer controlled system 200 for the control of the imaging operation and measurement functions of system 100.

FIG. 2 shows one exemplary embodiment of the present invention, a computer controlled system 200 for the control of the imaging operation and measurement functions of system 100. Host computer 128 is coupled through system bus 126 to mass storage unit 132 (e.g., a magnetic disk subsystem), input/output (I/O) subsystem 130, imager interface 122, and display 134. In one embodiment, imager interface 122 is coupled to an optical head 401 such as shown in FIG. 4A. In one embodiment, I/O subsystem 130 controls drive 131 which moves either optical head 401 or device 99 or both, in order to obtain a relative scanning motion between the two (one embodiment which scans trays of devices 99 keeps the trays stationary during the optical scanning operation, and moves only optical head 401, in order to eliminate movement of devices 99 within the tray due to vibration from the motors, and thereby obtain more accurate measurements). In one such embodiment, drive 131 moves head 401 to first scan one or more entire rows of devices 99 in a tray in a single pass in the Y direction, then increments in the X direction, then performs a second scan of one or more entire rows of devices 99 in a single pass in the Y direction (parallel to but in the opposite direction to the first scan), and repeats this until the entire tray of parts is measured. Since each scan obtains data from a relatively wide scan stripe, there is no need to vibrate the tray to align the parts to one side of the tray pockets, or even necessarily to have tray pockets, although pockets are provided in one embodiment in order to facilitate other steps, such as pick-and-place operations to remove bad parts from trays and replace them with good parts. Imager interface 122 obtains raw scan data from optical head 401, and computes and stores processed data representative of the intensity and/or height of each X and Y coordinate of each device 99 (called "grabbing a frame"). Based on a comparison of the measured data to a predetermined set or range of acceptable or desired data, host computer 128 controls signal 121 through I/O subsystem 130. Signal 121 is used (in various embodiments) to control a step in the manufacturing process and/or to select a set of "all good" parts from among all parts produced.

Figure 3:
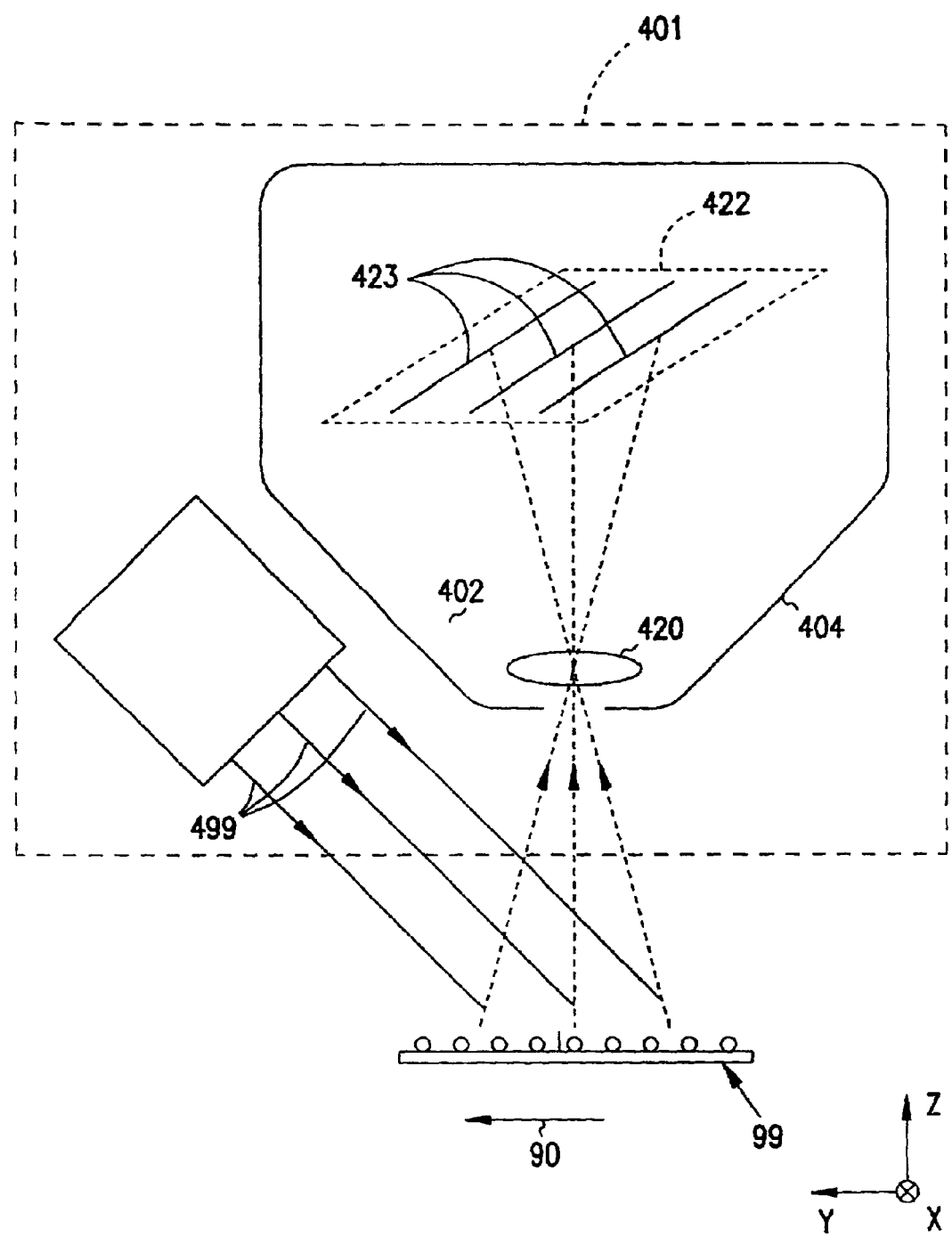
FIG. 3 shows an overview of scanning head 401.

FIG. 3 shows an overview of 3D scanning head 401. Scanning head 401 includes pattern projector 402 and imager 404. Pattern projector 402 emits a pattern of light 499 that varies in intensity along a line in the Z dimension (e.g., along the optical axis of imager 404) and along a line in the Y dimension (i.e., along the direction of travel 90). In one such embodiment, a striped Moire-type pattern is projected, wherein the pattern varies as a sine wave in the Y and Z dimensions, but for each Y and Z value, is constant in the X dimension. Imager 404 includes imaging element 420 that focusses an image of the device 99 onto the three lines of semiconductor imaging pixels of trilinear array 423 of detector 422. Each of the three lines of semiconductor imaging pixels of trilinear array 423 include a plurality of detecting pixels (e.g., 2048 pixels each) that are adjacent to one another in the X dimension (detector 422 is shown in an isometric projection in FIG. 3), and the three lines of semiconductor imaging pixels are separated from each other by a distance in the Y dimension of, for example, 8 times the X-dimension pixel-to-pixel spacing. Each point being measured on device 99 is imaged three times by moving scanning head 401 relative to device 99 in the +Y or −Y direction (e.g., in direction 90, or in the opposite direction), and capturing a data point from a pixel of the first line of semiconductor imaging pixels 423, and then on the corresponding pixel of the second and third line of semiconductor imaging pixels 423. The pattern projector 402 and the imager 404 are maintained in substantially fixed relation to each other (i.e., the projection pattern is not shifted or moved relative to the pattern projector 402 or the imager 404), and thus high measurement accuracy can be maintained. The geometric spacing of the light pattern 499 relative to the spacings between the three lines of semiconductor imaging pixels 423 is designed such that three different intensity readings are obtained for each measured point (i.e., the periodicity of light pattern 499 should not correspond exactly to spacings between the three lines of semiconductor imaging pixels 423).

In this embodiment, the head is moved in the Y direction (by a distance equal to the center-to-center X-direction-spacings of pixels between each image line detection operation), perpendicular to the pixel lines 423, so the corresponding pixel of each of the three lines of semiconductor imaging pixels 423 will measure the same point {x, y, z} in three time periods. Also in this embodiment, the pixel lines 423 are separated center-to-center by a distance equal to eight times the center-to-center X-direction-spacings of pixels. Thus each point {x,y,z} will be detected by a pixel in the first line of the three lines of semiconductor imaging pixels 423, then eight line-measurement clocks later, it will be detected by the corresponding pixel in the second line of the three lines of semiconductor imaging pixels 423, and then eight line-measurement clocks later, it will be detected by the corresponding pixel in the third line. (At each "line-measurement clock," each of the, for example, 2048 detector pixels of each line of the three-lines of semiconductor imaging pixels 423 will acquire the image of one spot of device 99, and an analog signal representing that image is transferred to a charge-coupled device (CCD) shift register, and the three sets of 2048 values each are shifted out as three parallel stream of 2048 serial analog values, and are each converted to one of three sets of 2048 digital values. By analyzing the difference between the first and second readings (displaced in this example by eight line-measurement clocks) and the difference between the second and third readings (again displaced in this example by eight more line-measurement clocks), the height (Z) of each point or spot is derived.

The function of the layout of FIG. 3 and FIG. 4 (i.e., FIGS. 4A–4I) is to project a sine-wave "Moire" pattern onto an object or device 99 and to measure each point at three places along the scan, for example, obtaining three reflected intensities with a tri-linear CCD (without the typical red/green/blue color filters).

In one embodiment, imager 404 is a Dalsa camera, and the CCD 423 used by the Dalsa camera is the Kodak KLI-2103 which contains 3 rows of 2098 active photosites (in another embodiment, the Tri-Linear CCD, part number KLI-2113, from Eastman Kodak Co, Rochester, N.Y. is used). Each photosite of the Kodak KLI-2103 measures 14 μm square and the center to center spacing between the rows is 112 μm or the equivalent of 8 pixels. In this embodiment, imaging lens 420 is a telecentric lens with the following specification: The field of view (FOV) is 2.25 inches, which is wide enough to inspect two 27 mm parts (including a separation gap of 0.125 inches). This corresponds to a maximum average magnification of m=0.514. The minimum allowed average magnification is m=0.499 (3% decrease) and the allowed magnification variation along the central axis (for one lens) is ±0.5%, but is preferred to be less than ±0.2% (which is equivalent ±½ LSB of the range measurement). Compensation can be added to the range calculations to reduce the affect of magnification variation if the variation is greater than ±0.2%. The degree of telecentricity (that is, how parallel is the central axis of the apertures across the FOV) must not change more than 0.01° over an 8 mil position change in the object plane. The position distortion must not exceed ±1% of the FOV along the central axis. Ideally the position distortion should be less than ±0.1% but this can be obtained by software compensation if the lens is unable to provide it. The maximum aperture opening must be at least f5.6 and preferably f4.0. The aperture should be adjustable. (In another embodiment, Imaging lens 420 and Projection Lens 410 are each 35 mm f/4.0 lenses from, Rodenstock company of Rockford, Ill.).

In this embodiment, the grating (i.e., projection pattern 412 of FIG. 4A) is a sinusoidal line pattern, i.e., a repeating pattern of parallel lines where the transmitted intensity varies as a sine wave as measured along a line perpendicular to the lines (Sine Patterns LLC of Penfield, N.Y. is the supplier of the Sine Pattern Grating, part number SF-3.0, used for one embodiment). The line pattern is oriented parallel to the 3 rows of the CCD. The frequency of the sinusoid and the magnification of the projection lens is chosen so that one cycle along the vertical imaging axis 421 is 25.6 mils (0.0256 inches) long to give a range resolution of 0.1 mils (0.0001 inches).

In this embodiment, the magnification of projection lens 410 (see FIG. 4A) is chosen so that one cycle along the vertical imaging axis is 25.6 mils (0.0256 inches) long. The maximum aperture must be at least f4.0 and possibly as large as f2.0. The aperture is not required to be adjustable. The magnification change across the central axis must be ±0.5% or less and preferably less than ±0.2%. The axis of the lens is rotated to provide an extended depth of focus of the line pattern in the image axis 421. The rotation is such that the grating plane 413, image axis plane 451 and projection lens plane 411 tri-sect at line 419A per FIG. 4A.

In this embodiment, lens 414 (see FIG. 4A) is a condenser lens pair that collects light from the filament 416 and focusses the filament image 478 onto the aperture of the projection lens 410. The aperture size should be at least f1.0. In this embodiment, Condenser Lens 414 is a 35 mm f/1.0, part number 01CMP013, from Melles Griot, Irvine, Calif.

In this embodiment, the recommended filament 416 is L7420 from Gilway Technical Lamp, Woburn, Mass. The size of filament 416 (see FIG. 4A) is 11.8×4.6 mm and the power is 400 watts. Other filaments with a similar power rating can be substituted.

In this embodiment, mirror 408 (see FIG. 4A) is a concave spherical mirror that has a radius equal to its distance from the filament. The purpose of spherical mirror 408 is to reflect light to the condenser lens 414. In this embodiment, a Concave Mirror, part number P43,464 from Edmund Scientific, Barrington, N.J., is used. Since filament 416 blocks the direct path, consideration is given to creating a virtual image 477 of the filament 416 adjacent to the real filament.

In this embodiment, a reflecting IR filter 450 (see FIG. 4D), e.g., IR Cut Filter, part number P43,452 from Edmund Scientific, Barrington, N.J., is used between the filament 416 and the condenser lens 414 is used to limit infrared (IR) going to the CCD because the CCD has a poor MTF response in the IR range, and to reduce spherical aberrations in the optical path.

In this embodiment, focus adjustment is provided so that the optimal focus of both optical paths 409 and 421 occurs at the object 99.

Pattern Projector 402 Having Schiempflug's Condition for Z-dimension Plane

FIG. 4A shows an isometric schematic view of one embodiment of a machine-vision head 401 for inspecting a device 99. In one embodiment, machine-vision head 401 includes a pattern projector 402 and an imager 404 (see, e.g., FIG. 4D). Pattern projector 402 includes a light source 418, projection pattern element 412, and pattern projector imaging element 410, wherein light source 418 provides light propagating generally along a projection optical axis 409. Projection optical axis 409 intersects the device 99 when the machine vision head 401 is in operation, as device 99 travels along direction 90 under head 401. In one embodiment, projection pattern element 412 is located so that the projection optical axis 409 passes through the projection pattern element 412 at an orthogonal (90 degree) angle 407. Pattern projector imaging element 410 is also located so that the projection optical axis 409 passes through the pattern projector imaging element 410. In one embodiment, pattern projector imaging element 410 is implemented as a lens.

In this entire patent application, the term "lens," unless otherwise indicated, is meant to include any type of imaging element, such as a compound or simple lens, or a hologram or diffraction pattern that acts as a lens; one such embodiment, the lens is a compound lens; in other embodiments, a simple lens is used; and in yet other embodiments, a hologram is used.

Focus Tramp Image into Projection Lens and Focus Grid Image onto Device

Lens-to-device distance $D_1$ and lens-to-grid distance $D_2$ are configured to focus an image of projection pattern element 412 at the surface of device 99 that is being inspected. In one embodiment, condensing imaging element 414 (in one such embodiment, this is a compound lens; in another, it is a simple lens as shown) is provided, and lens-to-lens distance $D_3$ and lens-to-light-source-distance $D_4$ are configured so as focus an image of light source 418 onto pattern projector imaging element 410, and in particular to enlarge an image 476 of filament 416 (for incandescent light sources) or other light source (e.g., a xenon flashlamp, or xenon-metal-halide tube) so as to fill the diameter (i.e., the effective aperture) of lens 410, in order to maximize the amount of light projected to device 99.

Linear Light Source to Increase Efficiency

One aspect of the present invention is that a pattern of light is projected onto a device being measured, and then imaged onto a linear detector 423, e.g., a trilinear-array detector. The pattern of light provides different intensities at different heights (Z dimension) and/or different points along the scan direction (Y dimension), in order to gather information needed to determine the three-dimensional geometry of the device being measured. For example, a sine-wave pattern is projected, and each point is measured at three different phases of a single cycle of the sine pattern. The system is designed so that the first phase measurement is detected by a pixel on the first line of the linear detector 423, the second phase measurement is detected by a pixel on the second line of the linear detector 423, and the third phase measurement is detected by a pixel on the third line of the linear detector 423. For such a three-phase measurement, light from other phases of the sine-wave light pattern is not needed, and should be blocked so reflections form that light do not interfere with the desired measurement.

In one embodiment, light source 418 includes a elongated incandescent filament 416 wherein the longitudinal axis 406 of filament 416 is perpendicular to projection optical axis 409 and parallel to the grid lines of projection pattern element 412. In one embodiment, a spherical or cylindrical reflector 408 is provided to focus an image 477 of filament 416, wherein filament image 477 is adjacent to filament 416, in order to maximize the usable light projected towards device 99. (See FIG. 4A, showing filament 416, the first filament image 476 focussed by lens 414 to fill the width (X-dimension) of lens 410, the second filament image 477 of filament 416 as focussed by reflector 408 to be adjacent to filament 416, and the third filament image 478—being an image of second filament image 477—focussed by lens 414 to fill the width (X-dimension) of lens 410.)

In one embodiment, a mask 442 is provided to reduce light that does not contribute to the imaging function (i.e., light that, although perhaps properly imaged from pattern 412 to object 99, might reflect off of surfaces that are not meant to be in the field of view of the imaging components). In one such embodiment, mask 442 has a elongated aperture 443 located adjacent to or in close proximity to projection pattern element 412, and wherein the long axis of aperture 443 is parallel to the "lines" of the pattern of projection pattern element 412. In one such embodiment, projection pattern element 412 includes a pattern 472 that transmits light having an intensity that varies in a sinusoidal pattern in the Z dimension (and in the Y dimension), but that is constant across its width in the X dimension. I.e., pattern 472 varies substantially as a sine wave 474 along line 475 within element 412, but is substantially constant along lines 473 that are perpendicular to line 475 (see FIG. 4E). Thus light 499 is imparted with a spatial-modulation pattern 494 that varies as a sine wave in intensity in one transverse direction (parallel to line 475), and that is substantially constant along lines parallel to lines 473 that are perpendicular to line 475 (see FIG. 4E). It is this pattern that allows measurements (e.g., three measurements at three different phases of pattern 494) to determine 3D geometric measurements of part 99.

The device-to-imaging-lens distance $D_5$ and imaging-lens-to-trilinear-element distance $D_6$ are configured so as focus an image of device 99 onto trilinear array 423.

Imager 404 has a reception optical axis 421, the reception optical axis 421 intersecting the device 99 when the machine vision head 401 is in operation. Imager 404 is maintained in a substantially fixed relationship to the pattern projector 402. In one embodiment, imager 422 includes three lines of semiconductor imaging pixels 423 (also called trilinear array 423).

Schiempflug's condition is where the plane of the object, the plane of the lens, and the plane of the image all intersect at a single line. When Schiempflug's condition is satisfied, an optimal focus of the image of the object onto the image plane is achieved. Thus, wherein the image plane is tilted to the plane of the lens (thus these two plane intersect at a line), then the plane of the object should be tilted so as to intersect the other two planes at the same line.

In one embodiment, the projection pattern element 412, the pattern projector imaging element 410, and a third plane 451 substantially satisfy Schiempflug's condition. In one such embodiment, the reception optical axis 421 and the center line of trilinear array 423 both lie in the third plane 451. When used to scan according to the present invention, the image formed on trilinear array 423 represents a very narrow elongated area of device 99, i.e., narrow in the direction 90 (dimension Y) and much longer in the direction perpendicular to the paper of FIG. 4A (dimension X). However, as the height of features such as solder balls 97 or substrate 98 varies, there is more distance in this direction (dimension Z) that must be accommodated (i.e., perhaps several Moire fringes in the Z dimension when measuring the height of a pin on a pin-grid array device), or there is a desire for increased accuracy of measurement in the Z dimension. Thus, in this embodiment, the third plane 451 is in the X-Z dimension, and Schiempflug's condition is satisfied by an intersection of plane 411 (the plane that contains the diameters of lens 410), plane 413 (the plane that contains the diameters of projection pattern 412) and a third plane at line 419A, as shown in FIG. 4A. In one such embodiment, the reception optical axis 421 lies within the third plane 451 or is substantially parallel to the third plane 451. In another such embodiment, the longitudinal axis of the center line of trilinear array 423 also lies within the third plane 451 or is substantially parallel to the third plane, as shown in FIG. 4A. Such an arrangement provides for an increased depth of focus in the Z-dimension for projected pattern 499.

Figure 4B:
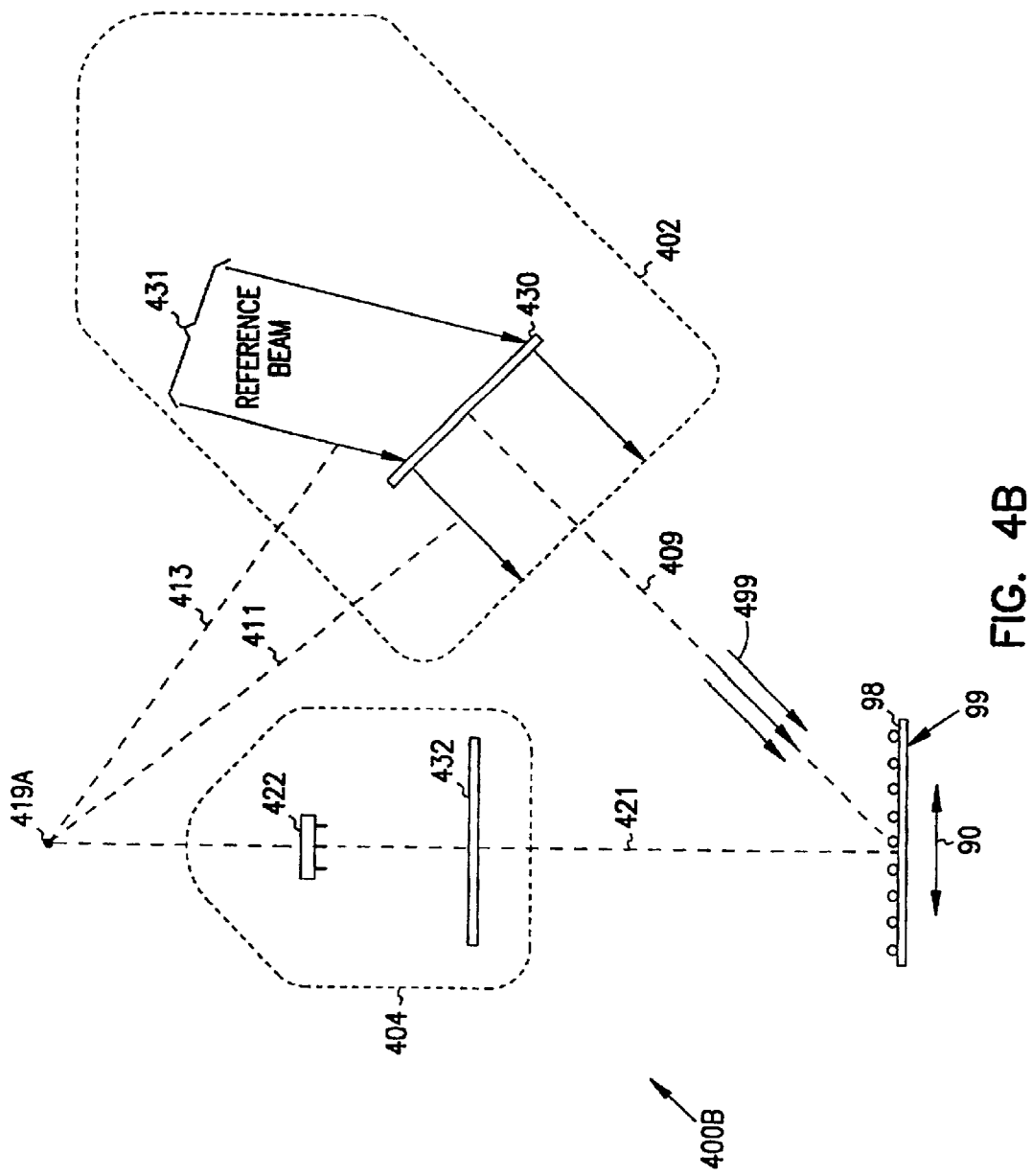
FIG. 4B shows another embodiment of a machine-vision head 401.
Figure 4C:
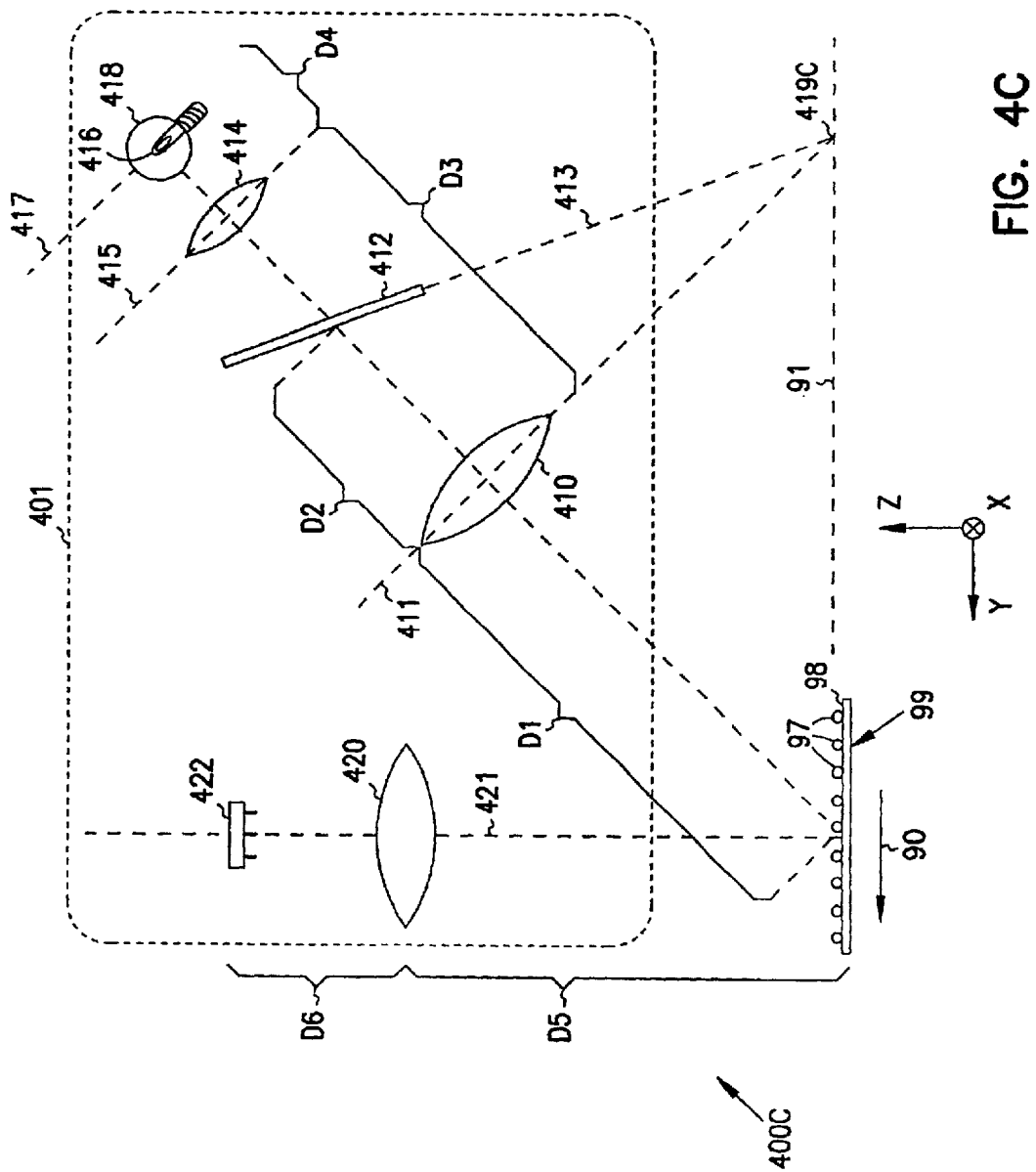
FIG. 4C shows yet another embodiment of a machine-vision head 401.

FIG. 4C shows a cross-section view of yet another embodiment of a machine-vision head 401 of a machine-vision system 400C. A plane 91 lies across the surface of device 99 being measured (the edge of plane 91, parallel to and at or near the surface of device 99, is shown in FIG. 4C). Machine-vision system 400C is otherwise the same as system 400A of FIG. 4A described above, however, Schiempflug's condition is satisfied for the pattern plane 413, lens plane 411, and plane 91 which intersect at line 419C which extend in the Y dimension (perpendicular to the sheet at the point marked 419C on FIG. 4C).

Figure 4D:
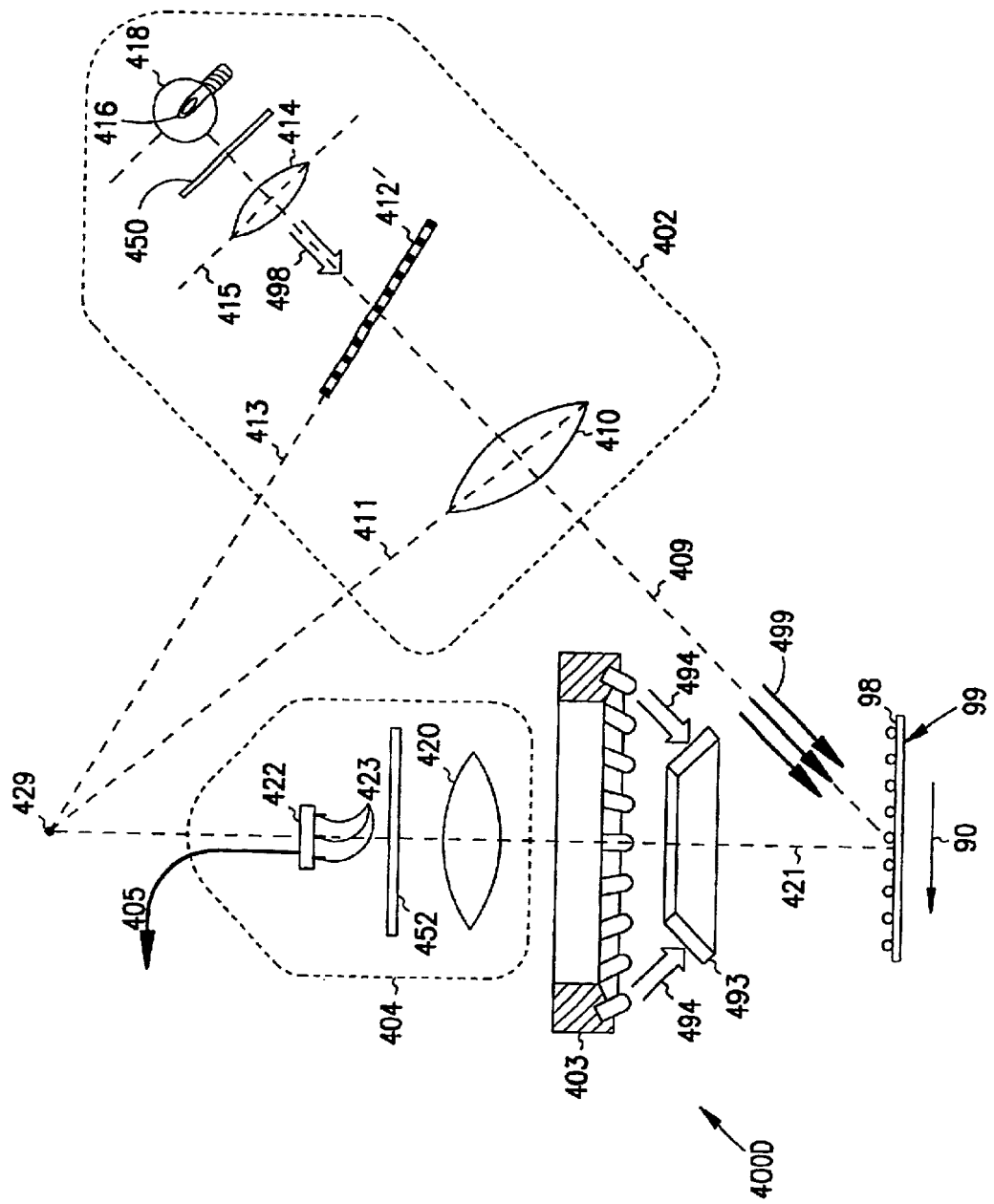
FIG. 4D shows still another embodiment of a machine-vision head 401.

FIG. 4D shows still another embodiment of a machine-vision head 401D. The machine vision system 400D is otherwise the same as system 400A shown in FIG. 4A, but with the addition of a non-patterned light source 403 (such as the ring-light shown, or other source of general, non-patterned light 494), and IR filter 450. Non-pattered light source 403 is non-patterned in the sense that the non-patterned light 494 has a substantially uniform intensity in the X, Y, and Z dimensions at the portion of device 99 that is imaged onto detector 423 (in contrast to patterned light 499 which varies in the Y and Z dimensions). One embodiment includes a diffuser 493 which reduces specular reflections from, e.g., the individual LED light sources, of non-patterned light source 403. In one embodiment, a scan is performed by time-interleaving flashes from pattern projector 402 with flashes from non-patterned light source 403, each of which is detected by imager 404. The received image signals 405 are then demultiplexed, such that 2D images (i.e., the intensity of reflected light from each X and Y point) are derived from the non-pattered light 494, and 3D images (i.e., including the calculated Z height of each X and Y point) are derived from the patterned light 499. The projection pattern element 412' shown in FIG. 4D represents a square-wave pattern, but is implemented as a sine-wave pattern in other embodiments.

Figure 4E:
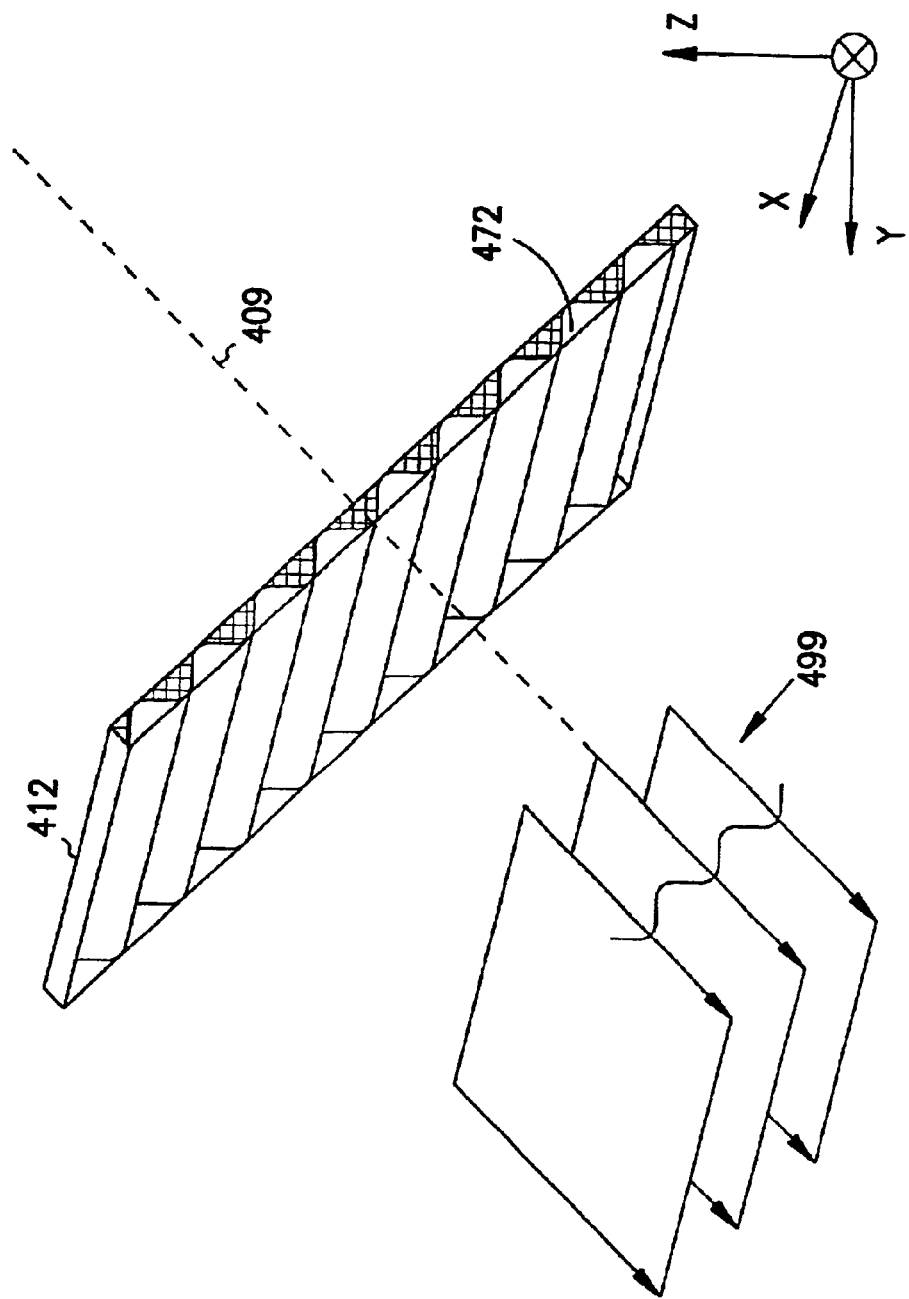
FIG. 4E shows a projection pattern element 412 having a density pattern 472 that is a sine-wave in one direction.

FIG. 4E shows a projection pattern element 412 having a density pattern 472 that is a sine-wave in one direction, and a constant density in the perpendicular direction of the plane of the element. In such an embodiment, pattern projector 402 provides a projected pattern 499 whose intensity along a line segment (e.g., a line segment along reception optical axis 421 at and near device 99) varies as a sine wave. In one embodiment, the projected pattern has a sharp focus at a plane 451 containing the line reception optical axis 421 and the center line of the three lines of optical detector pixels of trilinear array 423.

The projection pattern element 412' of another embodiment shown in FIG. 4F represents a square-wave pattern. In one such embodiment, pattern projector 402 provides a projected pattern 499 whose intensity along a line segment (i.e., a line segment very near pattern projector 402) varies as a series of pulses. In one such embodiment, the series of pulses is substantially a square wave, i.e., the pattern is a series of parallel of unilluminated and illuminated stripes (colloquially, "black-and-white" stripes). In one such embodiment, these square waves are of such a fine pitch that the projected pattern 499 "blurs" or "diffracts" into substantially a sine-wave pattern of projected light, as measured on a line segment in the Z dimension (and on a line segment in the Y dimension) at device 99. Projection pattern element 412' replaces projection pattern element 412 of FIG. 4A in some embodiments.

The projection pattern element 412" of two other embodiments shown in FIGS. 4G and 4H represent an interleaved square-wave pattern. In FIG. 4G, two glass plates are separated by a space (e.g., by air) and each has a parallel pattern on a single face, while in FIG. 4H, a single plate having a parallel stripe pattern on one face and a complementary parallel stripe pattern on the opposite face. In one such embodiment, the series of pulses is substantially a square wave, i.e., the pattern is a series of parallel of opaque and transparent stripes (colloquially, "black-and-white" stripes), interleaved with another complementary pattern of parallel of opaque and transparent stripes that is spaced in the direction of light propagation 409. In one such embodiment, these square waves are of such a fine pitch that the projected pattern 499 "blurs" or "diffracts" around the complementary edges into substantially a sine-wave pattern of projected light, as measured on a line segment in the Z dimension (and on a line segment in the Y dimension) at device 99. Projection pattern element 412" replaces projection pattern element 412 of FIG. 4A in some embodiments.

Movable Slit Aperture to Accommodate Different Heights of Devices

Figure 4I:
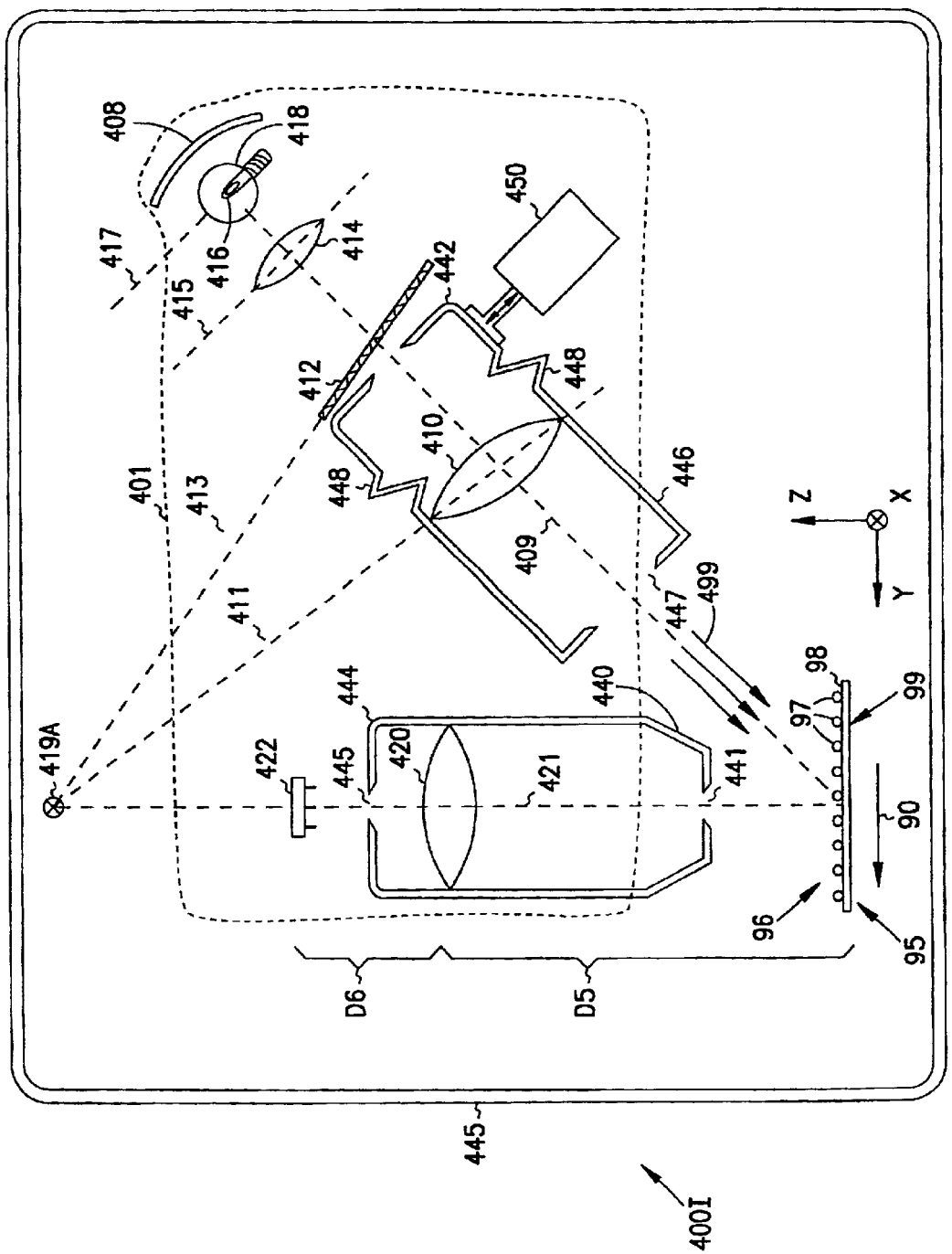
FIG. 4I shows yet another embodiment of a machine-vision head 401.

FIG. 4I shows yet another embodiment of a machine-vision head 401. FIG. 4I shows a system 400I that is otherwise the same as system 400A of FIG. 4A, but with mask 442 having a slit aperture 443 which can be adjusted using linear actuator 450. Linear actuator 450 moves only the position of the aperture 443; it does not move projection pattern 412. In typical uses of the present invention, devices 99 are placed into trays for inspection. It is desirable to inspect devices that differ in height (or trays that are thicker or thinner, and thus present devices at different heights relative to the tray), and linear actuator 450 allows moving aperture 443 so the light projects onto the portion of the device to be measured. In one embodiment, the computer control system dynamically adjusts linear actuator 450 so the light passed by mask 442 is projected only on the portion of device 99 that is imaged onto detector 423, in order to keep the scan on the height of interest. In other embodiments, a static adjustment of actuator 450 is made to set the projector for the expected height of the tray or devices.

FIG. 4B shows another embodiment, wherein the projection pattern element 412 and the pattern projector imaging element 410 are combined and implemented as a single hologram 430 or other suitable diffraction pattern (i.e., see the cross-section view of FIG. 4B wherein projection pattern element 410 and pattern projector imaging element 412 are replaced by hologram 430). Hologram 430 is fabricated using methods well known in the art (such as, for example, by forming a hologram of a projection pattern element 412 and pattern projector imaging element 410 and, or by forming a hologram of a hologram of projection pattern element 412 and pattern projector imaging element 410), and represents the interference of a reference beam with light as modified by projection pattern element 412 and pattern projector imaging element 410. Then, when illuminated by a suitable reference beam 431 (such as an expanded collimated laser beam), the desired projected Moire light pattern 499 is produced, having a focus range that is extended in the Z dimension at device 99. One advantage of such an arrangement is that the coherent light of the laser light source is more sharply focussed, particularly when using a hologram focusing element 430.

In one such embodiment, the reception optical axis 421 lies within the third plane 451 or is substantially parallel to the third plane 451, which substantially satisfies Schiempflug's condition when combined with hologram 430 (which has a diffraction pattern representing or equivalent to projection pattern element 412 and pattern projector imaging element 410 with their planes 413 and 411 respectively, at an angle to one another.

Interferometric Measurement at 45-degree Angle to Minimize Specular Reflection

Shiny objects, such as solder ball connectors on ball-grid array (BGA) devices or pins of pin-grid-array (PGA) devices, present challenges for optical measurement, because of specular reflections. Further, such pins or solder balls present challenges due to shadowing of the relatively tall connector which obscures features "behind" the connector.

Figure 5A:
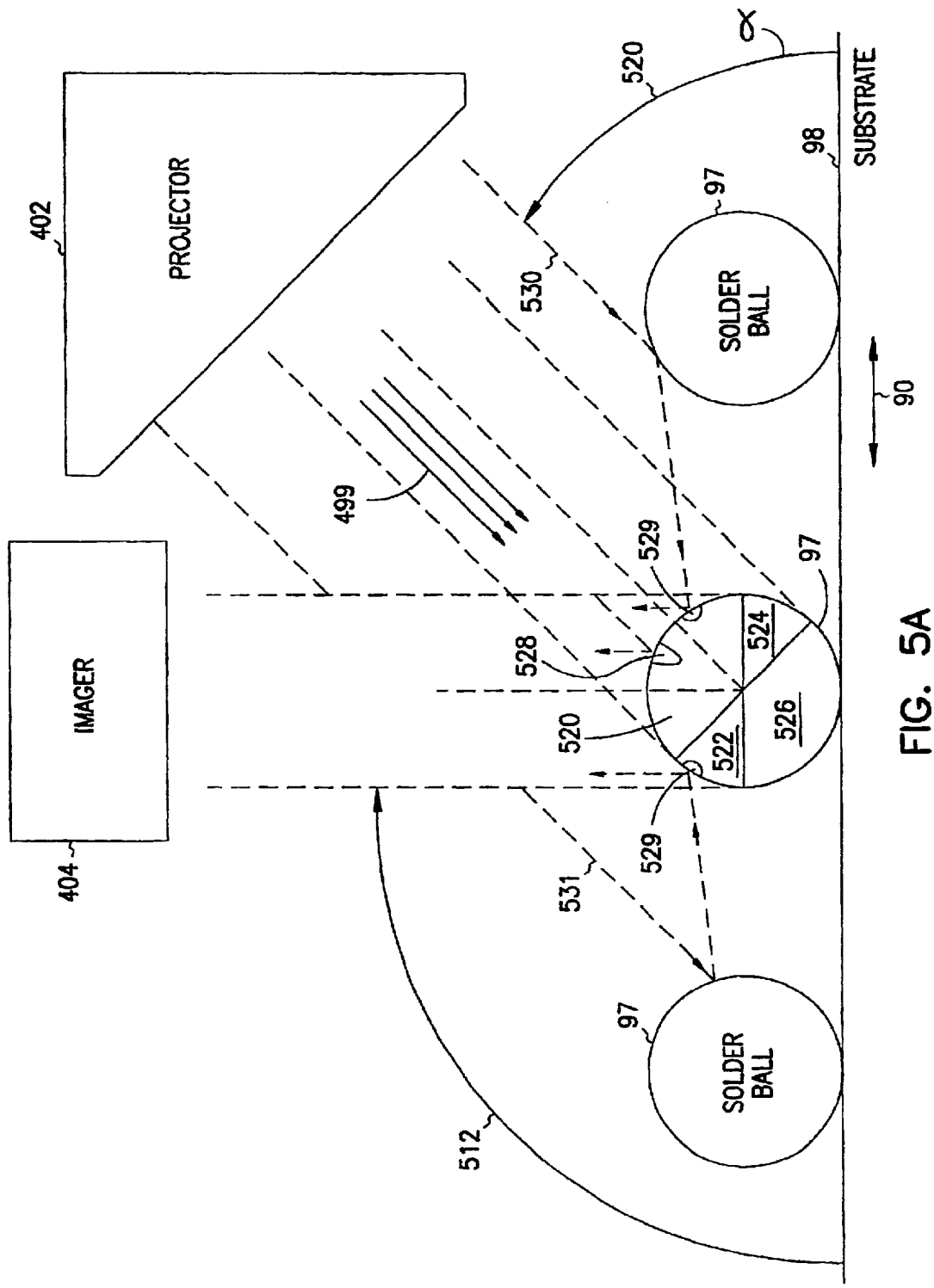
FIG. 5A shows a solder ball 97, illustrating the various illuminated and imagable regions.

FIG. 5A shows one embodiment of the present invention that provides pattern projector 402 at a forty-five (45)-degree angle 510 to the direction of motion 90 (other embodiments use an angle α 510 (see FIG. 5) of between about 45 degrees and about 50 degrees). FIG. 5A shows region 520 of a solder ball 97 that is both lit by pattern light 499 and imagable by imager 404, region 522 that is not lit by pattern light 499 but would have been imagable by imager 404 ("in the dark"), region 524 that is lit by pattern light 499 but not imagable by imager 404 ("under the ball"), and region 526 that is neither lit by pattern light 499 nor imagable by imager 404 ("under the ball and in the dark"). Since the angle of incidence equals the angle of reflection, the center of the specular reflection 528 on a spherical solder ball will be about 23 degrees from the top of the ball, thus away from the top of the ball where the measurements most critical to accurately measuring the height and position of the top of the ball are made. Region 528 represents that portion of ball 97 where a specular reflection will saturate the detector 423 in imager 404, preventing any accurate height measurement (most of the rest of region 520 provides accurate measurement from diffuse reflection). Further, the amount of shadowing (i.e., the area of region 522) is reduced as compared to using a smaller angle 510 relative to the direction of motion.

In FIG. 5A, ray 530 and ray 531 represent light that reflects from neighboring balls 97 onto the ball 97 being measured. Regions 529 represent portions of the center ball 97 which have specular reflected light from rays 530 and 531 reflected from neighboring balls in the Y direction (all such light which is reflected from neighboring features is "noise" light that reduces the accuracy of height measurements). By providing a slit mask 442 (i.e., a mask having an aperture that extends in the X-dimension but is much narrower in the Y-dimension; see FIG. 4A), the source light for rays 530 and 531 is blocked or reduced, preventing or reducing the reflections from features in the Y dimension from reaching the portion of device 99 being measured.

In other embodiments, mask 442 is designed to reduce unwanted reflections of light from features displaced in the X-dimension as well. For example, color-filter stripes (e.g., a repeating pattern of red and blue stripes) that are perpendicular to the long axis of the aperture 443 are used in one embodiment to reduce noise reflections from the X-dimension.

Figure 5C:
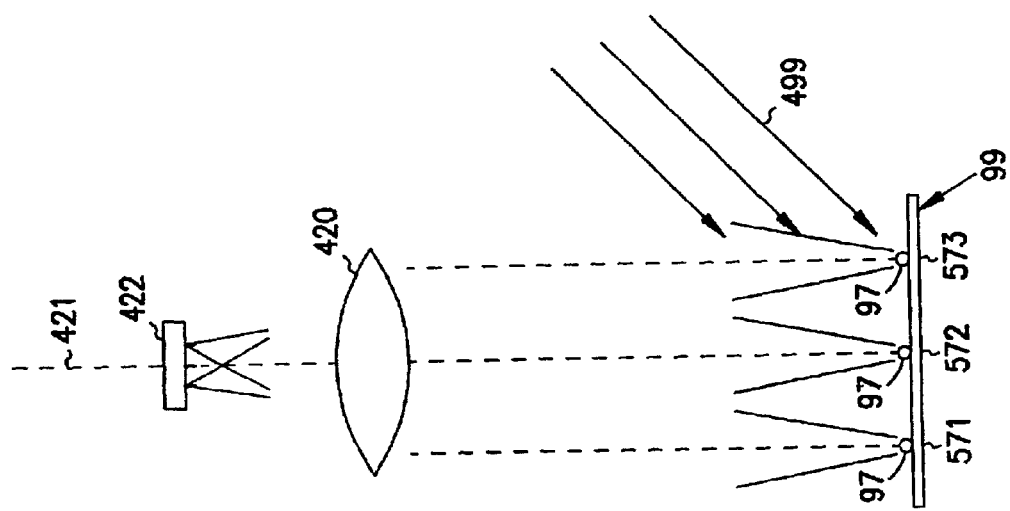
FIG. 5C is a representation of light gathered by a telecentric lens 420.
Figure 5B:
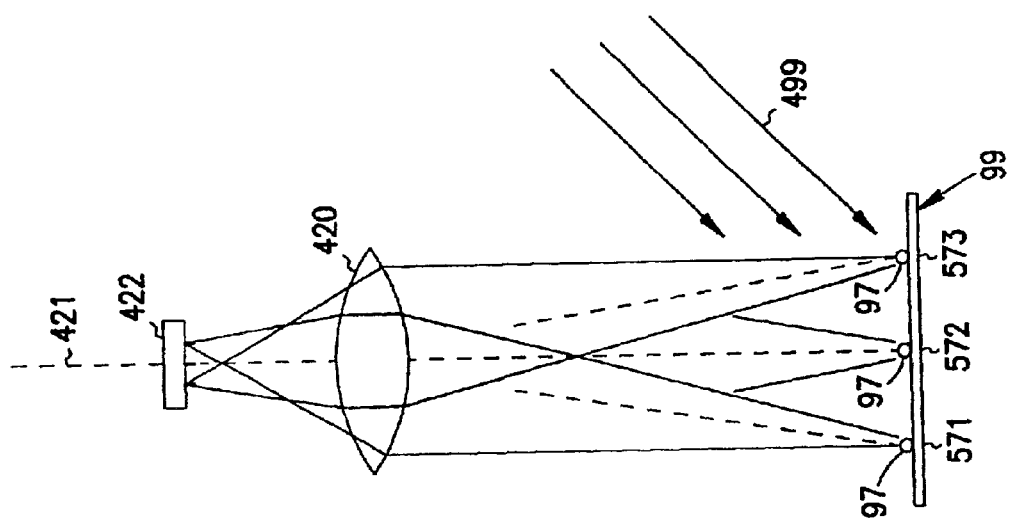
FIG. 5B is a representation of light gathered by a non-telecentric lens 420.

FIG. 5B is a representation of light gathered by a non-telecentric lens 420. In detecting the light at the three measurement points 571, 572, and 573, the projected light 499 is gathered from cones that center on the aperture of lens 420. This can cause measurement errors due to gathering light at different reflection angles for the three measurements of the ball 97 as it moves from point 571 to 572 to 573. In contrast, FIG. 5C is a representation of light gathered by a telecentric lens 420. A telecentric lens (or other similar imaging element) 420 gathers light as if from an infinite number of apertures, and thus the light gathered is from the same reflection angle (i.e., a vertical angle for this embodiment) for the three measurements of the ball 97 as it moves from point 571 to 572 to 573 in FIG. 5C. Thus a telecentric imaging lens 420 provides increased measurement accuracy for some embodiments.

In one embodiment, projection pattern element 412 is a Sine Pattern Grating, model SF-3.0, available from Sine Patterns LTD, Penfield, N.Y.; Imaging lens 420 and Projection Lens 410 are 35 mm f/4.0, available from Rodenstock, Rockford, Ill.; Condenser Lens 414 is 35 mm f/1.0, model 01CMP013, available from Melles Griot, Irvine, Calif.; light source 481 is a Halogen Lamp, 400 watt, model L7420, available from Gilway Technical Lamp, Woburn, Mass.; IR filter 450 is an IR Cut Filter, model P43,452 available from Edmund Scientific, Barrington, N.J.; reflector 408 is a Concave Mirror, model P43,464, available from Edmund Scientific, Barrington, N.J.; trilinear array detector 423 is a Tri-Linear CCD, model KLI-2113, available from Eastman Kodak Co, Rochester, N.Y.

Figure 6:
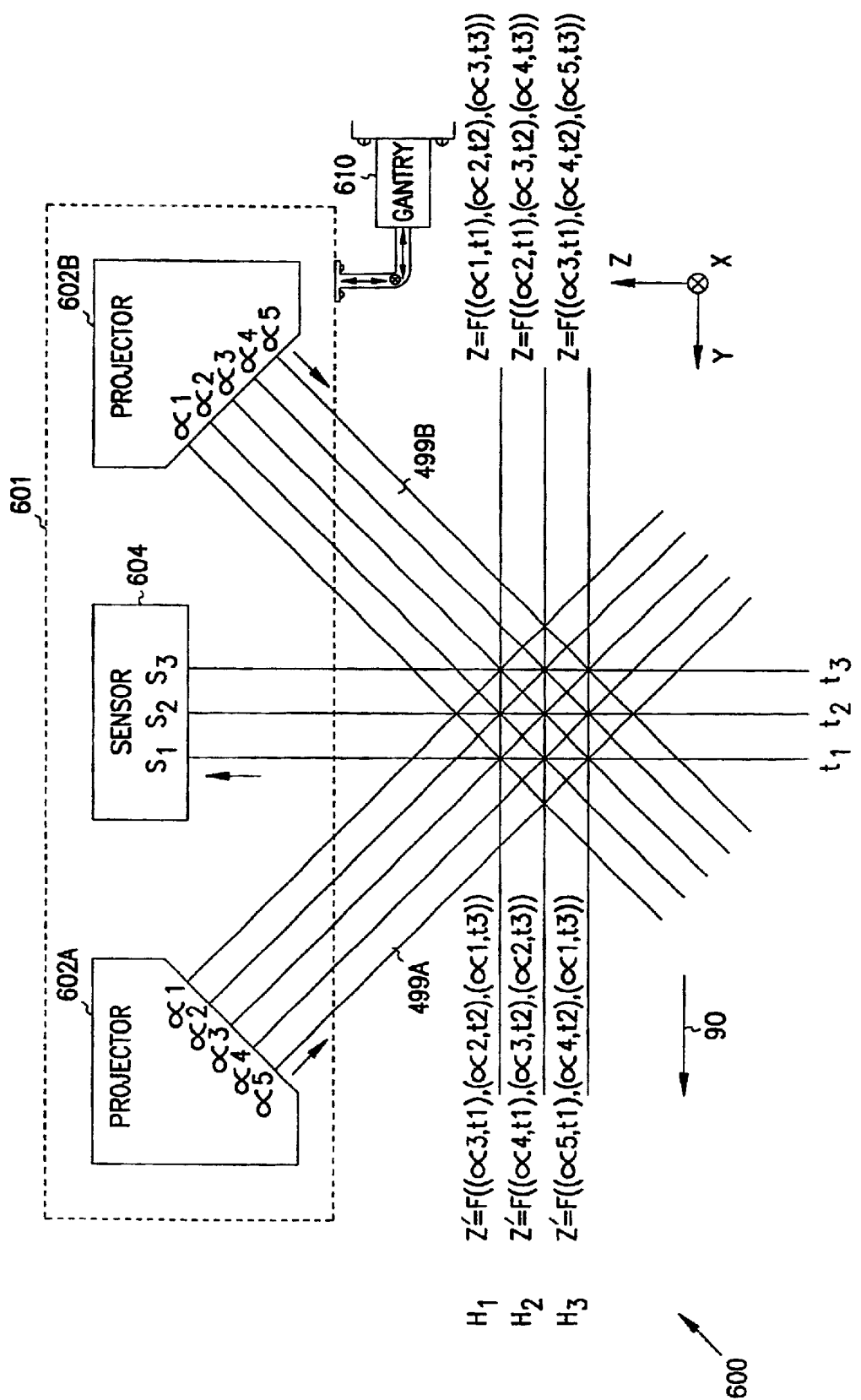
FIG. 6 shows machine-vision system 600 that represents another embodiment of the present invention having more than one projector in a scanning head.

FIG. 6 shows machine-vision system 600 that represents another embodiment of the present invention having more than one projector 602 in a scanning head 601. In one embodiment, gantry 610 (not shown to scale) is used to scan head 601 in the Y direction during measurement, but is also used to move-head 601 in the X direction for successive scan operations, and to move head 601 in the Z direction to adjust for thicker or thinner devices, for example. In the embodiment shown, projector 602A projects a light pattern 499A that includes, for example, phases (i.e., phase angles of a sine wave) α1, α2, α3, α4, and α5, where the line for α1 represents a plane perpendicular to the drawing sheet having a constant light intensity representing α1, the line for α2 represents a plane perpendicular to the drawing sheet having a constant light intensity representing α2, etc. (Actually, a sine wave pattern having an infinite number of intermediate phases is projected, five of which are shown in this illustration.) Similarly, projector 602B projects a light pattern 499B. In this embodiment, the first projector 602A and the second projector 602B are oriented substantially opposite from one another relative to the imager 604, and their patterns of light 499A and 499B provide grid lines that project parallel to one another when projected onto a horizontal (x-y) or vertical plane (y-z). Scanning is done by moving head 601 in the Y direction. In this embodiment, the optical axis of sensor 604 is a right angles to the direction of scanning 90 (the Y direction), and each point of device 99 is measured at Y1 at a first point in time t1, at Y2 at a second point in time t2, and at Y3 at a third point in time t3. (For example, when a 3-by-2048 trilinear detector 423 is used, the 50th pixel of the first line, the 50th pixel of the second line, and the 50th pixel of the third line are used for the first, second and third measurement respectively of each point 50/2048ths of the way across the scan path, and a corresponding pixel of each of the three lines gathers information for the other points of the scan.) In one embodiment, projector 602A and projector 602B are oriented one-hundred eighty degrees from one another relative to sensor 604, and are strobed alternately (i.e., flashes of light from each projector are interleaved) (one strobe for each triple scan-line operation), and a single sensor 604 is used to gather the image information. In such an embodiment, an LED, laser, xenon, arc lamp, or other strobable or shutterable light source is used. This allows gathering of light from all sides of a feature (e.g., relative to FIG. 5A described above, the unlit region 522 from projector 602A would be in the illuminated region 520 of projector 602B, and vice versa) with little or no shadowing relative to the projectors. In one such embodiment, sensor 604 is at a 90-degree angle to the Y dimension, projector 602A is at a 45-degree angle, and projector 602B is at a 135-degree angle (i.e., at a 45-degree angle on the other side).

In another such embodiment, a complete scan in the +Y direction, for example, with only projector 602A providing illumination, would be followed by a complete scan in the −Y direction, for example, with only projector 602B providing illumination. Thus features that were shadowed during one scan would be illuminated during the other scan. In such an embodiment, an incandescent (non-strobed) or strobable light source is used.

In yet another embodiment, the light from projector 602A is filtered or from a monochromatic light source (e.g., red color), and is at a different color (frequency) than the light from projector 602B which is filtered or from a monochromatic light source at a different color (e.g., blue light). In this embodiment, sensor 604 is provided with a color separator (e.g., a dichromatic beamsplitter), and one trilinear detector 423 for each color. (See FIGS. 9A, 9B, and 9C below for further description.)

In still another embodiment, the light from projector 602A is polarized, and is at a different polarization than the light from projector 602B which is also polarized. In this embodiment, sensor 604 is provided with a polarization separator (e.g., a polarized beam splitter), and one trilinear detector 423 for each polarization.

In the embodiment shown in FIG. 6, the optical axis of sensor 604 is at right angles to the scan direction 90, and thus each point is measured at the same Y1, Y2, and Y3 positions by sensor lines S1, S2, and S3, respectively, regardless of height (i.e., the Z dimension). Thus, the Z dimension of a point having height H1 would be measured relative to projector 602B as a function of ($\alpha$1 at time t1 measured by sensor S1, $\alpha$2 at time t2 measured by sensor S2, and $\alpha$3 at time t3 measured by sensor S3) measured from projection pattern 499B. Similarly, the Z dimension of a point having height H2 would be measured relative to projector 602B as a function of ($\alpha$2 at time t1 measured by sensor S1, $\alpha$3 at time t2 measured by sensor S2, and $\alpha$4 at time t3 measured by sensor S3) measured from projection pattern 499B. In one embodiment, one or more linear encoders are used to determine the exact position of head 601 in the X and Y directions at each point in time, providing X and Y coordinated for each point measured. The Z dimension is derived from the three phase measurements made for each point, since each point's height has a unique intersection with the various phases projected. In one embodiment, the intensity for each point is also derived from these measurements. The Z dimension derived from the measurements made from the light projection pattern 499A (denoted z') is also derived using similar measurements. Table 1 below illustrates the derivation of the height dimension (z for the measurements from projector 602B, and z' for the measurements from projector 602A) for three heights H1, H2, and H3.

TABLE 1

| Height | Measurement using projector 602A | Measurement using projector 602B |
|---|---|---|
| H1 | z' = f(($\alpha$3, t1), ($\alpha$2, t2), ($\alpha$1, t3)) | z = f(($\alpha$1, t1), ($\alpha$2, t2), ($\alpha$3, t3)) |
| H2 | z' = f(($\alpha$4, t1), ($\alpha$3, t2), ($\alpha$2, t3)) | z = f(($\alpha$2, t1), ($\alpha$3, t2), ($\alpha$4, t3)) |
| H3 | z' = f(($\alpha$5, t1), ($\alpha$4, t2), ($\alpha$3, t3)) | z = f(($\alpha$3, t1), ($\alpha$4, t2), ($\alpha$5, t3)) |

Figure 7:
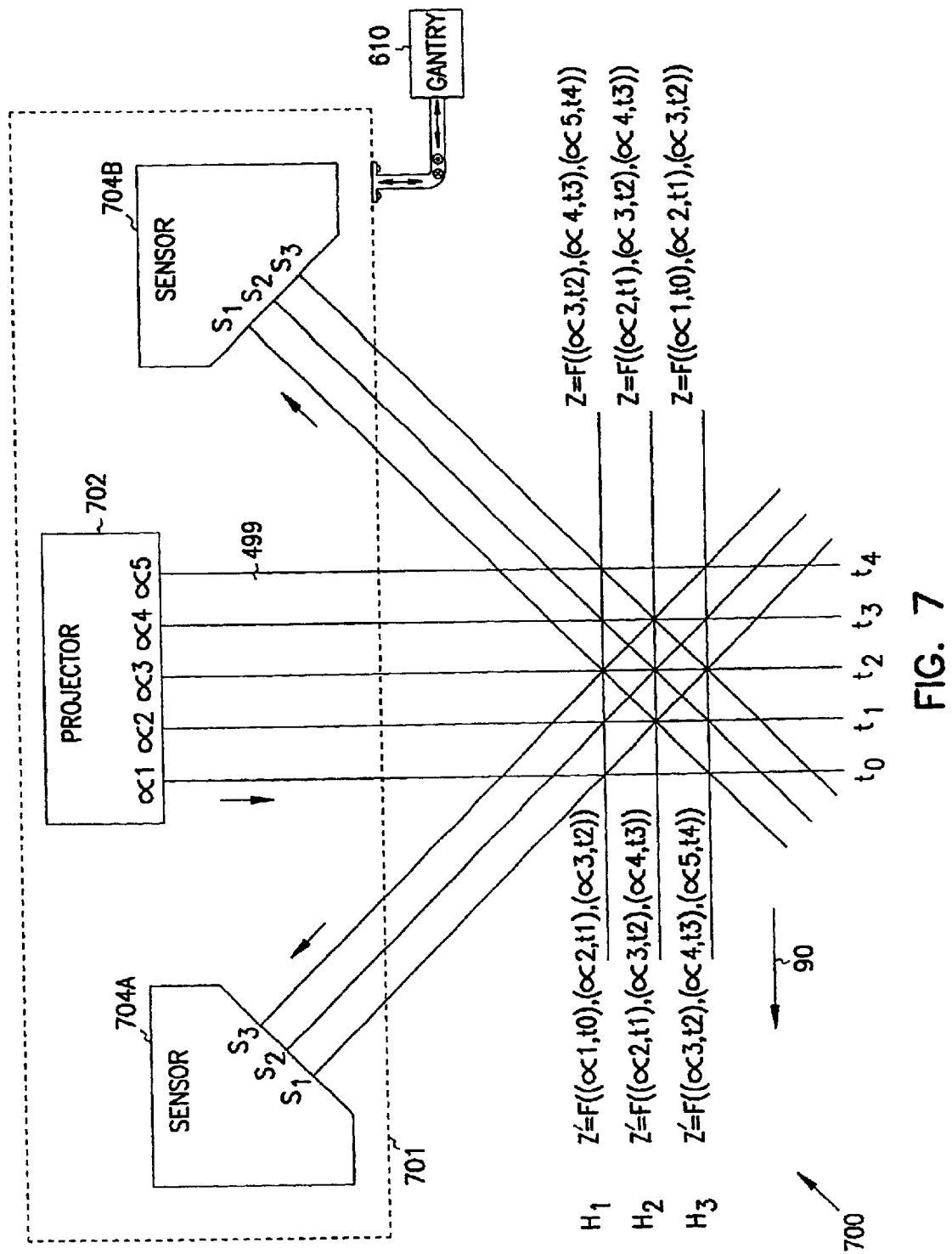
FIG. 7 shows machine-vision system 700 that represents another embodiment of the present invention having more than one imager in a scanning head.

FIG. 7 shows machine-vision system 700 that represents another embodiment of the present invention having more than one imager 704 in a scanning head 701. In one such embodiment, projector 702 is at a 90-degree angle to the Y dimension, sensor 704A is at a 45-degree angle, and sensor 704B is at a 135-degree angle (i.e., at a 45-degree angle on the other side). In contrast to the system 600 of FIG. 6 in which any feature is measured at the same sensor pixel at a given time, independent of its height, the system 700 of FIG. 7 must take into account the fact that a feature will shift in time (i.e., in the Y direction) as it varies in height. For example, if a point has height H1, it will be measured at times t0, t1, and t2 by sensors s1, s2, and s3 respectively, but would be measured at times t2, t3, and t4 respectively if it had height H3. Thus the derived height information is used to correct for Y-direction displacement caused by not having the optical axis of sensors 704A and 704B not at right angles to the direction of scanning 90. Further, the reader will note that the time points used to measure a feature on device 99 will shift as the heights shift beyond the amount which can be measured by a particular pixel at a particular time. However, because heights often change gradually, all heights can generally be derived accurately (e.g., for Projector 602A, if the height difference between H1 and H2 is h, then for heights H1±h/2, the heights are derived using the measurements from times t0, t1, and t2; for heights H2±h/2, the heights are derived using the measurements from times t1, t2, and t3; and for heights H3±h/2, the heights are derived using the measurements from times t2, t3, and t4). Since measurements are repeated for hundreds or thousands of time points t, and are stored in a data structure representing every time point, the data needed to correct for the time shift due to height changes is available and used to correct the Y values according to the derived Z value of each point. Table 2 shows the relationship of these values.

TABLE 2

| Height | Measurement using projector 602A | Measurement using projector 602B |
|---|---|---|
| H1 | z' = f(($\alpha$1, t0), ($\alpha$2, t1), ($\alpha$3, t2)) | z = f(($\alpha$3, t2), ($\alpha$4, t3), ($\alpha$5, t4)) |
| H2 | z' = f(($\alpha$2, t1), ($\alpha$3, t2), ($\alpha$4, t3)) | z = f(($\alpha$2, t1), ($\alpha$3, t2), ($\alpha$4, t3)) |
| H3 | z' = f(($\alpha$3, t2), ($\alpha$4, t3), ($\alpha$5, t4)) | z = f(($\alpha$1, t0), ($\alpha$2, t1), ($\alpha$3, t2)) |

Figure 8:
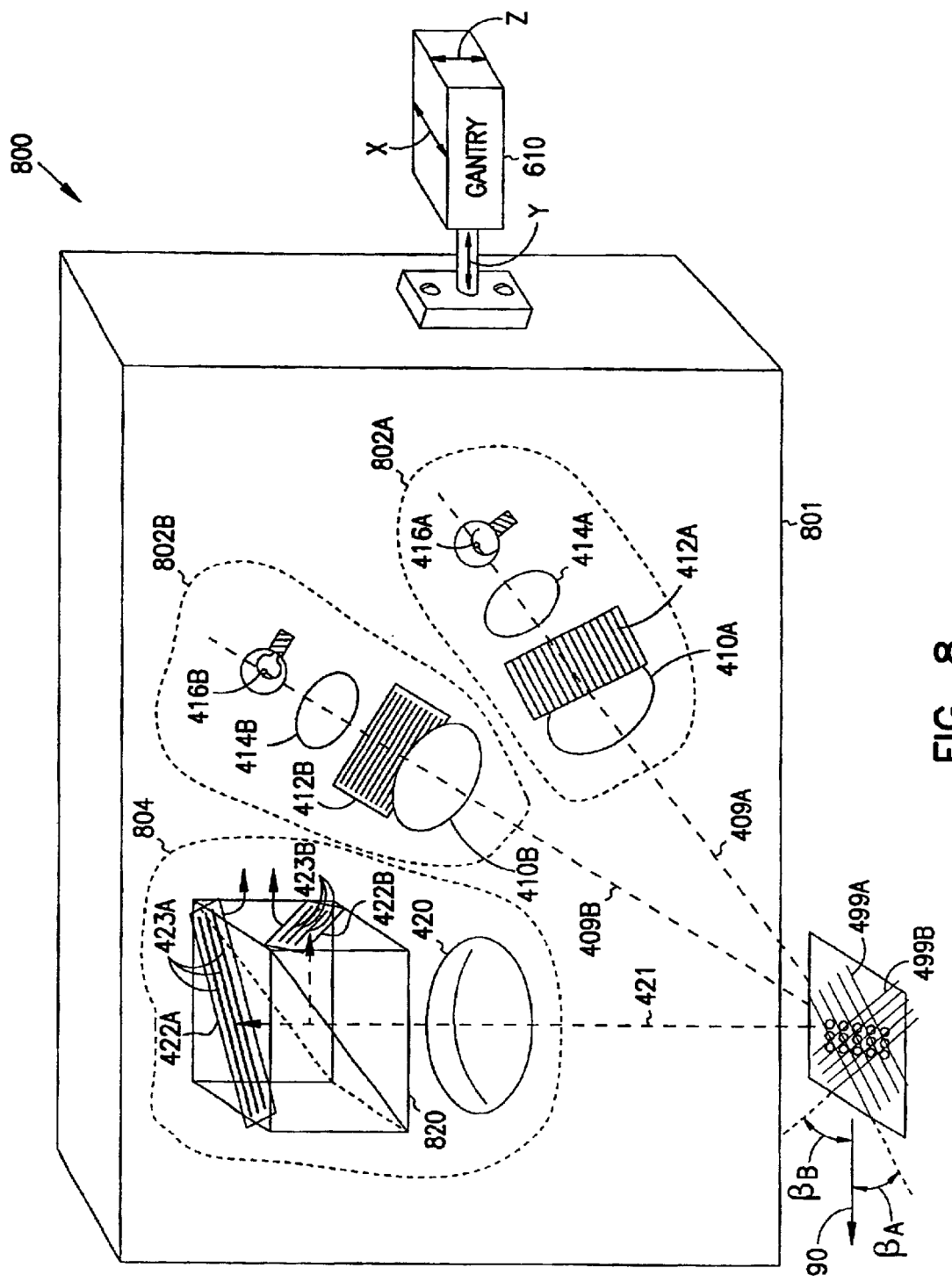
FIG. 8 shows machine-vision system 800 that represents another embodiment of the present invention having more than one projector and more than one imager in a scanning head.

FIG. 8 shows machine-vision system 800 that represents another embodiment of the present invention having more than one projector 802 and more than one imager in a scanning head 801. In this embodiment, projector 802A has a projection optical axis at a compound miter angle and projects sine-wave pattern 499A, wherein the lines of constant intensity are at a 45-degree angle $\beta_A$ to the direction of scanning 90 (rather that the 90-degree angle used in the embodiment of FIG. 4A). Similarly, projector 802B has a projection optical axis at a compound miter angle and projects sine-wave pattern 499B, wherein its lines of constant intensity are at a 45-degree angle $\beta_B$ to the direction of scanning 90, and at a 90-degree angle to the lines of constant intensity of sine-wave pattern 499A. Beamsplitter cube 820 is used to allow imaging of pattern 499A onto detector 423A, and to allow imaging of pattern 499B onto detector 423B.

In this embodiment, the optical axis of sensor 804 is a right angles to the direction of scanning 90 (the Y direction), however the long axis of each detector array 423 is at a 45-degree angle to the direction of scanning 90, and each point of device 99 is measured at Y1 at a first point in time, at Y2 at a second point in time, and at Y3 at a third point in time. (For example, when a 3-by-2048 trilinear detector 423 having an eight-pixel spacing between lines is used, the 50th pixel of the first line, the 58th pixel of the second line, and the 66th pixel of the third line are used for the first, second and third measurement respectively of each point 50/2048ths of the way across the scan path, and a corresponding pixel of each of the three lines gathers information for the other points of the scan.)

As described in more detail above, in one embodiment projector 802A and projector 802B are strobed alternately (i.e., flashes of light from each projector are interleaved) (one strobe for each triple scan-line operation), and sensor 804 having detectors 423A (synchronized to projector 802A) and 423B (synchronized to projector 802B) is used to gather the image information. This reduces the area that is shadowed. In one such embodiment, sensor 604 is at a 90-degree angle to the Y dimension, projector 802A is at a 45-degree angle vertically and a 45-degree angle horizontally, and projector 802B is at a 45-degree angle vertically and a 45-degree angle horizontally (i.e., at a 45-degree angle on the other side).

In another such embodiment, a complete scan in the +Y direction, for example, with only projector 802A providing illumination, would be followed by a complete scan in the −Y direction, for example, with only projector 802B providing illumination. Thus features that were shadowed during one scan would be illuminated during the other scan. In such an embodiment, an incandescent (non-strobed) or strobable light source is used for each projector.

In yet another embodiment, the light from projector 802A is filtered or from a monochromatic light source (e.g., red color), and is at-a different color (frequency) than the light from projector 802B which is filtered or from a monochromatic light source at a different color (e.g., blue light). In this embodiment, sensor 804 is provided with a color separator (e.g., a dichromatic beam splitter 820), and one trilinear detector 423 for each color. (See FIGS. 9A, 9B, and 9C below for further description.)

In still another embodiment, the light from projector 802A is polarized, and is at a different polarization than the light from projector 802B which is also polarized. In this embodiment, sensor 804 is provided with a polarization separator (e.g., a polarized beam splitter 820), and one trilinear detector 423 for each polarization.

In one embodiment, gantry 610 (not shown to scale) is used to scan head 801 in the Y direction during measurement, but is also used to move head 601 in the X direction for successive scan operations, and to move head 601 in the Z direction to adjust for thicker or thinner devices, for example.

FIG. 9A shows an isometric view of sensor 904A having a beamsplitter 820A such as is used in one embodiment of system 400A of FIG. 4A. In this embodiment, trilinear detector 423A is superimposed optically onto trilinear detector 423A (i.e., corresponding pixels of each trilinear detector receive light from identical points of device 99). In one such embodiment, the direction of scanning (the Y dimension) is diagonally across the top face 821 of beamsplitter 820, and thus at a right angle to the long axis of detector 423A. This provides an image that also moves at a right angle to the long axis of detector 423B.

Two Discrete Imagers (Dichroic Beam Splitter) Interleaved or Simultaneous

In one such embodiment, the trilinear detectors 423A and 423B are clocked so that they provide interleaved line images, thus providing a doubling of the speed achievable when imaging is otherwise limited by the clock speed of a single trilinear array detector. By aligning the two detectors with one another, and interleaving their respective acquisition of line-scan data, every other scan line (e.g., the even numbered lines) comes from detector 423A, while the other lines (e.g., the odd numbered lines) comes from detector 423B. In one such embodiment, the projector light source 402 is strobed, in order to reduce smearing of the image (i.e., capturing data from an region that is extended in the Y dimension due to the increased scanning speed).

Two Discrete Interleaved Imagers (50—50 Beam Splitter)

In one such embodiment, beamsplitter 820 provides a 50%—50% beam splitting function, thus providing equal illumination on trilinear detectors 423A and 423B. In one such embodiment, projector 404 is strobed at a different intensity for trilinear detector 423A than for trilinear detector 423B, in order to achieve an improved light-intensity dynamic range (i.e., a dimly lighted view and a brightly lighted view of the same device). This is because highly reflective points on device 99 can saturate the detector with a given illumination, while slightly reflective points will be too dark. By providing high illumination on one strobe, the dim points are accurately imaged, and low illumination on the interleaved strobe, the bright points are accurately imaged. In another such embodiment, the time for which trilinear detector 423A collects light is kept shorter ("shuttered" to a faster time) than for trilinear detector 423B, in order to achieve the same results.

In another such embodiment, beamsplitter 820 provides a variable-intensity (e.g., a 20%–80%) beam-splitting function. This provides an improved light-intensity dynamic range (i.e., a dimly lighted view and a brightly lighted view of the same points) such that, e.g., trilinear detector 423A can receive four times as much light during a given time period than does trilinear detector 423B (as well as perhaps achieving a speed improvement).

In still another embodiment, beamsplitter 820 provides a variable-color (e.g., a dichroic beamsplitter such as a red-blue color separating) beam-splitting function. In one such system, (such as system 600 of FIG. 6), one projector (e.g., projector 602A) projects a sine-wave striped pattern of red light, and the other projector (e.g., projector 602B) projects a sine-wave striped pattern of blue light onto the same region of device 99. (Were the same color projected simultaneously, the two patterns might interfere with each other's measurement operations.) The dichroic beamsplitter 820A separates the pattern from projector 602A from that of projector 602B allowing simultaneous measurements to the different colors by separate detectors 423A and 423B.

In yet other embodiments, a beamsplitter that provides three or more separations (e.g., one that provides splitting of three or more colors, or three or more intensities, etc.) is used, with a separate detector 423 for each light path provided.

Two Interleaved Imagers (Perpendicular Pattern Projector, Imager at 45 Degrees)

FIG. 9B shows an isometric view of sensor 904B having a beamsplitter 820B such as is used in one embodiment of system 800 of FIG. 8. In this embodiment, the long axis of long axis of detector 423A is at a right angle to the long axis of detector 423B as viewed from optical axis 421. In this embodiment, the direction of scanning (the Y dimension) is parallel to an edge (e.g., edge 822 of the top face 821 of beamsplitter 820B), and thus at a 45-degree angle to the long axis of detector 423A. This provides an image that also moves at a 45-degree angle to the long axis of detector 423B. As with FIG. 9A, this arrangement of positioning the trilinear detector 423 diagonally provides a more efficient use of beamsplitter material (e.g., a smaller cube can handle a given length trilinear detector 423. As with FIG. 9A, the trilinear detectors 423A and 423B are mounted next to the respective faces 821 and 823 of beamsplitter 820B, however, in other embodiments, the detectors are spaced away from the respective faces 821 and 823 of beamsplitter 820B.

FIG. 9C shows an isometric view of sensor 904C having a beamsplitter 820C. In this embodiment, the long axis of long axis of detector 423A is parallel to the long axis of detector 423B as viewed from optical axis 421, and both are substantially parallel to an edge 824 of the beamsplitter cube. In this embodiment, the direction of scanning (the Y dimension) is parallel to an edge (e.g., edge 822 of the top face 821 of beamsplitter 820B), and thus at a 90-degree angle to the long axis of detector 423A. This provides an image that also moves at a 90-degree angle to the long axis of detector 423B.

In variations of each of the embodiments of FIGS. 9A, 9B, and 9C, the splitting function can be done by any suitable combination of splitting material and arrangement, such as multiple dielectric layers, prisms, polarizers (Brewster's windows), etc. such as are well know in the art, and each are contemplated in different embodiments of the present invention.

Four Interleaved Imagers (2 Beam Splitters and Perpendicular Pattern Projector)

Further, various combinations are contemplated of the beam splitters of FIGS. 9A, 9B, and 9C with the systems 400, 600, 700, and 800 of FIGS. 4, 6, 7, and 8. For example, the sensor 804A and 804B of FIG. 8 are each implemented as sensor 904A in one embodiment, in order to acquire scan data with four interleaved sensors (thus acquiring data at up to four time the scan speed as is possible using a single sensor 404 and single projector 402.

Another aspect of the present invention provides a method for high speed, scanning phase measurement of a device at a machine-vision station to acquire physical information associated with the device. The method includes the steps of:

(1) projecting light generally along a projection optical axis 409, the projection optical axis intersecting the device;

(2) spatially modulating the light with a Moire pattern located so that the projection optical axis passes through the Moire pattern; and imaging the spatially modulated light onto the device; and (3) receiving light reflected from the device along a reception optical axis with an imager maintained in a substantially fixed relationship to the projected spatially modulated light, the imager including three lines of semiconductor imaging pixels, the reception optical axis intersecting the device;

(4) generating data representing acquired three-dimensional device geometry data regarding the device from signals from the imager;

(5) wherein the step of spatially modulating and the step of imaging the spatially modulated light provide a light pattern that is focused along a region of a third plane, wherein one of the three lines of semiconductor imaging pixels lies substantially within the third plane.

In one such embodiment, the step of spatially modulating and the step of imaging the spatially modulated light, and a third plane substantially satisfy Schiempflug's condition, and wherein the reception optical axis lies within the third plane or is substantially parallel to the third plane.

In another such embodiment, the step of spatially modulating provides a projected pattern whose intensity along a line segment varies as a sine wave.

Another such embodiment further includes the steps of:

(6) comparing the acquired three-dimensional device geometry data with an intended predetermined geometry to produce a signal indicative of any device geometry departure of an actual device geometry from the intended predetermined geometry; and (7) controlling a manufacturing operation of the device to compensate for said device geometry departure.

Telecentric Imaging

Another important aspect of the present invention provides telecentric imaging in imager 402. As above, machine-vision head 401 is provided for inspecting a device. In this embodiment, imager 402 includes a telecentric imaging element 420 that focusses an image of the device onto the three lines of semiconductor imaging pixels. A telecentric lens 420 provides an imaging system that provides increased accuracy of magnification across the width of the object and image field, particularly for imaging pixels that are radially displaced from the reception optical axis 421, i.e., displaced in the X dimension for FIG. 4A. In particular, the combination of substantially satisfying Schiempflug's condition (for the plane 413 of the pattern element 412, the plane 411 of the projection imaging element 412, and the plane 451 which extends in the Z dimension at the object or device being imaged 99 and containing optical axis 421 and the centerline axis of the trilinear array 423) in order to create a light pattern that is highly accurate in the Z-dimension, and the use of a telecentric imaging lens for lens 420 which provides increased accuracy across the field of view, provides greatly improved accuracy of three-dimensional data derived from the imaging operation. In various embodiments described elsewhere in this description, a telecentric imaging element is used for imager imaging element 420. In some embodiments, a hologram 432 (see FIG. 4D) providing imaging function equivalent to a telecentric lens is provided for imager imaging element 420. According to the present invention, telecentric imaging provides the advantage of maintaining better accuracy of magnification and sharper focus of features on device 99 that vary in height (i.e., the Z-dimension), particularly for features displaced from the reception optical axis 421 in the X dimension (i.e., features that will be imaged onto pixels displaced from the center of the three imaging lines of trilinear array 423.) This provides a better accuracy of height measurements at the sides (i.e., portions displaced from the optical axis in the X dimension; see FIG. 4A) of a scan.

Telecentric Projecting

Another aspect of the present invention provides telecentric projecting in pattern projector 402. As above, machine-vision head 401 is provided for inspecting a device. In this embodiment, imager 404 includes a telecentric imaging element 410 that focusses an image of the projection pattern element 412 onto the plane containing receiver optical axis 421 and the center line of the three lines of semiconductor imaging pixels. A telecentric lens used for pattern projector imaging element 410 provides an imaging system that provides increased depth of focus, particularly for device features that are radially displaced from the projection optical axis 409, i.e., displaced in the X dimension for FIG. 4A. In various embodiments described elsewhere in this description, a telecentric imaging element is used for pattern projector imaging element 410. In some embodiments, a hologram 430 (see FIG. 4D) providing imaging function equivalent to a telecentric lens is provided for pattern projector imaging element 410. According to the present invention, telecentric projecting provides the advantage of maintaining sharper focus of features on device 99 that vary in height (i.e., the Z-dimension), particularly for features displaced from the reception optical axis 421 in the X dimension (i.e., features that will be imaged onto pixels displaced from the center of the three imaging lines of trilinear array 423.) This provides a better accuracy of height measurements at the sides of a scan, as well as perhaps better Y-dimension measurements at the sides of the scan.

Color Filters, IR Blocking Filters, Monochromatic Light Sources

In one embodiment, a color filter 450 (see FIG. 4D) is placed between light source 418 and condensing imaging element 414, in order to sharpen the focus of light 498 and light pattern 499 (since it is easier and simpler to focus monochromatic light). In one embodiment, color filter 450 also blocks infra-red (IR) components of light 498, in order that these IR components do not get received by imaging pixels 422. In various embodiments, light source 418 is implemented as a halogen incandescent lamp, as a xenon flashtube, as a metal-halide arc lamp, as a laser, or as an array of LEDs (light-emitting diodes). In embodiments having substantially monochromatic light output, such as LED arrays, the need for a color filter is reduced. However, in some such embodiments, LEDs can still have substantial infrared components to their color spectrums, and in some such embodiments, an IR blocking filter is used for filter 450, in order to reduce the IR components of the light output 498. When single-frequency coherent sources such as lasers are used for light source 418, the need for color filters is generally eliminated.

In other embodiments, a color filter 452 is used, and is placed in the optical path of imager 404. In some embodiments, color filter 452 includes an IR-blocking function to block IR components of the received light. In some such embodiments, color filter 452 helps to remove unwanted ambient light, including IR components thereof.

Masks to Constrain Projected and/or Observed Illumination

In some embodiments, a mask 440 (see FIG. 4A) is used to block unwanted and stray light coming from sources other that the region of device 99 that is intended to be imaged onto trilinear array 423. In one such embodiment, mask 440 is painted or coated with a flat black surface, and has a slit aperture 441 extending in the X dimension, but narrow in the Y dimension. In one embodiment, slit 441 is configured with sharp (e.g., knife) edges to reduce reflections of the edges of the slit. Slit aperture 441 is configured to block light from those projected lines that fall to the sides (e.g., to the left or the right of reception optical axis 421 in FIG. 4A). Mask 440 is also configured so as to not block any of the Moire-type stripes or lines that extend in the Z dimension. This is because the light of interest can extend for a large number of Moire fringes in the Z dimension in order to obtain height information, and for a considerable distance on either side of the reception optical axis 421, in order that a wide region can be scanned in a single sweep, but the light of interest in constrained to only the angle in the Y dimension that will properly image onto the three lines of the trilinear array 423. Thus all light in the Y-dimension that falls outside this narrow angle can and should be masked or blocked.

In general, a narrow aperture mask is not called for to block projected pattern 499 since as many stripes in the vertical (Z dimension) as possible are desired to obtain height information for an extended range, however in some embodiments a mask 442 having an aperture 443 is used to reduce stray light from pattern projector 402, and in particular, to reduce specular reflections on the solder ball being measured of light reflected off surrounding balls (i.e., the mirror-like surface of the ball being measured will generally reflect the images of all surrounding balls, and by limiting the light that is projected on those surrounding balls, the unwanted reflections from those balls are minimized). In such embodiments, an aperture is configured having a length and width to accommodate the desired width and height of the measurement desired.

In other embodiments, the entire system 400 is enclosed in a light-blocking enclosure or shroud 445 to block out substantially all ambient light, and thus maximize signal-to-noise ratios of the acquired image data.

Sine-Wave Moire Pattern for Better Linearity and More Accurate Results

In some embodiments, a projection pattern element 412 having a sine-wave profile is used (i.e., the stripes that extend in the X dimension with a substantially constant density, vary as a sine wave in the direction towards line 419A, See FIG. 4A). In various exemplary embodiments, the stripes have a pitch of three to ten stripes per millimeter. Sine-wave stripes give better linearity and more accurate results in some embodiments.

In other embodiments, a projection pattern element 412' having a sine-wave profile is used (i.e., the stripes that extend in the X dimension with a substantially constant density, vary as a square wave in the direction towards line 429, See FIG. 4D). In various exemplary embodiments, the stripes have a pitch of three to ten stripes per millimeter. Embodiments having square wave stripes can provide good results particularly at finer pitches, since the projected pattern will focus to a pattern that has substantially a sine-wave profile at reception optical axis 421.

Offset Slit Pattern to Generate Sine Moire Pattern

In one embodiment of the present invention provides two striped patterns, wherein the plane of one set of stripes is parallel to and offset from the plane of the other set of stripes. In one such embodiment, the two striped patterns are square-wave, parallel opaque stripes that are on either side of a transparent separator. In one such embodiment, no projection imaging element 410 is used, since the resulting light pattern provides the desired sine-wave pattern at the measurement plane (the region near and at the device 99 of the plane that includes reception optical axis 412 and the center line of the trilinear array 423).

Modular Machine Vision System

Figure 10:
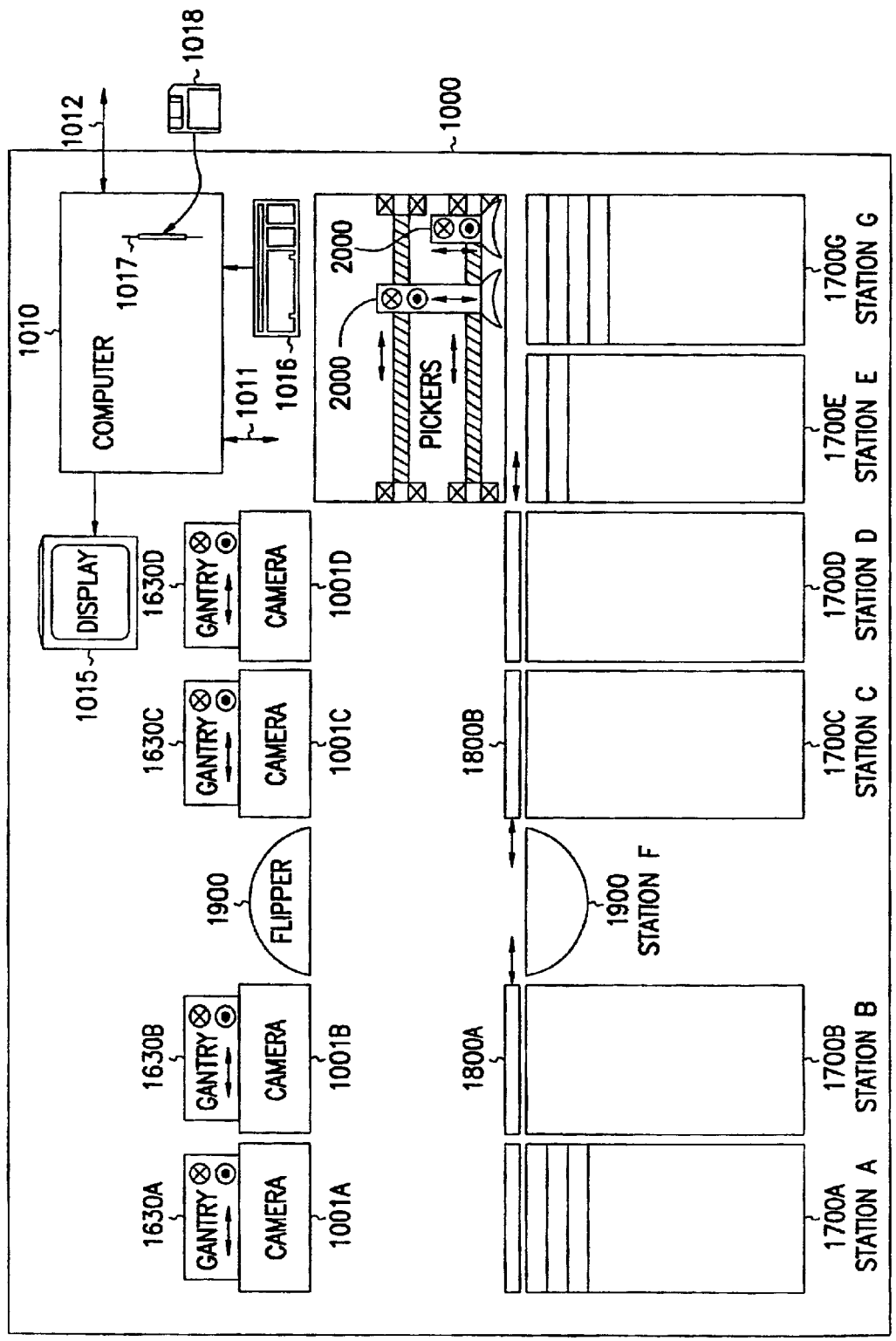
FIG. 10 shows a modular machine-vision system 1000 of one embodiment of the present invention.

FIG. 10 shows a modular machine-vision system 1000 of one embodiment of the present invention. In the embodiment shown, two cameras 1001A and 1001B are 2D and 3D inspection cameras respectively, and acquire 2D and 3D of the, for example, bottom surfaces of devices 99 in trays. Gantry 1630A and gantry 1630B are controlled by computer 1010, and provide the scanning motion for cameras 1001A and 1001B. In one such embodiment, camera 1001A is a 3D inspection camera such as head 401 of FIG. 4A, and camera 1001B is a conventional raster scan CCD imaging camera with a strobed ring-light illumination. Gantry 1630C and gantry 1630D are controlled by computer 1010, and provide the scanning motion for cameras 1001C and 1001D. These separate gantries provide independent scanning motions as may be needed for the 2D and 3D cameras, which may require different scanning speeds or x-y motions. In other embodiments, a single gantry 1630 is used to control both cameras 1001A and 1001B, and/or a single gantry 1630 is used to control both cameras 1001C and 1001D, in situations where a common motion to scan both cameras can be used. Elevators 1700A and/or 1700B are used to input trays of parts into system 1000 for inspection. Conveyor 1800A is used to hold trays stationary for inspection under cameras 1001A and 1001B, and to move trays from inspection station A to inspection station B to flipping station F. Conveyor 1800B is used to move trays from flipping station F to inspection station C to inspection station D to picking station E and picking station G, and to hold trays stationary for inspection under cameras 1001C and 1001D. One or more pickers 2000 are used to select devices from trays and to fill trays having all-good parts for output at elevator 1700G of station G, for example.

Computer 1010 for this embodiment includes keyboard input device 1016, display output device 1015, program media I/O device 1017 (e.g., a diskette drive), I/O signals 1011 used to control and receive input from the other components of system 1000, and I/O signals 1012 (e.g., a local-area-network) used to control other steps in the manufacturing process and/or send and receive data useful for the manufacturing process or its control or monitoring. In one embodiment, program media 1018 and/or network signals 1012 are used to input control programs to computer 1010.

In other embodiments, the functions of the stations described above are combined or eliminated to provide a lower-cost system. In one such embodiment, stations A, D, E, and G are eliminated, a single input elevator (e.g., 1700B) is used, camera 1001B is a 2D/3D combined camera such as is shown in 401D of FIG. 4D, wherein alternated strobes of patterned light and non-patterned light are used to acquire 3D and 2D (respectively) line scan data Similarly, a single output elevator (e.g., 1700C) is used, camera 1001C is a 2D/3D combined camera such as is shown in 4011D of FIG. 4D. A flipper 2000 inverts the devices between station B and C. One picker 2000 is used at station C to remove defective devices.

In yet other embodiments, stations A, B, and C have elevators 1700 that are used to input trays of parts to be inspected; and stations D, E, and G have elevators 1700 that are used to output trays of inspected parts. Conveyor 1800A moves trays from any of the three input elevators 1700 to stations A and B for inspection (trays from elevator 1700C are transferred from conveyor 1800B to conveyor 1800A at station F. Conveyor 1800B transfers trays from/between the flipper, inspection stations C and D, and picker stations E and G. Each of the six elevators 1700 are used to queue parts that have been loaded and are waiting to be inspected, or parts that have been inspected and are waiting to be unloaded. The loading and unloading of the elevators is performed by human users in one embodiment, and is performed by automated robots in other embodiments.

In still another embodiment, the elevators 1700 of FIG. 10 are eliminated, and trays of devices (or in other embodiments, devices in other containers, or devices attached to film strips, or even devices naked on a conveyor to be inspected) enter the system 1000 from the left on a conveyor from the last manufacturing process. The trays then pass sideways though one or more of the inspection stations A, B, C, and/or D, the flipper station F, and/or the pick-and-place stations E and/or G. In one such embodiment, the trays then pass to some other operation, such as packaging, assembly, or shipping, out the right side of system 1000. Such inspection is sometimes called "in-line inspection."

One important aspect of the present invention is to reduce the time needed to move trays of parts. To accomplish this, trays are preferably moved along their shortest edge (i.e., the long edge of the trays are next to one another, and the trays are moved in the direction perpendicular to this). Further, each station is as narrow as possible and as close as possible to it neighbor stations, i.e., the elevators 1700 and cameras 1001 have narrow edges and are mounted as close as possible to one another, to minimize the distance between stations. The cameras 1001 are scanned along the long dimension of the trays, to minimize the number of times the camera is stopped and moved to the next scan path. Further, inspection starts on top of the first input elevator, so that the trays need not be moved sideways from the first elevator to the first inspection station which would take extra time.

Figure 11:
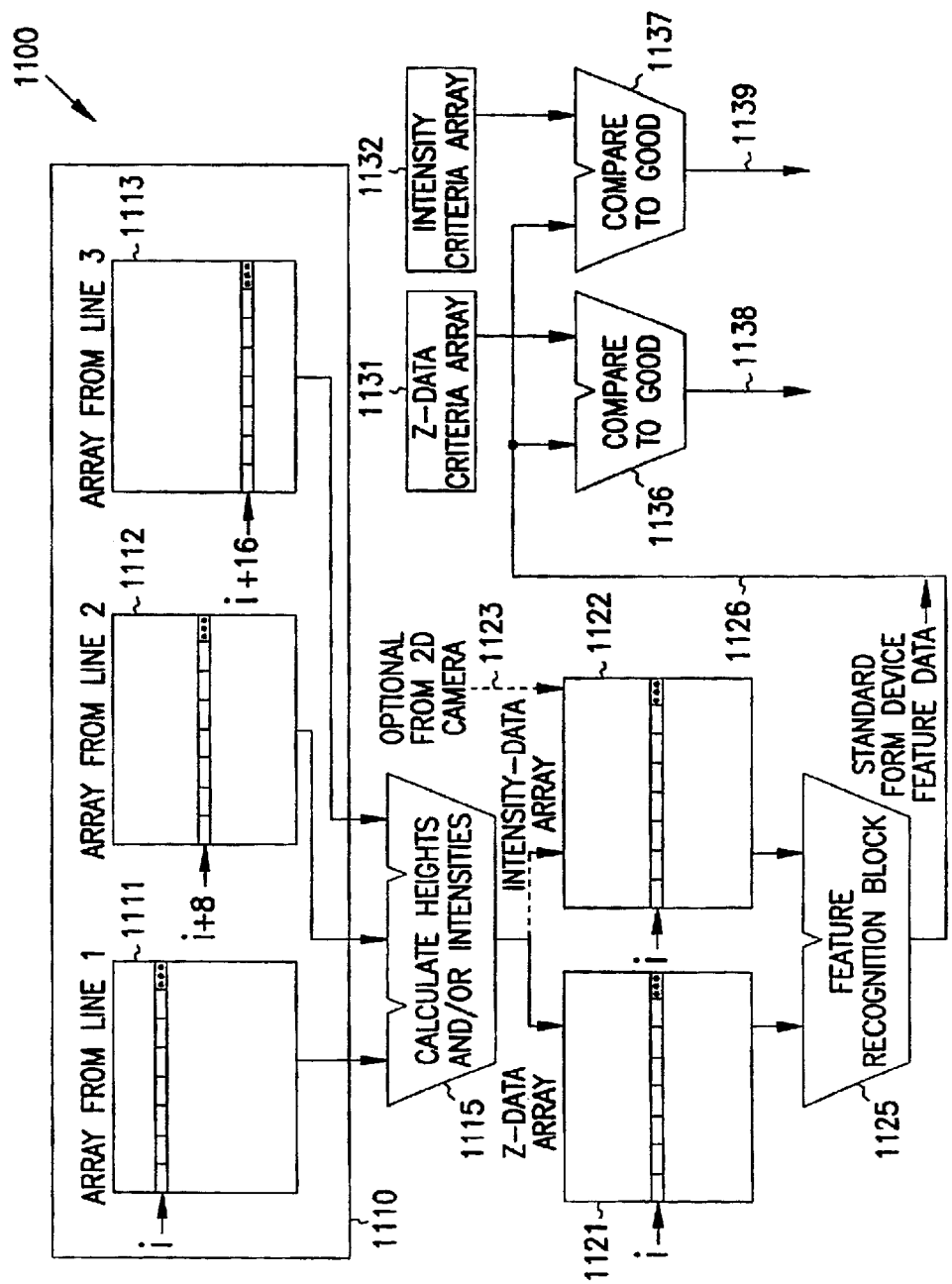
FIG. 11 shows a computation and comparison system 1100 of one embodiment of the present invention.

FIG. 11 shows a computation and comparison system 1100 of one embodiment of the present invention. In one embodiment, computation and comparison system 1100 is implemented as a software program and data structure that operates in computer 1010 of FIG. 10. Scan data from trilinear line-scan detector 423 is loaded into array 1110, with successive lines of digital data values from the first line going into subarray 1111, data from the second line going into subarray 1112, and data from the third line going into subarray 1113.

In one embodiment, a calculation is performed on a line-by-line basis to correct for intensity-level bias, drift or noise. For example, in one embodiment, one or more pixels, e.g., at the beginning of a scan line, are kept in the dark (i.e., unilluminated by any image of the device 99) in order to detect a bias or drift in the value associated with "black." This black-value bias is then subtracted from each data value for the line.

In one embodiment, the trilinear array 423 has three lines of 2048 pixels each, with a pixel-to-pixel distance of 14 microns and a line-to-line distance of 112 microns (i.e., each photosite is square with a pixel-to-pixel center-to-center distance of 14 $\mu$m and the line-to-line center-to-center spacing is 112 $\mu$m or the equivalent of 8 pixels). The camera 1001 is moved by one pixel distance between scans (in one embodiment, the scan movement is perpendicular to the long axis of the lines; in another embodiment, it is at a 45-degree angle). Thus a particular point on device 99 will be measured by a particular pixel of line 1 of trilinear-array 423 going into subarray 111, then eight scans later that same particular point on device 99 will be measured by the corresponding pixel of line 2 of trilinear array 423, data from the second line going into subarray 1112, and then eight scans later that same particular point on device 99 will be measured by the corresponding pixel of line 3 of trilinear array 423 and data from the third line going into subarray 1113. Thus for a given Y value there are three lines of data representing light intensity of the intersection of the light pattern 499 with device 99: the index i points to the data in array 1111, the index i+8 points to the data in array 1112, and the index i+16 points to the data in array 1113.

Calculator 1115 derives height data which is placed into Z-data array 1121 and/or intensity values which are placed into intensity-data array 1122 (in another embodiment such as shown in FIG. 4D, intensity data 1123 is obtained from a 2D scan camera—for example the middle line 2 of the trilinear array 423 is scanned out after illumination strobe from non-patterned light source 403 (e.g., a ring light) that is interleaved with a strobed projector 404 that provides patterned light for 3D measurements).

Feature recognition block 1125 uses data from array 1121 and/or array 1122 to identify features of devices 99 in the refined data (such as edges of parts) and performs the necessary transformations (such as masking and rotations of an individual part's data) needed to convert the data into a standard form 126. This standard form data 126 is then passed to comparators 1136 and/or 1137 where the data are compared to the criteria for good data from z-data criteria array 1131 and/or intensity-data criteria array 1132. The outputs 1138 and/or 1139 respectively of comparators 1136 and 1137 are then optionally used to select good parts, discard bad parts, and/or provide feedback to adjust a manufacturing process to a desired state.

Since the present invention provides for acquiring height {z} data for every {x,y} point in the scanned region (in contrast to other systems which scan a single line down a row of pins, for example) the present invention allows for random orientation of parts in trays, without requiring registration, shaking of trays, or other operations to prepare the parts for inspection. Rather, parts may be in any orientation in the scanned field of view.

Further, the present invention provides for random location of features (rather than aligned parts in trays, use of pocket edges or the requirement of rows of features such as pins or balls). There is no requirement for regularity in the configuration of features to be-scanned (i.e., rows of pins). Indeed, even objects such as eggs or gemstones may be measured with great accuracy and speed. The present invention does not require features to be lined up in order to measure those features quickly. In contrast, other systems which, for example use laser triangulation, benefit from arranging parts, such that all the pins to be inspected are aligned with the line that the laser scanning beam is directed. The present invention handles irregular spacing of features such as are found on chip-on-module and hybrid packages, which often lack regular spacings of features such as pins in a row.

In some embodiments of the present invention, crossed pattern projectors (such as shown in FIG. 6 and FIG. 8) are used for shadow reduction, i.e., a second projector provides measurements for areas that are in a shadow relative to the first projector.

In some embodiments, position or velocity detection is provided. In one such embodiment, a high-resolution linear position encoder is used to specify the times at which line scans are taken, (in one such embodiment, fiduciary stripes are applied to the field being scanned, such as to the edge of the clamp holding the tray of devices 99). For example, the start of the electronic "shutter" for each line scan is synchronized to a position. The scan timings thus are directly related to position rather than velocity, and thus make the measurement accuracy velocity-independent. In one such embodiment, however, the scanning velocity is maintained at a constant velocity, in order that a fixed shutter duration obtains the same amount of light. In another such embodiment, both the start and stop timings of the shutter are synchronized to position (e.g., using a linear position encoder). In yet other embodiments, the shutter duration is adjusted by a servo circuit that detects the instantaneous or short-term integrated light output of the light source 402, in order to achieve greater accuracy, as described further below.

In some embodiments, the present invention provides detection of substrate warpage as well as ball top coplanarity. Since all {x,y} points are measured for z height, a measurement of the substrate planarity or warpage is provided by the same scan that provides an indication of ball-top coplanarity. In some such embodiments, two different measurements are made in the same scan (such as described above, by varying the beam-split amount, or the projection strobe intensity, or the imager shutter time, the dim features, such as substrate details and planarity can be measured in interleaved scans with the high-brightness features such as shiny solder balls). In some embodiments, two discrete apertures (lamp brightnesses, shutter durations, or flash lengths) interleaved (e.g., a long aperture for dark portions or features, and a short aperture for bright or shiny features; e.g., one brightness for ball tops, another for substrate warp) are used.

Figure 12:
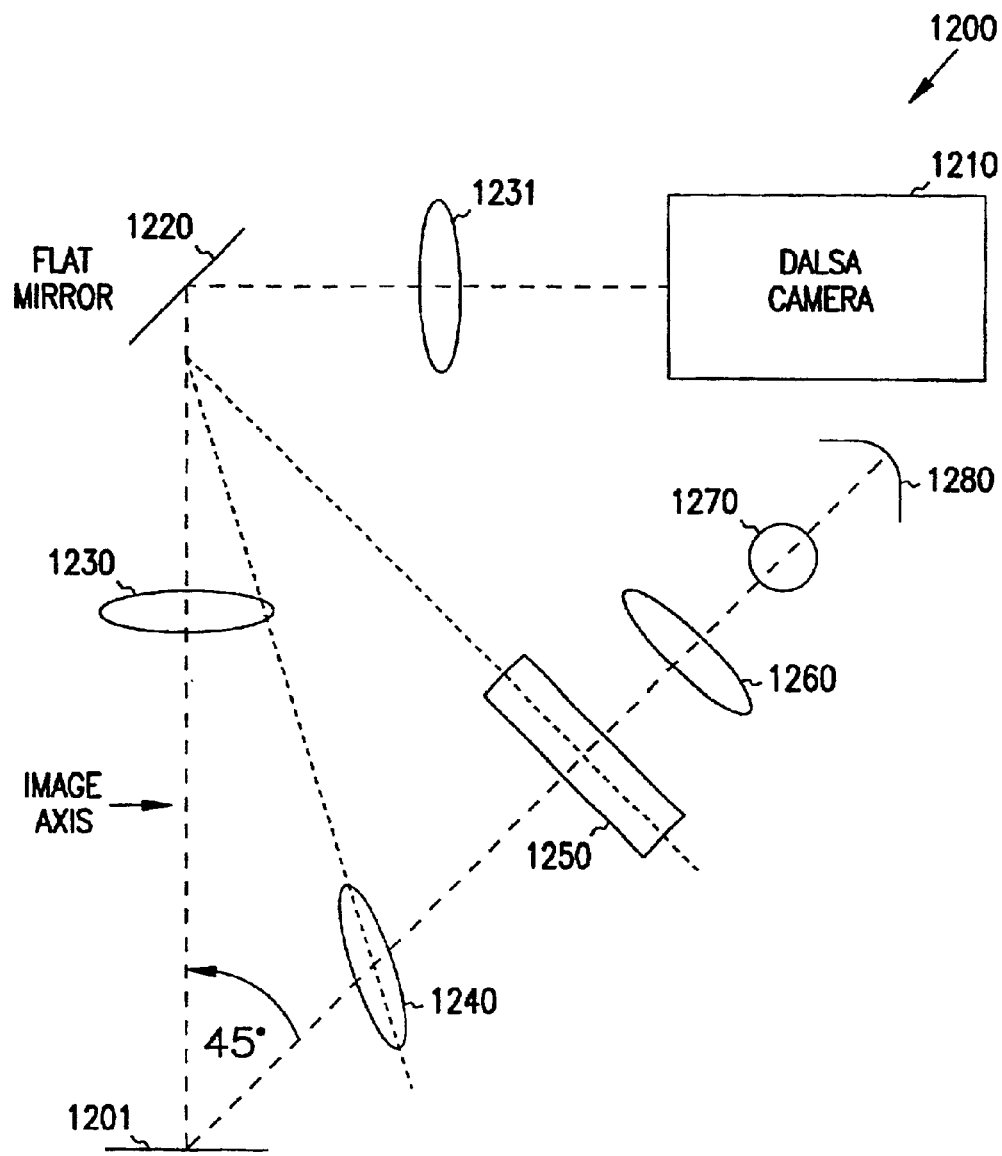
FIG. 12 is a schematic layout of another preferred embodiment of the vision system.

FIG. 12 is a schematic layout of another preferred embodiment of the vision system 1200. The function of the layout is to project a sinewave pattern onto an object 1201 and to measure the reflected intensities with a tri-linear CCD without color filters. The vision system 1200 includes a Dalsa camera 1210, a flat mirror 1220, a telecentric lens pair 1230 and 1231, a projection lens 1240 a grating 1250, a condenser pair 1260, a filament 1270 and a spherical mirror 1280. The CCD used by the Dalsa camera 1210 is the Kodak KLI-2103 which contains 3 rows of 2098 active photosites. Each photo site measures 14 µm square and the center to center spacing between the rows is 112 µm or the equivalent of 8 pixels.

The field of view (FOV) of the telecentric lens 1230, 1231 is 2.25" which is wide enough to inspect two 27 mm parts (including a separation gap of 0.125"). This translates into a maximum average magnification of m=0.514. The minimum allowed average magnification is m=0.499 (3% decrease) and the allowed magnification variation along the central axis (for one lens) is ±0.5%, but is preferred to be less than ±0.2% (which is equivalent ±½ LSB of the range measurement). Compensation can be added to the range calculations to reduce the affect of magnification variation if the variation is greater than ±0.2%. The degree of telecentricity (that is, how parallel is the central axis of the apertures across the FOV) must not change more than 0.01° over an 8 mil position change in the object 1201 plane. The position distortion must not exceed ±1% of the FOV along the central axis. Ideally the position distortion should be less than ±0.1%, but this can be obtained by software compensation if the lens is unable to provide it. The maximum aperture opening must be at least f5.6 and preferably f4.0. The aperture should be adjustable.

The grating 1250 is a sinusoidal line pattern. The grating 1250 is available from Sine Patterns LLC. The line pattern is oriented parallel to the 3 rows of the CCD. The frequency of the sinusoid and the magnification of the projection lens is chosen so that one cycle along the vertical imaging axis is 25.6 mils long to give a range resolution of 0.1 mils.

The projection lens 1240 magnification is chosen so that one cycle along the vertical imaging axis is 25.6 mils long. The maximum aperture must be at least f4.0 and possibly as large as f2.0. The-aperture is not required to be adjustable. The magnification change across the central axis must be ±0.5% or less and preferably less than ±0.2%. The axis of the lens is rotated to provide an extended depth of focus of the line pattern in the image axis. The rotation is such that the grating, image axis and projection lens axis tri-sect per the above drawing.

The condenser lens pair 1260 collects light from the filament and images the filament onto the aperture of the projection lens. The aperture size should be at least f1.0.

The filament 1260 is L7420 from Gilway Technical Lamp. The filament 1260 size is 11.8×4.6 mm and the power is 400 watts. Other filaments with a similar power rating can be substituted.

The spherical mirror 1270 has a radius equal to its distance from the filament. Its purpose is to reflect light to the condenser lens. Since the filament blocks the direct path, consideration can be given to creating a virtual image of the filament adjacent to the real filament.

A reflecting IR, filter (not shown in the above drawing) between the filament and the condenser lens is required because the CCD has a poor MTF response in the IR range and to reduce spherical aberrations in the optical path.

Focus adjustment must be provided so that the optimal focus of both optical paths occurs at the object.

Light Intensity Control

Figure 13A:
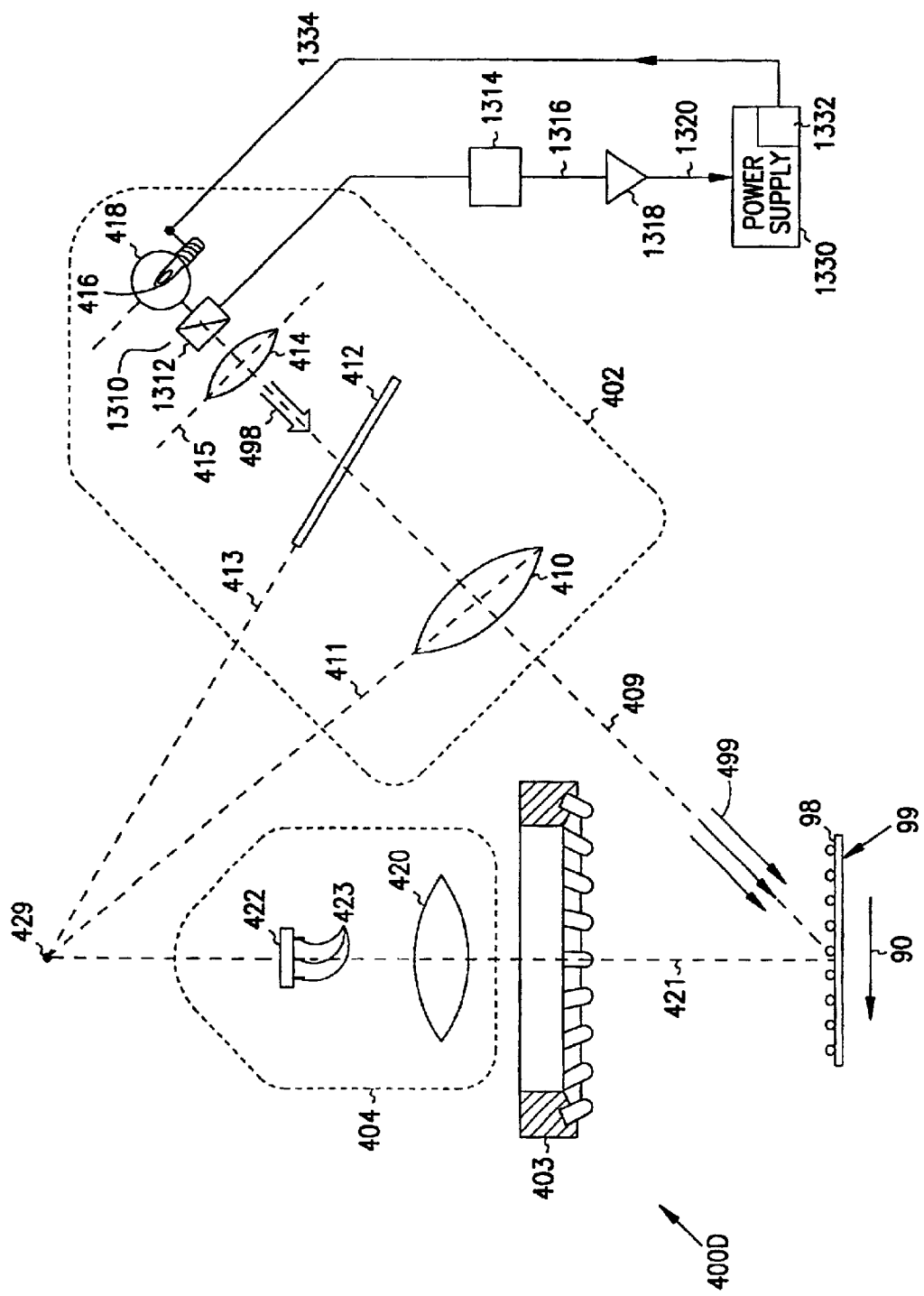
FIG. 13A is a schematic view of one preferred embodiment of a light intensity controller.

FIG. 13A is a schematic view of one embodiment of a light-intensity controller according to the present invention. Many of the elements of the projector 402 and the imaging system (or imager) 404 have been described above. For the sake of saving space, the description of the projector 402 and the imaging system 404 will not be repeated here. Rather, common numbers will be used to describe the elements needed. The machine-vision system 401 is for inspecting the device 99 which moves relative to the projector 402 and the imaging system 404. To obtain more accurate values when an image is acquired, the machine-vision system includes a light sensor assembly 1310 which receives light from the light source 418. The light sensor assembly 1310, as shown in FIG. 13, includes a beam splitter 1312 which splits off a portion of the light produced by the light source 418. The beam splitter allows a portion of the light from the light source to pass and reflects another portion of the light to a light sensor 1314. The beam splitter 1312 is positioned between the light source 418 and the device under test 99. Although the beam splitter 1312 could be positioned anywhere along the path between the light source 418 and the device under test 99, as shown in FIG. 13A, in this embodiment, the beam splitter 1312 is positioned between the light source 418' and the light source imaging element 414. The beam splitter 1312 also serves a second purpose in some embodiments: filtering out certain undesirable light such as infrared light or light of other wavelengths. In one such embodiment, beam splitter 1312 serves to pass only a narrow band of light frequencies (i.e., substantially monochromatic light), in order to facilitate focussing.

The light sensor 1314 is positioned to receive light from the beam splitter 1312. The light sensor 1314 is typically a photo diode which produces an output 1316 responsive to the intensity of the light received at the light sensor assembly 1310. It should be noted that in some embodiments, light sensor 1314 is used without the beam splitter 1312. In other words, in such embodiments, the light sensor is merely placed somewhere in the light from light source 418 to collect a portion of the light from the light source 418. In some such embodiments, the value of the output 1316 from the light sensor 1314 is higher if the light sensor 1314 is merely placed in the light path.

In this embodiment, the output 1316 is a signal that is used as part of a feedback control loop to control the intensity of the light, or the intensity of the light that will be received by imager 404. As shown in FIG. 13A, the output 1316 is input to an amplifier 1318 to produce an amplified output or control signal 1320. The machine-vision system also includes a power supply 1330 and related a power supply controller 1332. The power supply controller 1332 is, in one embodiment, an independent controller associated with the power supply or is, in another embodiment, part of another controller. In other words, the tasks of controlling the power supply can be assigned to another controller, such as a computer 128, that controls other various aspects of the machine-vision system. The value of the control signal 1320 indicates the intensity of the measured light from the light source 418. By controlling the power input to the light source 418, the intensity of the light produced by the light source is controlled. The power supply controller 1332 controls the amount of power delivered to the light source so that the light intensity is within a desired or selected range. The value of the control signal 1320 indicates the intensity of the light from the light source 418. When the value of the control signal 1320 falls below a specified value which is outside the selected or desired range, the controller 1332 increases the power input 1334 to the light source 418. This in turn increases the intensity of the light and the signal output from the light sensor 1314 and the control signal 1320. If the value of the control signal 1320 is above a specified value which is outside the selected or desired range, the controller 1332 decreases the power input 1334 to the light source 418. This in turn decreases the intensity of the light from the light source 418 and decreases both the signal output from the light sensor 1314 and the control signal 1320. In other such embodiments, control signal 1320 is used to control the length of time that light source 418 is "on," thus controlling the duration and/or shape of the light pulse output.

Figure 13B:
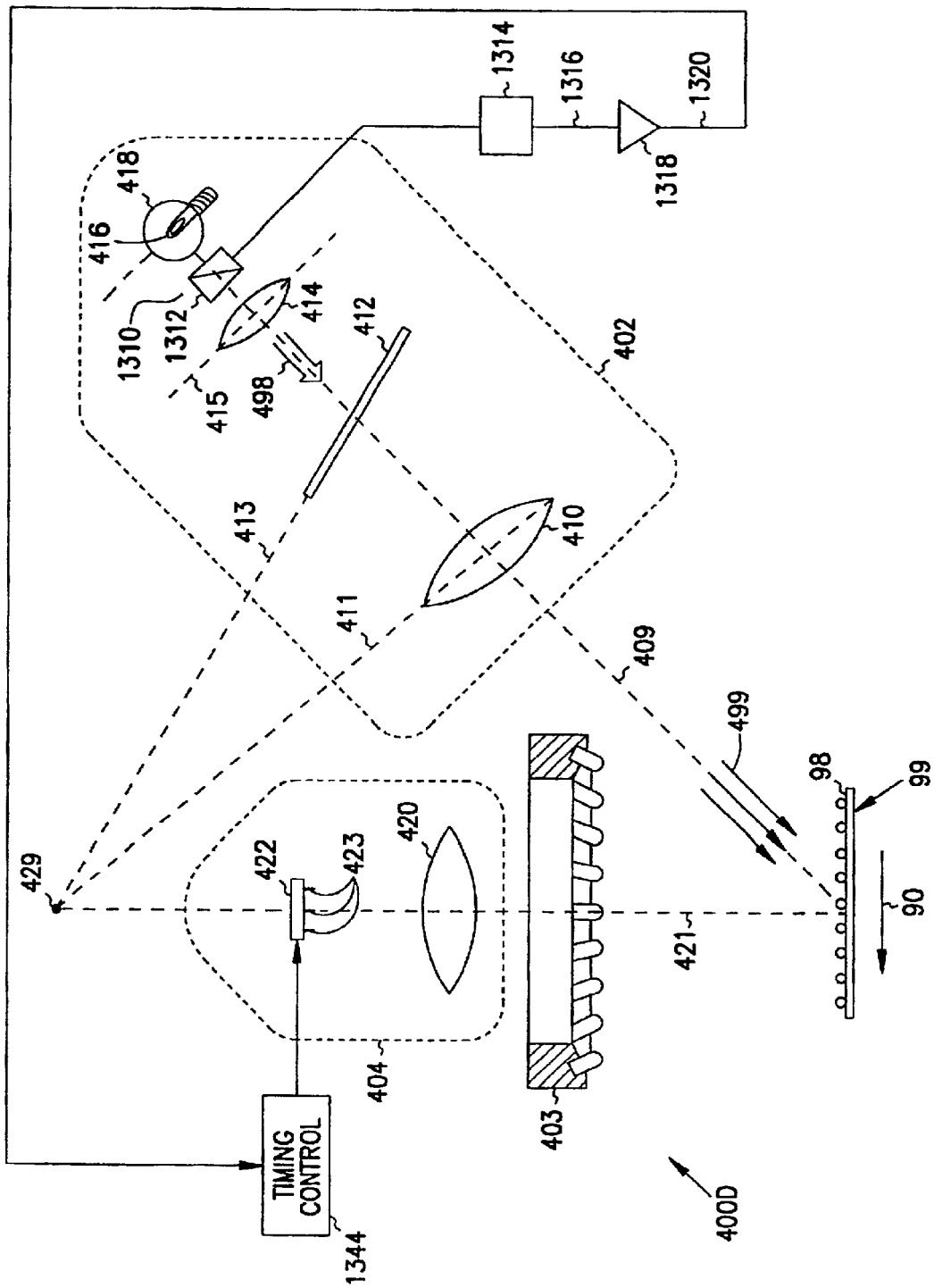
FIG. 13B is a schematic view of another preferred embodiment of a light intensity controller.

It should be noted that the are a number of ways contemplated by the present invention to control the intensity of the light from the light source 418 as received by imager 404. FIG. 13B shows a second preferred embodiment of this invention. The arrangement of most of the elements of FIG. 13B are the same as the arrangement of the elements in 13A. The difference is that the control signal 1320 from the light sensor 1314 and the amplifier 1318 is not used to control the light output from light source 1312, but rather in this second preferred embodiment, the control signal 1320 from the light sensor 1314 is used to control the length of time for image acquisition at the image detector 422, called "shuttering." In one embodiment, the image detector 422 includes three rows of pixels also known as a trilinear array 423. In the preferred embodiment, the trilinear array 423 is comprised of rows of semiconductor pixels or photo diodes which are part of a charge-coupled device, such as a high-speed digital CCD camera available as a KODAK KLI 2130 trilinear array.

The control signal 1320 from the light sensor 1314 is routed through a timing controller 1344 associated with the trilinear array 423 of the image detector 422. The trilinear array 423 is a charge-coupled device. In this particular charge-coupled device, photodiodes are the pixels. As the photodiodes are exposed to light, the charge on the associated charge-coupled device builds until the timing controller 1344 removes the charge at the end of an image acquisition. Thus, by controlling the amount of time the charge-coupled device is charged, the values of the charge-coupled device or intensity of the light acquired at the image detector 422 can be controlled. The value of the control signal 1320 indicates the intensity of the light from the light source 418. When the value of the control signal 1320 falls below a specified value which is outside the selected or desired range, the timing controller 1344 increases the length of the acquisition time at the image detector 422. This in turn increases the intensity of the light captured during the acquisition of the image at the image detector 422. If the value of the control signal 1320 is above a specified value which is outside the selected or desired range, the timing controller 1344 decreases the length of the acquisition time at the image detector 422. This in turn decreases the intensity of the light captured during the acquisition of the image at the image detector 422. As mentioned above the timing controller 1344 may be independent. More likely the timing controller 1344 is part of another controller associated with the machine-vision system.

Figure 13C:
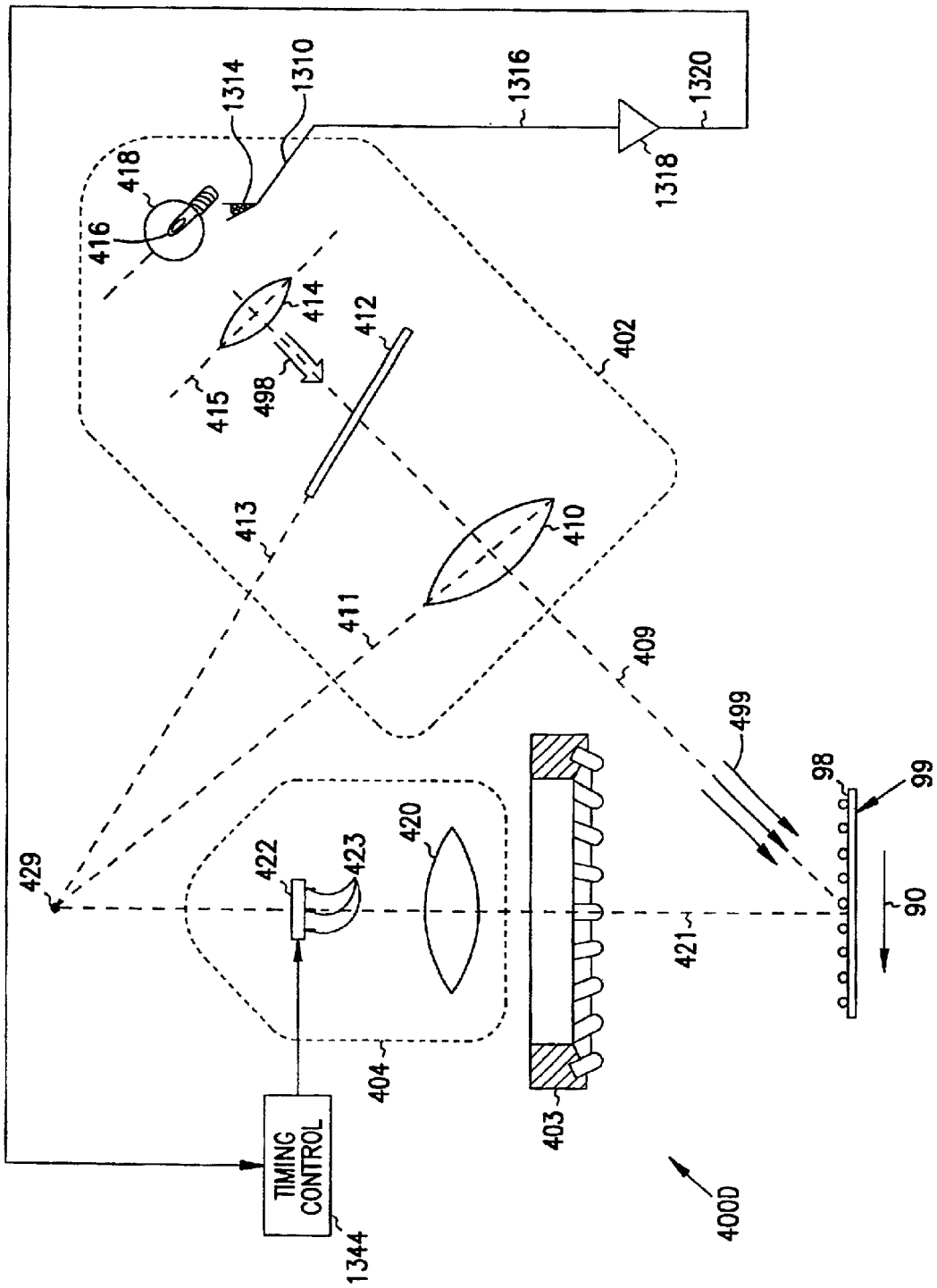
FIG. 13C is a schematic view of one preferred embodiment of a light intensity controller.

It should also be noted that the light sensor assembly 1310 in other embodiments is placed in the path of reflected light between the device-under-test 99 and the image detector 422. In addition, it should be noted that the light sensor 1314 need not be linked with a beam splitter 1312, as is shown in FIG. 13C. In FIG. 13C, the sensor 1314 is placed outside the path of the elements of the projector 402. In other words, the light sensor 1314 does not interfere with the light that is projected onto the device 99. The light source 418 sends light beams out in many radial directions. As a result, detecting the light outside the path of the elements of the projector 402 is often equally as effective as sensing the light within the path of projected light using a beam splitter (as shown in FIGS. 13A and 13B). Once sensed, the signal can be used to vary the power (similar to the embodiment shown in FIG. 13A) or can be used to vary the timing during acquisition of the image at the trilinear array 423 (similar to the embodiment shown in FIG. 13B). For the sake of illustration, a sensor 1314 of FIG. 13C is used to control the time of image acquisition.

In yet other embodiments, a sensor 1314 is used to control an aperture size, a shutter-open time, focus divergence, or a light-transmission density (or percentage) of an element (such as a liquid-crystal element) located in the light path between light source 418 and imaging element 422. Thus, in various embodiments, the control signal from sensor 1314 is used to control the light intensity of light source 418 (whether continuous or pulsed), the pulse length of light output by light source 418 (if pulsed), the light passed along the light path (whether varied by aperture, density, length-of-light-path (divergence) and/or shutter time), and/or the length of time for image acquisition of imaging element 422. In still other embodiments as described below, the control signal from sensor 1314 is used to control a calculated correction of the output signal from imaging element 422 (in one such embodiment, an analog adjustment is made to the analog output signal of imaging element 422; in another such embodiment, a digital calculation adjustment is made to the signal after it has been converted into a digital value).

Calculated Corrections

Figure 14A:
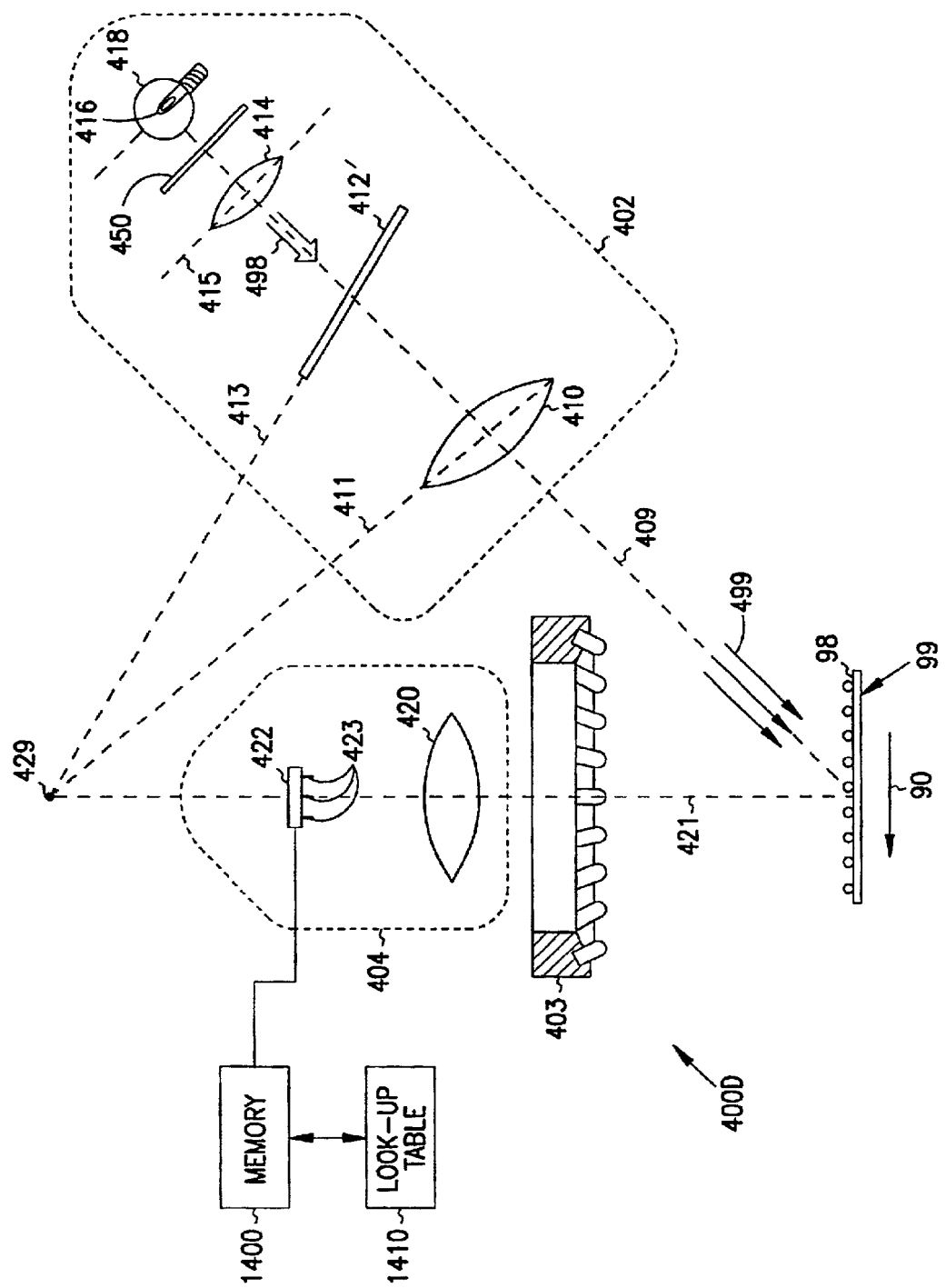
FIG. 14A is a schematic view of the imaging system having a memory device associated with the trilinear array.
Figure 14C:
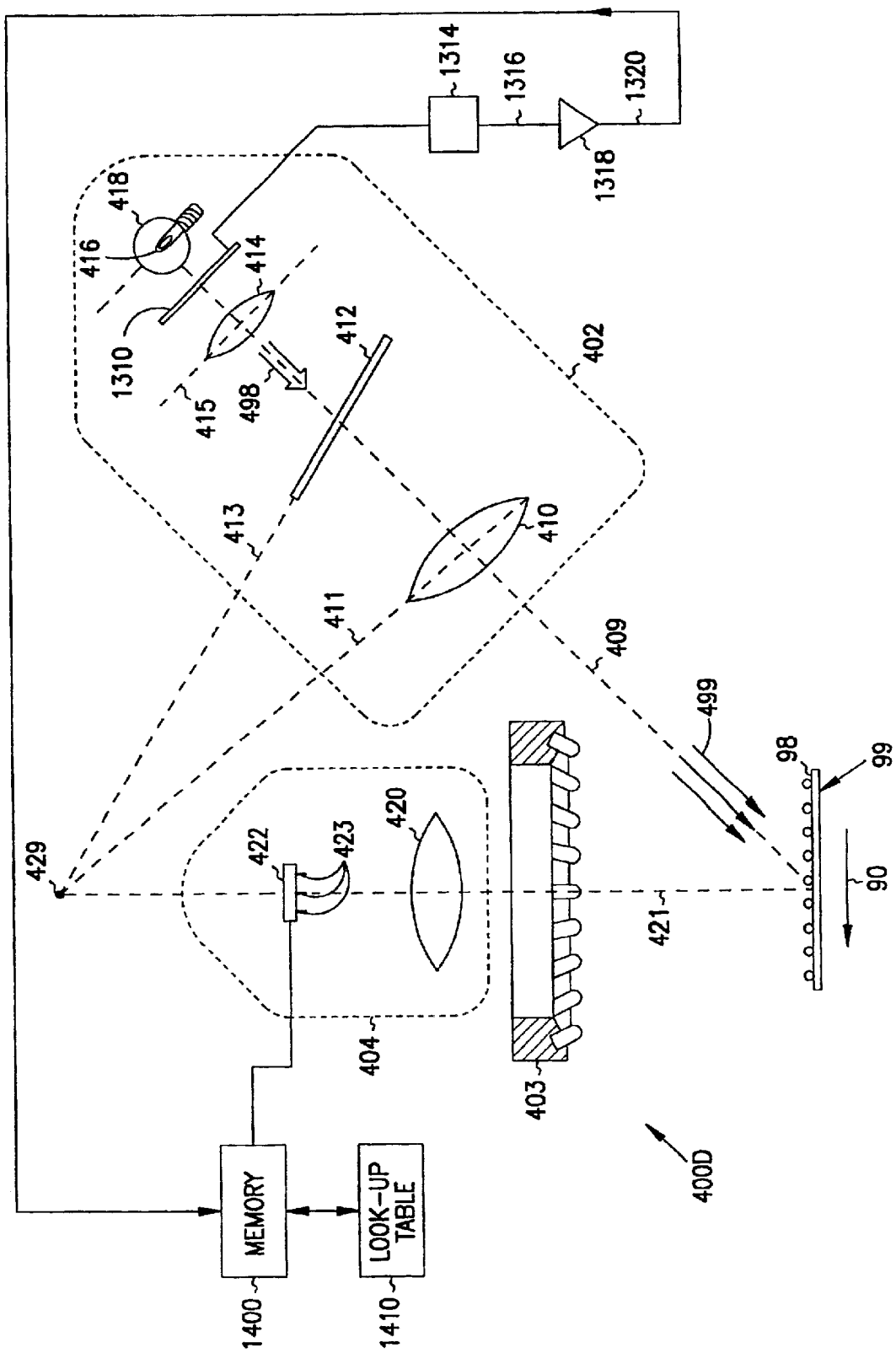
FIG. 14C is a schematic view of the imaging system having a memory device associated with the trilinear array in which a value associated with the intensity of the light is used to correct the values in memory.

FIG. 14A is a schematic view of the-imaging system 400 having a memory device 1400 associated with the trilinear array 423 of the image detector 422. As mentioned above, the photo diodes of the trilinear array 423 accumulate or discharge electrical charge to associated transistors during the time of acquisition. When the timing controller 1344 sends a timing signal, the electrical charge values associated with the transistors associated with each pixel are moved into the memory device 1400. Each of the pixels may have slightly different values in the presence of the same amount of light. There can be many reasons for this, including current bleeding from a nearby pixel or manufacturing tolerances associated with making the charge-coupled device. In one embodiment, the charge-coupled device associated with the image detector 422 is calibrated by exposing the pixels to an equal intensity light for a selected amount of time. The different values obtained are then stored in the memory device 1400.

From this stored information, a look-up table 1410, as shown in FIG. 14B, is constructed that contains correction values 1412 for each of the pixels and associated transistors of the trilinear array 422. Several calibration tests may be conducted to assure that the correction values 1412 are correct. The correction values may be multipliers used to multiply a particular value 1412 or may be a value 1412 which is added or subtracted from the value to obtain a proper value. Some values may contain both a multiplication component and an additive component. The table lookup 1410 is housed within memory and used to apply correction values to the values 1412 associated with the pixels of a trilinear array 423. In operation, the data from the pixels is acquired and placed in the memory device 1400. After acquisition, the correction value for the particular pixel is applied to the data in memory to calculate the corrected value for each pixel. These corrected values can be used and portray a more accurate image. One or more correction values can be stored in the table lookup 1410 for a particular pixel. In some instances, where the light source 418 is strobed with more than one intensities, there may be correction values associated with each light intensity for the particular light. Furthermore, if a different light is used, such as a ring light, there could also be still different correction values associated with each of these lights and the condition under which the lights are used. In summary, a table lookup can be constructed in which there are correction values for various lights used under various conditions.

Now turning to 14C, another way to correct for variations in intensity of the light can be accomplished using the arrangement shown. After the corrected values for each pixel in a trilinear array have been calculated, the control signal 1320 from a light sensor 1314 can be used to apply an overall correction value to the corrected values in memory 1410. Of course, the overall correction value could also be applied to the actual readings in memory 1410 initially and then the correction values from the table lookup could be applied. This would yield the same or an equivalent value to the method discussed previously in this paragraph.

Thermoelectric Cooling of the Image Detector

Figure 15:
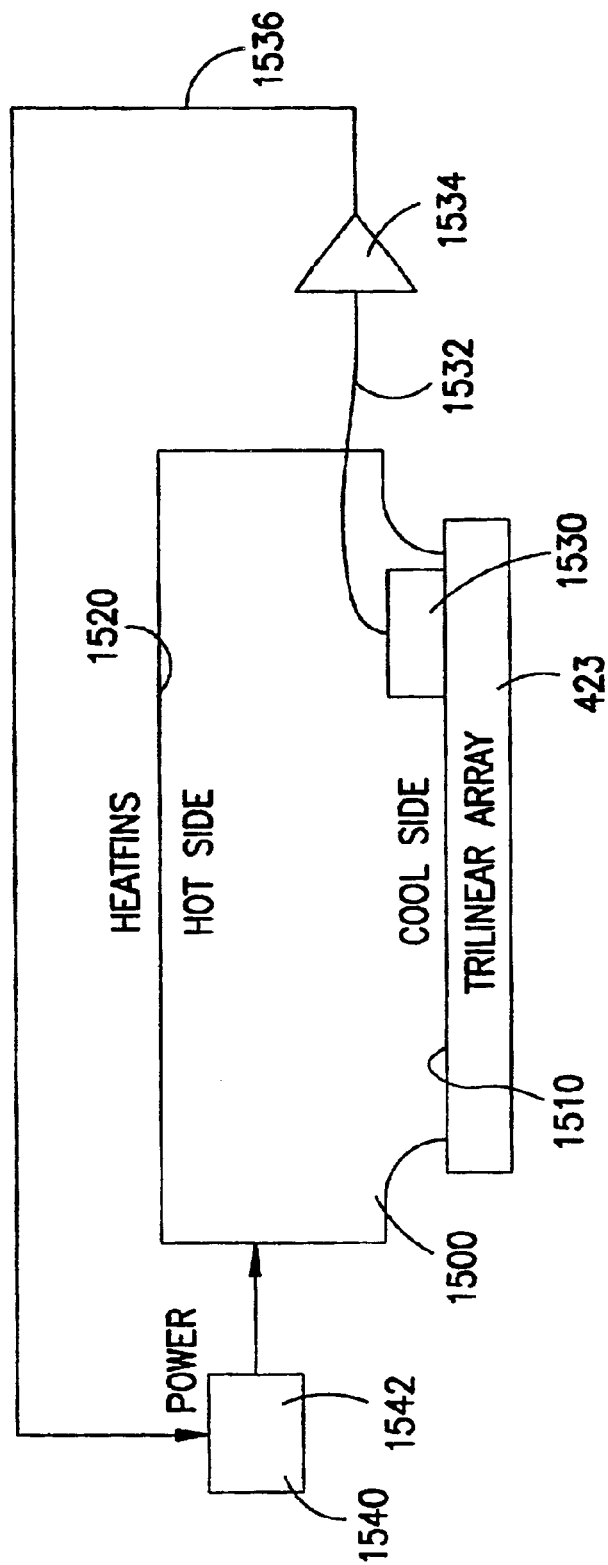
FIG. 15 is a schematic view of the trilinear array with a thermoelectric cooling element associated therewith.

FIG. 15 is a schematic view of the trilinear array 423 with a thermoelectric cooling element 1500 associated therewith. The thermal electric cooling element 1500 is attached to the trilinear array 423 using a thermal conductive adhesive. The thermal electric cooling element 1500 includes a cool side 1510 and a hot side 1520. The cool side of the thermal electric element 1500 is attached to the trilinear array 423. The thermal electric cooling element 1500 also includes a temperature sensor 1530. The temperature sensor 1530 outputs a signal 1532 which is amplified by amplifier 1534 to produce a control signal 1536. Control signal 1536 is fed back to a supply of power 1540. A power controller 1542 within the power supply 1540 decreases or increases the power supplied to the thermal electric cooling element 1500. By increasing the power input to the thermal electric cooling element 1500, the temperature along the cool side can be lowered, thereby lowering the temperature of the trilinear array 423. If too low a temperature is detected by temperature sensor 1530, the control signal 1536 will reflect that the amount of power input to the thermal electric cooling element 1500 must be lowered. The power controller 1542 can be within the power supply 1540 or can be part of another controller associated with the system.

It should be noted that the hot side of the thermal electric cooling element 1500 may be provided with heat fans or other elements used to increase convective or radiative cooling along the hot side 1520 of the thermal electric cooling element 1500. The basic operating principle of the thermal electric cooling element 1500 is the absorption or generation of heat as a current passes through a junction of two dissimilar metal materials. Electrons passing across the junction absorb or give up an amount of energy equal to the transport energy and the energy difference between the dissimilar materials' conduction bands. Cryogenic temperatures are reached using heat rejected from one thermal electric cooler stage to supply thermal input to the stage below. The basic operating principle of the thermal electric cooler is known as the Peltier Cooling Effect.

Advantageously, using thermoelectric cooling prevents the trilinear array 423 from heating up as they operate. As a result, the trilinear array 432 does not heat and the signals produced by the array 423 do not shift or vary, or only shift or vary slightly. This eases the task of correlating the data obtained and also prevents the current associated with a dark area, called dark currents, from rising into a range where the current becomes noise. This elimination or prevention of noise also simplifies processing of the image.

Strobing Lamps to Stop Motion Smear

Returning to FIG. 13A, strobing the light source 418 and strobing the ring light 403 will now be discussed. Strobing the light source 418 and strobing the ring light 403 substantially reduces or stops motion smear. Motion smear is similar to a blur in a photograph. In order to get a proper amount of light for charging the trilinear array 423 to a level where it produces useful data, a certain amount of light is needed. Without a strobe or high intensity, short burst of light, light must be gathered over a selected amount of time. As mentioned previously, the trilinear array 423 moves with respect to the devices 99 such that over the selected amount time so that enough light is provided to the trilinear array 423 for processing into useful data. When there is no burst of high intensity light, the device moves as the light is gathered from the device 99. The end result is that the data, when processed, produces a blurred image since the device 99 has moved appreciably over the time the necessary amount of light was produced.

To eliminate this blurring, which is also called motion smear, the light source 418 and the ring light 403 are "strobed." In other words, a circuit is used which produces a short burst of high intensity light. This shortens the amount of time over which the device 99 can move with respect to the light receiver or trilinear array 423 during image acquisition. This lessens or eliminates motion smear in the acquired image. In one embodiment, LED light sources are used in order to obtain a precise and repeatable amount of light, and the circuit used to strobe or pulse the light source is shown in FIG. 10 of U.S. Pat. No. 5,745,176. U.S. Pat. No. 5,745,176 and this patent application have a common assignee.

Mechanical Aspects of the Machine-Vision Station

Figure 16:
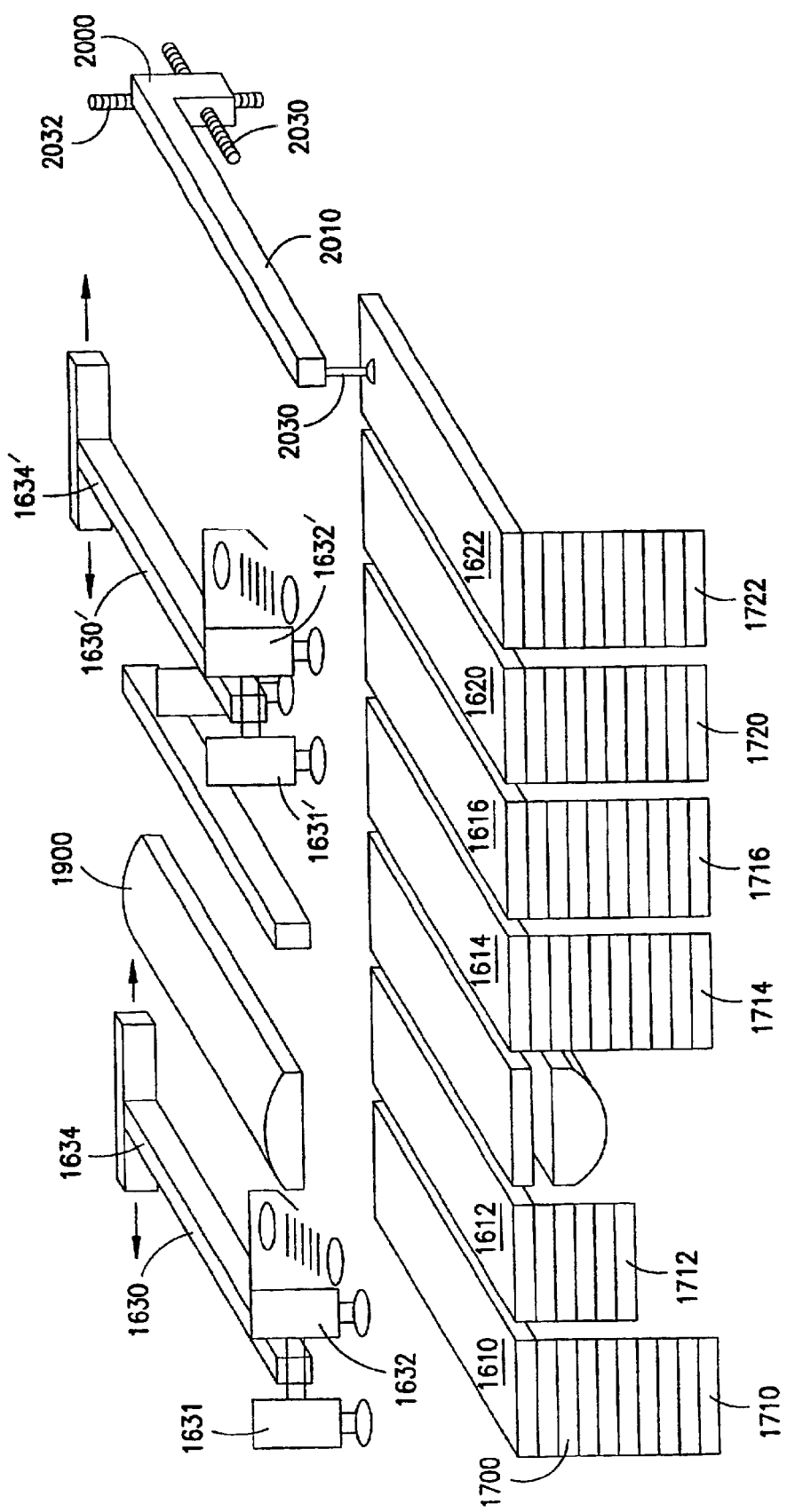
FIG. 16 is a perspective view of the machine-vision system.

FIG. 16 is a perspective view of the machine-vision system 1600. The machine-vision system 1600 includes a first inspection station 1610, a second inspection station 1612, a third inspection station 1614, a fourth inspection station 1616, a first pick-and-place station 1620, and a second pick-and-place station 1622. In this embodiment, pick-and-place operations are performed at two stations; in other embodiments, pick-and-place operations are not performed, or are performed at only one station, or are performed at more that two stations. Located between inspection station 1612 and inspection station 1614, is a tray inverter 1900. The tray inverter 1900 may also be called the flipper. A first gantry 1630 is located above inspection station 1610 and inspection station 1612.

In the embodiment shown, the first gantry 1630 includes a first inspection camera 1631 and a second inspection camera 1632. Each inspection camera 1631, 1632 is capable of acquiring a 3D image or a 2D image of the parts being inspected at the inspection stations 1610 and 1612 In various embodiments, cameras 1631, 1632 (or any of the inspection cameras at other inspection stations described herein) are implemented as one or more of the cameras described for FIGS. 3–13 above (i.e., each "camera" could be one 3D camera such as shown in FIG. 4A, or a 2D and a 3D camera such as shown in FIG. 13A). In yet other embodiments, each camera 1631 and camera 1632 is mounted on a separate, independently operable gantry in order to be separately movable to the locations and at the speeds best suited for each inspection operation. In some embodiments, each camera is implemented as a plurality of cameras operated in parallel to achieve even higher inspection speeds. For example, in one embodiment, camera 1631 is implemented as four heads 401 (as shown and described in FIG. 4A) mounted in a two-by-two square array, such that each head 401 need only acquire one fourth of the area to be scanned in a given period of time. In another embodiment, a 2D camera and a 3D camera are combined at a single inspection station (such as, for example, that shown in FIG. 4D), in order that information from the 2D inspection can be used to assist in the automatic computer-recognition of features to be analyzed in the 3D inspection.

In the embodiment shown in FIG. 16, the inspection cameras 1631, 1632 are mounted on a gantry arm 1634. The gantry arm 1634 is cantilevered over the inspection stations 1610 and 1612. The gantry arm 1634 includes a translation mechanism (not shown) which allows the first inspection camera 1631 to move along the length of the gantry arm 1634 and also allows the second inspection camera 1632 to move along the length of the gantry arm 1634, both under the control of a control computer such as computer 128 of FIG. 1 or computer 1010 of FIG. 10. In the preferred embodiment, the translation mechanism allows the first camera 1631 to move independently of the second camera 1632. In other words, the first inspection camera 1631 can move along the gantry arm 1634 at a first speed while the second inspection camera 1632 can translate along the gantry arm 1634 at a second speed. The inspection cameras 1631 and 1632 could also move in different directions along the gantry arm 1634. It is contemplated that one inspection camera 1631 could do a 3D-type inspection while the other inspection camera 1632 could do a 2D inspection. Generally, the cameras 1631 and 1632 move at different speeds when doing a 2D inspection or 3D inspection. Therefore, it is contemplated that while one of the cameras 1632 or 1631 is working in a 2D mode, the other of the cameras 1631 or 1632 could be simultaneously working in a 3D mode.

In one embodiment, the first inspection camera 1631 and the second inspection camera 1632 are spaced such that both inspection cameras 1631 and 1632 are positionable over a single station 1610 or 1612. As a result, in this embodiment, it is necessary to move the gantry 1632 from a position over the first inspection station to a position over the second inspection station 1612. A driving mechanism allows such movement and also allows for various positions for inspection where one of the cameras 1631 may be positioned over a first inspection station 1610 and the other of the cameras 1632 may be positioned over a second inspection station 1612.

In one embodiment, the devices being inspected with this particular machine-vision a system 1600 are semiconductor devices and, more particularly, semiconductor devices known as ball grid arrays (in other embodiments, leaded devices such as quad-flat-packs and/or DIP (dual-in-line) packages are inspected). Ball grid arrays are becoming increasingly popular semiconductor packages since the input/output pins are short and capable of being densely packed on a semiconductor package. In addition, the ball grid array is a rugged semiconductor package. Each device has a series of balls or solder balls positioned on one side of the semiconductor package. It is very important that these balls are uniform in shape and height. As a result, manufacturers go to great lengths to achieve this result. A number of individual semiconductor packages are carried in an industry-standard tray. One standard-formulating body is known as JEDEC and therefore one such type of industry-standard trays are known as JEDEC trays. When "JEDEC trays" are discussed in the embodiments below, it is to be understood that other embodiments are suitable for other types of trays and that other containers are used to hold the devices being inspected in various embodiments of the present invention. In still other embodiments, devices attached to a carrier strip (such as plastic film) are inspected. In yet other embodiments, the devices being inspected are not placed in any container, but are otherwise moved into place for inspection, for example, on a conveyor belt.

Figure 19A:
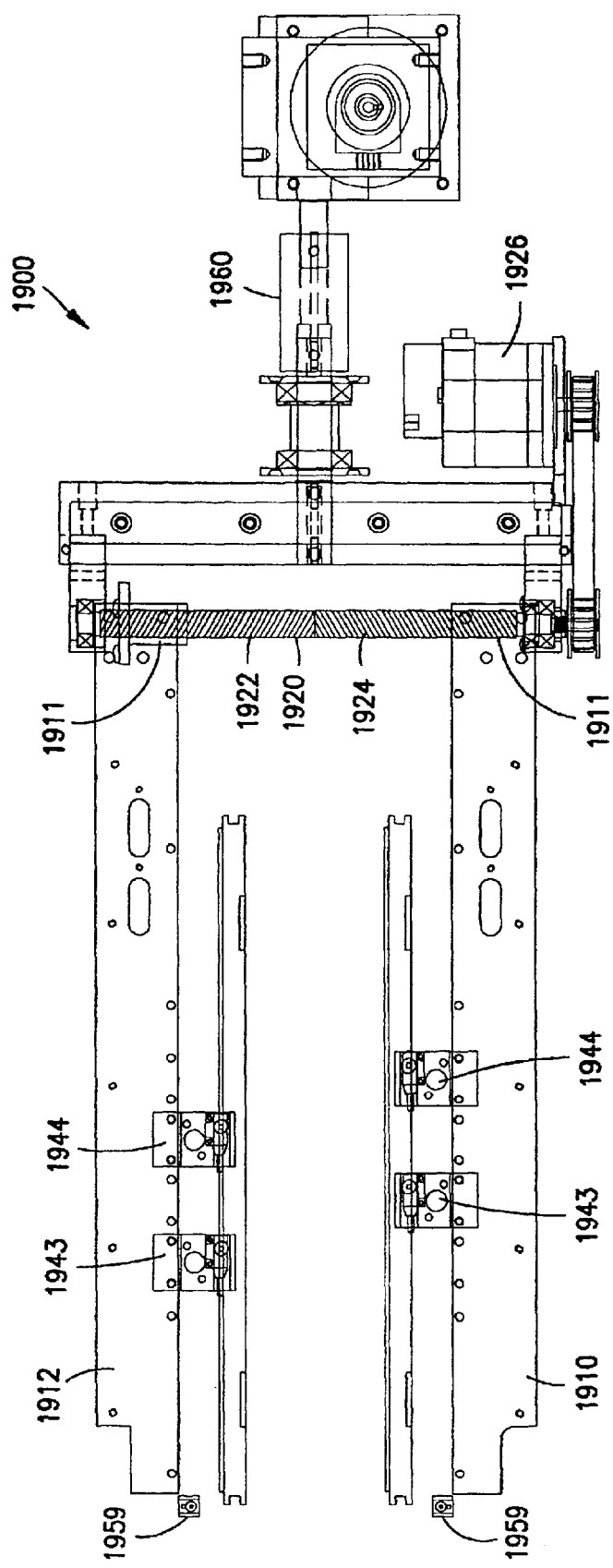
FIG. 19A is a side view of one tray inverter mechanism.
Figure 19B:
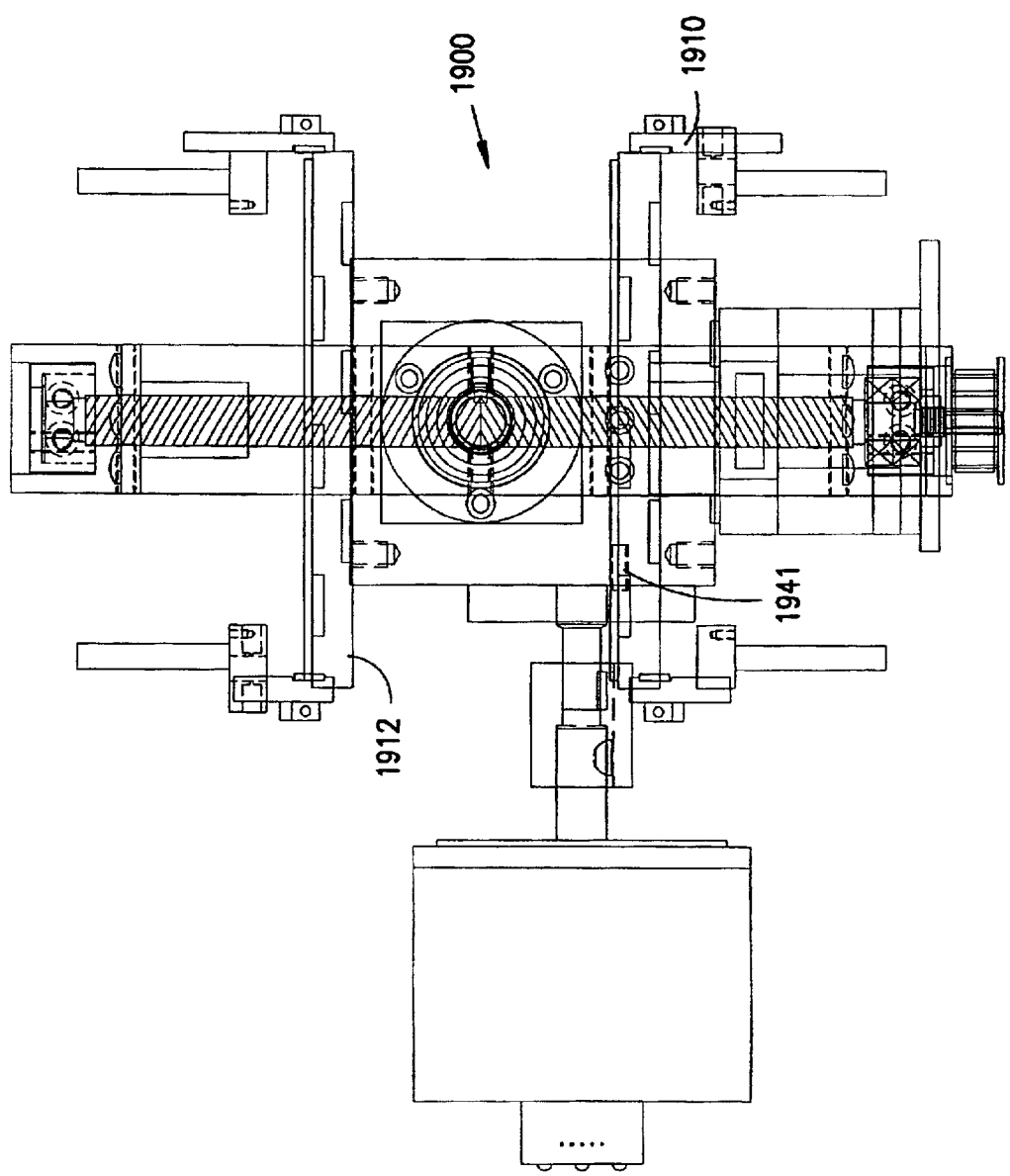
FIG. 19B is a front view of the tray inverter mechanism of FIG. 19A.
Figure 19G:
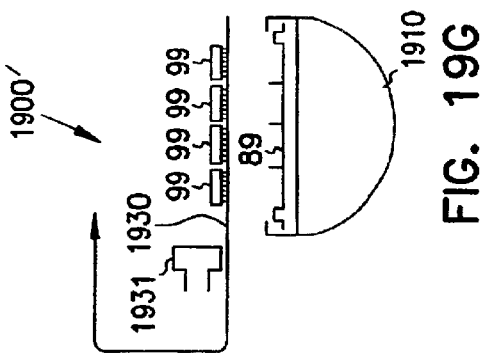
FIGS. 19C, 19D, 19E, 19F, 19G are front views of another tray inverter mechanism.
Figure 19F:
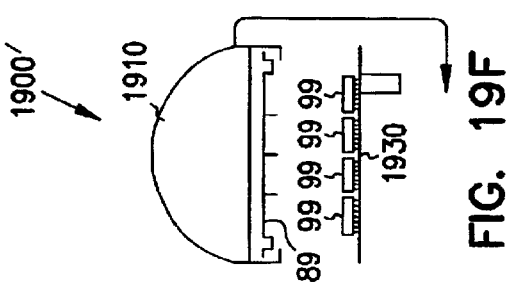

In the embodiment shown in FIG. 16, at the first inspection station 1610, the JEDEC trays are presented to an inspection surface which is positioned at a set distance from the inspection cameras 1631 and 1632 on the gantry 1630 above the inspection station 1610. The semiconductor devices in the JEDEC tray are all positioned with the ball side of the ball grid array devices presented for inspection (i.e., with electrical leads upwards, also called the "dead-bug orientation"). At the first inspection station 1610, a 3D image of the balls of each of the semiconductor devices in the JEDEC trays is obtained. The 3D inspection is used to gather information with respect to the height of the ball tops (e.g., the co-planarity of the top of all the balls), among other things (such as the shape and/or position of the balls, the position of the balls with respect to features on the substrate, etc.). At the inspection station 1612, a two-dimensional or 2D image of the ball side of the semiconductor devices in the JEDEC trays is obtained. The 2D information is useful in determining blob size, among other things. After the three-dimensional inspection at station 1610 and after the two-dimensional inspection at station 1612, the JEDEC trays are inverted so that the side of devices 99 opposite the balls can now be inspected (also called the "live-bug side" of the devices 99). The tray inverter or flipping mechanism 1900 will be discussed in further detail below when FIG. 19A and FIG. 19B are described in further detail, below.

In one embodiment, at inspection station 1614, the top of the package is inspected with a 3D camera 1631'. Such package inspection includes checking the dimensions of the package, whether there are chips, cracks, scratches or voids, among other things. In this embodiment, at inspection station 1616, the markings are inspected with a 2D camera 1632'. In one embodiment, each of the ball-grid-array semiconductor devices in the JEDEC tray is marked with a model number and serial number as well as the manufacturer's identification so that the parts may be tracked.

In the embodiment shown, a second gantry 1630' is positioned over the inspection station 1614 and inspection station 1616. The gantry 1630' includes a gantry arm 1634'. A first inspection camera 1631' and a second inspection camera 1632' are mounted to the gantry arm so that each of the inspection cameras 1631' and 1632' can move independently of the other inspection camera. The gantry 1634' can also move between inspection stations 1614 and 1616 so that the various inspections may be accomplished at those stations. In one embodiment, the second gantry 1630' and inspection camera 1631 ' and 1632' are essentially the same as the first gantry 1630.

In other embodiments, such as described for FIG. 10 above, other combinations of one or more 2D and/or 3D cameras are provided for the inspection of the front, backs, and/or sides of devices 99 being inspected. In such embodiments, one or more inspection stations, flipping stations, and/or sorting (pick-and-place) stations are provided.

In this embodiment shown in FIG. 16, the trays of devices are moved quickly into position, and then stopped, in order that the parts do not move in the trays. Thus, the parts remain stationary, and the camera(s) (e.g., camera 1631, 1632, 1631' and 1632') are moved to perform the scanning operation.

In yet other embodiments, the devices are moved and the scanning camera remains stationary. In one such embodiment, the devices 99 are mounted to a carrier strip (e.g., a suitable plastic film), and the carrier strip and devices are moved in a series in the optical path of one or more 2D and/or 3D scanning cameras (such as, for example camera head 401 of FIG. 4A.

After the inspection of the various parts at inspection stations 1610, 1612, 1614 and 1616 are completed, any bad parts or parts failing inspection are noted, as well as the position of the parts within the particular tray. The tray with good parts and bad parts is then moved from inspection station 1616 to pick-and-place station 1620. If there is not a tray located at pick-and-place station 1622, the tray of good and bad parts will be moved to pick-and-place station 1622 and another inspected tray of good and bad parts will be moved to pick-and-place station 1620. A vacuum pickup mechanism 2000 is used to remove bad parts from the trays located at pick-and-place station 1620 and place them into trays located at pick-and-place station 1622. The vacuum pickup 2000 also removes good semiconductor devices from the trays located at 1622 and places them into trays located at station 1620. In other words, the bad parts from trays at station 1620 are replaced with good parts from trays located at station 1622. Once all of the bad parts have been replaced in the tray located at station 1620, the tray of good parts is removed (e.g., automatically under the control of computer 1010, see FIG. 10 above) from that station and a new tray is positioned into station 1620. In one embodiment, a compartment and elevator is located below the pick-and-place station 1620, as well as below the pick-and-place station 1622.

When all of the parts are bad in the tray 1622, the parts are then removed (e.g., automatically under the control of computer 1010, see FIG. 10 above) from that pick-and-place station and into a compartment (e.g., lowered on an elevator) below that pick-and-place station. Therefore, all of the trays in the elevator and compartment below pick-and-place station 1622 will be trays of bad parts, while all of the trays below pick-and-place station 1620 will be trays of good parts that have successfully passed the inspection at the previous inspection stations 1610, 1612, 1614 and 1616. The pick-and-place mechanism 2000 will be described in further detail with respect to FIG. 20. It should be noted, however, that the pick-and-place station includes a vacuum pickup which uses a vacuum on the marked or label side of the semiconductor devices in the tray to move them from tray to tray.

Below each inspection station 1610, 1612, 1614 and 1616, as well as below each of the pick-and-place stations 1620 and 1622, is a compartment and elevator mechanism 1710, 1712, 1714, 1716, 1720 and 1722.

Figure 17A:
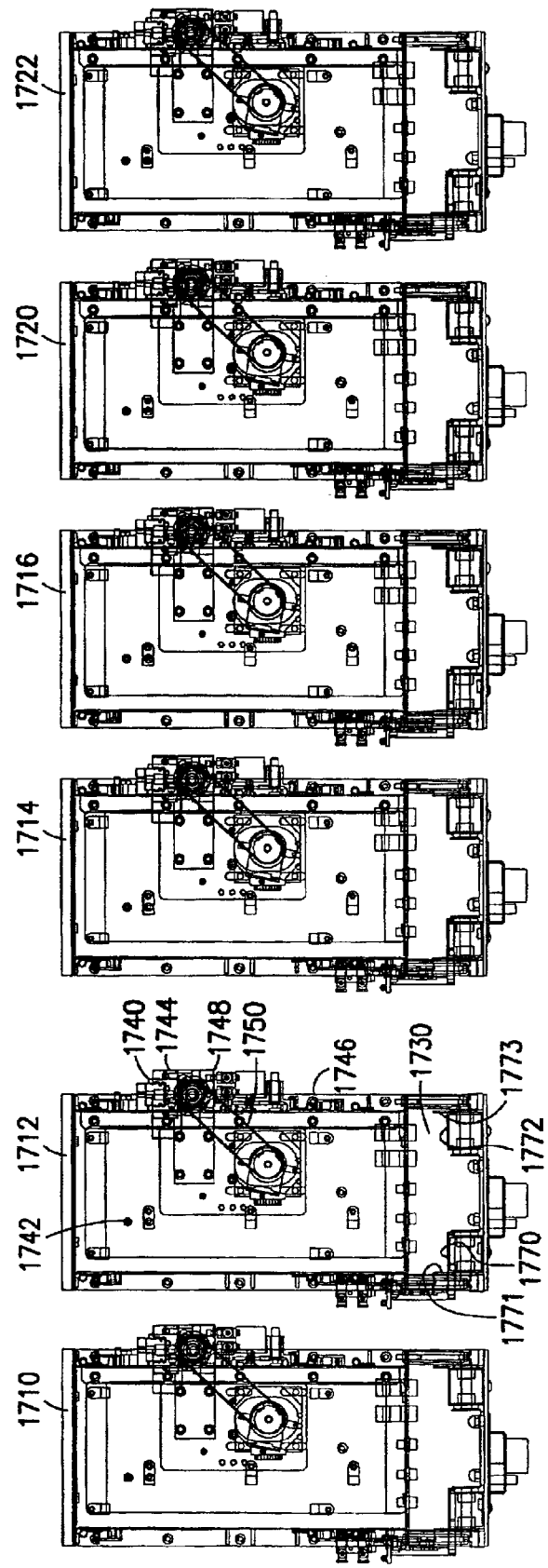
FIG. 17A is a top view of the compartment and the elevator mechanisms below each of the inspection stations of the machine-vision system.
Figure 17B:
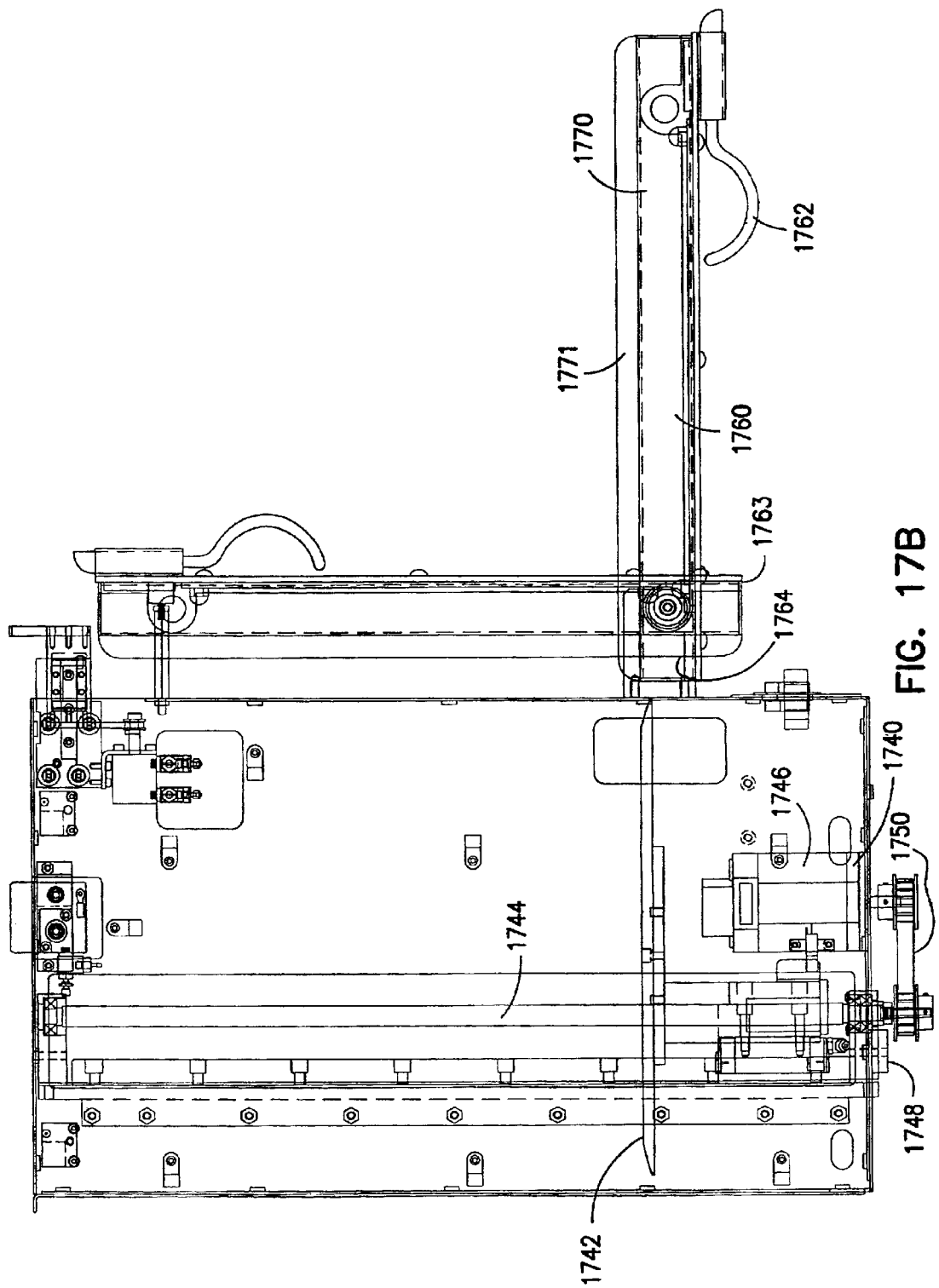
FIG. 17B is a side view of one of the compartment and the elevator mechanisms below an inspection station.

Now turning to FIGS. 17A and 17B, the elevator and compartment mechanisms 1710, 1712, 1714, 1716, 1720 and 1722 of one embodiment will now be discussed. FIG. 17A is a top view of the compartment and elevator mechanisms 1710, 1712, 1714, 1716, 1720 and 1722 of the machine-vision system 1600. FIG. 17B is a side view of one of the compartment and elevator mechanisms located below an inspection station. Since each of the compartment and elevator mechanisms 1710, 1712, 1714, 1716, 1720 and 1722 are substantially the same, only the compartment and elevator mechanism 1712 will be described in detail. It is to be understood that the others have substantially the same parts or elements.

The compartment and elevator mechanism 1712 includes a compartment 1730. Within the compartment 1730 is an elevator mechanism 1740. The elevator mechanism includes an elevator floor, an elevator guide 1744, a motor 1746 and a lifting mechanism 1748. The elevator motor 1746 is connected to the lifting mechanism 1748 with a belt 1750. Thus, by turning the motor 1746, the lifting mechanism 1748 is then used to raise the elevator floor up or down within the compartment 1730. The elevator guide 1744 and the lifting mechanism 1748 are positioned on the side of the elevator floor or elevator plate 1742. With the lifting mechanism 1748 and the elevator guide 1744 positioned on the side of the elevator floor or elevator plate, the JEDEC trays which hold the semiconductor devices can be moved into the compartment onto the elevator floor and then abutted to the back side of the compartment 1730 without interference from the elevator guide 1744 or the lifting mechanism 1748.

Access to the compartment 1730 of the compartment and elevator mechanism 1712 is gained through a door 1760. The door has a handle 1762. The door 1760 pivots on a pivot point 1763. Also associated with the door 1760 is a solid door stop 1764 which stops the door in a substantially parallel position with respect to the elevator floor 1742 when the compartment 1730 is devoid of JEDEC trays. The door 1760 is shown in a closed position, as well as an open position, in FIG. 17B. The compartment 1730 is also devoid of JEDEC trays for the sake of illustration.

When the compartment 1730 is empty, the elevator floor 1742 is moved to a position where it is essentially or substantially level with respect to the door. The door 1760 includes a first tray guide 1770 and a second tray guide 1772. The first tray guide 1770 includes a lip 1771. The second tray guide 1772 also includes a lip 1773. When the door 1760 is open, the surface of the first tray guide 1770 and the second tray guide 1772 is almost or substantially level with the position of the elevator floor 1742 within the compartment 1730. The lips 1771 and 1773 of the door 1760 are dimensioned so that the JEDEC trays fit between the lips 1771 and 1773 with a slight amount of clearance.

Advantageously, when a operator loads trays into the compartment 1730, the door 1760 can be opened and a stack of JEDEC trays can be placed on the door and specifically on the first tray guide 1770 and the second tray guide 1772. The bottom tray of the stack of JEDEC trays will fit between the lip 1771 associated with the first tray guide and the lip 1773 of the second tray guide 1772. The operator can then merely slide the stack of JEDEC trays into the compartment and onto the elevator floor 1742. By sliding them in all the way, the stack of JEDEC trays will be placed against the back wall of the compartment 1730. In addition, the lips 1771 and 1773 on the door also are used to position the trays carrying the semiconductor parts within the compartment 1730. In other words, the lips 1771 and 1773 on the door 1760 position the JEDEC trays properly along the width dimension of the compartment 1730. When placed in the compartment using the door, the trays are very close to the position that they will need to be in for presentation to the tray-transfer device 1800 above the compartment 1730, and at either an inspection station 1610, 1612, 1614 or 1617, or at a pick-and-place station 1620 or 1622. The details of the tray-transfer device 1800 will be discussed in further detail with respect to FIGS. 18A and 18B.

The elevator mechanism 1740 also includes a sensor 1780 or a series of sensors 1780. The sensors 1780 determine the JEDEC tray as well as the number of JEDEC trays loaded with the elevator mechanism 1712. Signals from the sensors are then used by a separate controller to control the electric motor so that the top JEDEC tray can be moved to an inspection station, such as 1612 which is above the compartment and elevator mechanism 1712.

Now turning briefly to look at inspection station 1610 and the compartment and elevator mechanism 1710 situated below the first inspection station 1610, a special advantage of this particular inspection vision machine 1600 will now be discussed. The JEDEC trays which hold the devices to be inspected can be moved directly from the compartment and elevator mechanism 1710 to the first inspection station 1610. In fact, the elevator mechanism 1710 moves the top JEDEC tray to the inspection surface associated with the inspection station 1610. In order to do this, the compartment and elevator mechanism 1710 must be substantially aligned with the inspection station 1610.

This is advantageous because it reduces the footprint of the machine-vision system 1600, and thus the space needed on a factory floor. In previous systems, a separate station would be positioned before the first inspection station 1610 and the JEDEC trays are essentially lowered to the station so that it can be loaded into a first inspection station such as 1610. Thus, previous systems required a separate loading station to the side of the first actual inspecting station. By using an elevator mechanism and compartment 1710 below the first inspection station 1610, there is no need for a separate loading station. An additional advantage is that all of the JEDEC trays are positioned on a solid elevator floor 1742. In previous inspection stations where there is a loading station, a set of pins is used to hold the bottom tray which is lowered to a loading station. The disadvantage with this previous system is that the pins, typically four or five, carry the entire load of all the JEDEC trays in the stack. Thus, the pins were much more prone to failure. In addition, the JEDEC trays were not held as solidly and were stressed which, in turn, stresses the parts located within the JEDEC tray. Using the solid elevator floor 1742 provides for a much more reliable system, as well as a system that will not stress the parts or the trays. In addition, the use of an elevator raising the JEDEC trays up from below the inspection surface 1610, eliminates the need for a separate loading station.

A first tray-transfer device 1800, a second tray-transfer device 1802 and a third tray-transfer device 1804 are used to move the JEDEC trays between the inspection station 1610, the inspection station 1612, the inspection station 1614, the inspection station 1616, the pick-and-place station 1620, the pick-and-place station 1622, and the tray inverter or flipping mechanism 1900.

Figure 18A:
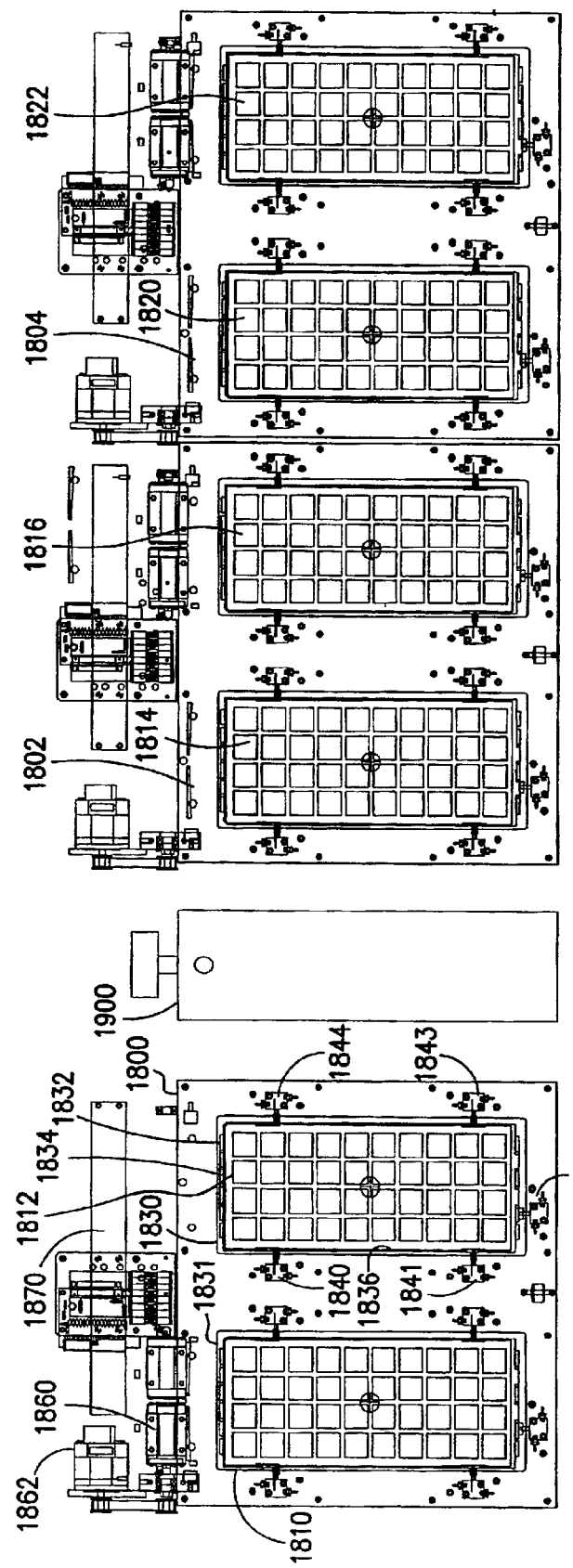
FIG. 18A is a top view of the inspection stations and the tray-transfer devices for moving trays between the various inspection stations, the pick and place stations, and the tray inverter or flipper mechanism.
Figure 18B:
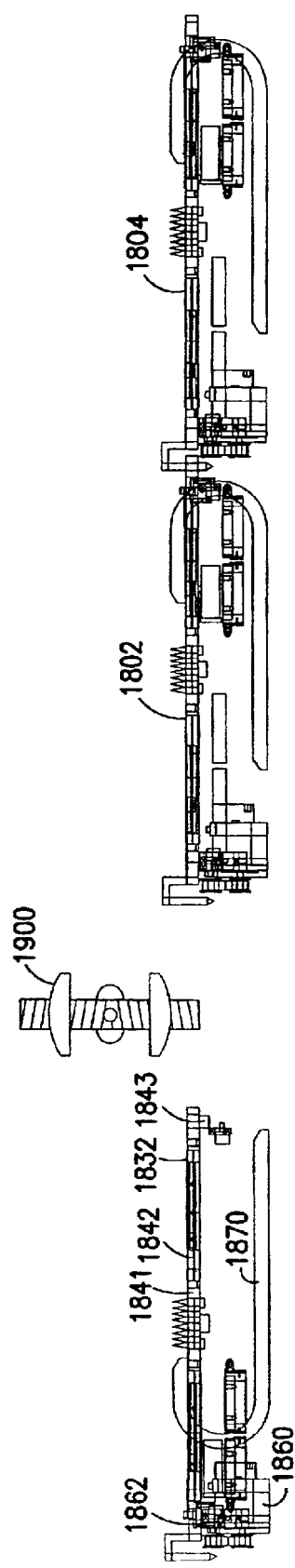
FIG. 18B is a front view of one of the tray-transfer devices for moving trays between the various inspection stations, the pick and place stations and the tray inverter or flipper mechanism.

Now turning to FIGS. 18A and 18B, the tray-transfer devices 1800, 1802, 1804 will now be further detailed. FIG. 18A is a top view of the inspection stations and the tray-transfer devices for moving trays between the various inspection stations, the pick-and-place stations, and the tray inverter or flipper mechanism 1900. FIG. 18B is a front view of one of the tray-transfer devices. The gantries, as well as the pick-and-place mechanism 2000, have been removed from the top view of FIG. 18A so that the tray-transfer devices can be more clearly shown.

As currently positioned, the tray-transfer device 1800 has a first JEDEC tray 1810 positioned at inspection station 1610 and a second JEDEC tray 1812 positioned at inspection station 1612. The first tray-transfer device 1800 moves JEDEC trays between the first inspection station 1610, the second inspection station 1612 and the flipping mechanism 1900. The second tray-transfer device 1802 moves JEDEC trays between the flipping mechanism 1900, the inspection station 1614 and the inspection station 1616. The second tray-transfer device is holding JEDEC tray 1814 at inspection station 1614 and JEDEC tray 1816 at inspection station 1616. The third tray-transfer device 1804 is shown holding a JEDEC tray 1820 at pick-and-place station 1620 and holding a JEDEC tray 1822 at pick-and-place station 1622. The tray-transfer device 1804 moves JEDEC trays between inspection station 1616 and pick-and-place station 1620 and pick-and-place station 1622. Each of the tray-transfer devices 1800, 1802, 1804 are essentially the same. Therefore, only one will be described herein.

The tray-transfer device 1800 includes a plate 1830 which has a first opening 1831 and a second opening 1832 therein. The openings 1831 and 1832 in the plate 1830 are dimensioned so that a standard JEDEC tray, such as 1810 or 1812, will fit within the opening 1831 or 1832. Positioned around each of the openings is a series of engagement pin mechanisms 1840, 1841, 1842, 1843 and 1844. As shown in FIG. 18A, each tray is engaged by five pin mechanisms 1840, 1841, 1842, 1843 and 1844. The pin mechanisms 1840, 1841, 1842, 1843 and 1844 engage standard openings in the JEDEC tray 1812. It should be noted that the JEDEC trays are standard, so JEDEC tray 1810 or JEDEC tray 1812 will each be engaged in the same fashion.

Five pins are positioned around each opening 1831 and 1832. The first pin to engage is pin 1842. The pin 1842 not only engages a portion of the JEDEC tray 1812, but also pushes the JEDEC tray toward or to a datum surface 1834, associated with the opening 1832. The next two pins that engage are along one edge of the JEDEC tray. In this particular instance, the pins 1844 and 1843 engage the JEDEC tray 1812 next and push the tray toward another datum surface 1836, associated with the opening 1832. It should be noted that this sequence could be reversed and that the most important aspect is that the JEDEC tray 1812 be pushed up against datum surfaces 1834 and 1836, as the pins 1842, 1843 engage the JEDEC tray.

The final set of pins to engage the JEDEC tray are 1840 and 1841. By pushing the JEDEC tray to the datum surface 1832 and to the second datum surface 1836, the exact location of the tray is known. With the JEDEC tray positioned against the datum surfaces 1834 and 1836 and with the plate 1830 also positioned against a datum surface, the exact location of the JEDEC tray within the opening 1832, the exact location in space with respect to the gantry is known. A 2D or 3D inspection, or any inspection for that matter, needs to have this data before the inspection can begin. Each of the pin mechanisms 1840, 1841, 1842, 1843 and 1844 is capable of a first and a second position with respect to the surface of the plate 1830. In the industry there are two standard JEDEC trays for holding electronic parts such as semiconductor ball grid array devices. A first standard JEDEC tray has a depth which is smaller than the second standard JEDEC tray. By having the pins 1840, 1841, 1842, 1843 and 1844 positionable to one of two positions, the two standard width or depth JEDEC trays that the machine-vision system 1600 will be required to handle, can be accommodated.

Also associated with the tray-transfer device 1800 is a tray driver mechanism 1860. The tray driver mechanism 1860 is driven by an electric motor 1862. The tray driver moves flat plate 1830 of the tray-transfer device 1800 to various positions between the inspection station 1610, the inspection station 1612, and the tray inverter or flipper mechanism 1900. The plate of the tray transfer mechanism includes a series of precision bearings on the bottom surface. The plates essentially roll along a precision surface associated with the machine-vision system 1600. This allows the tray-transfer device 1800 to move between the stations 1610 and 1612 and the flipper or tray inverter mechanism 1900. A belt 1864 connects the driver mechanism 1860 to the electric motor 1862.

A cable harness 1870 is used to provide the electronic control signal used to control the driver.

The tray inverter mechanism 1900 is used to turn the semiconductor devices housed or held by a JEDEC tray from one position to another position. Essentially, the tray inverter moves the semiconductor devices, such as a ball grid array device, from the ball side to the flat side opposite the ball side, being exposed within the JEDEC tray.

Now turning to FIGS. 19A and 19B, the tray inverter mechanism 1900 will be further detailed. FIG. 19A is a side view of the tray inverter mechanism or flipper 1900. FIG. 19B is a front view of the tray inverter mechanism or flipper 1900. The tray inverter mechanism 1900 includes a first jaw 1910 and a second jaw 1912. The jaw 1910 and the jaw 1912 are essentially a flat plate. The jaws 1910 and 1912 could also each be a set of spaced-apart, cantilevered ends. The jaws 1910 and 1912 have thread engagement ends 1911 and 1913, respectively. The engagement ends 1911 and 1913 are openings within the jaws 1910 and 1912, respectively, which are threaded so that they can ride on a threaded shaft 1920.

The threaded shaft includes a right-hand threaded portion 1922 and a left-hand threaded portion 1924. The threaded shaft 1920 is turned by an electric motor 1926. When the motor 1926 turns the threaded shaft 1920 one way, the jaws 1910 and 1912 will move toward one another. When the electric motor 1926 rotates the threaded shaft 1920 in the other direction, the jaws 1910 and 1912 will move away from each other.

Each of the jaws includes a set of engagement pins 1941, 1943 and 1944. Although only three engagement pins are shown for each jaw 1910 and 1912, it should be understood that there is a fourth pin which is not shown. The four engagement pin mechanisms engage the side openings of the JEDEC tray. Associated with each of the jaws 1910 and

1912 is a sensor 1957 and 1959. The sensors 1957 and 1959 sense the distance between the first jaw 1910 and the second jaw 1912. The sensors are used to prevent a spill of all of the semiconductor devices carried within a particular JEDEC tray that are about to be inverted.

The signals from the sensors 1957 and 1959 indicate how close they are with respect to one another. If the two sensors 1957 and 1959 are not close enough, the inverter will not try to attempt to invert the tray. If the sensors 1957 and 1959 are not close enough, the operator must check to see if all of the semiconductor devices are within the JEDEC tray.

One of the common things that happens when handling semiconductor devices within a JEDEC tray is that one or more of the semiconductors may become jostled and come out of the tray slightly and become pinched between a tray held by the jaw 1910 and the JEDEC tray held by the jaw 1912. In that event, the JEDEC trays would not be engaged with one another and inverting them would merely spill the remaining semiconductor devices, causing a stoppage of the inspection system while the semiconductor devices are cleaned up. The sensors 1957 and 1959 prevent this from occurring.

Also associated with the inverter device is a rotator 1960. The rotator moves the jaws 1910 and 1912 substantially 180° from one another. In other words, the rotator flips the first jaw from a "lower" position to an "upper" position and flips another jaw from an "upper" position to a "lower" position. The rotator 1960 includes stops so that the trays will essentially be flipped through 180°. A rotator motor 1962 is used to drive the rotator. The rotator motor can also have stops or be a motor that works between 0° and 180°.

In operation, an empty JEDEC tray is held within the pin engagement mechanisms associated with the upper jaw 1912. A populated or full tray is moved from inspection station 1612 to a position over the lower jaw 1910, as shown in FIGS. 19A and 19B, by the tray-transfer device 1800. The threaded shaft 1920 is turned so that the tray-transfer device can move over the jaw 1910 without interference with pin-locking mechanisms 1941, 1943 and 1944, as well as the pin mechanism which is not shown. The threaded shaft is then turned so that the jaw 1910 is traveling toward the jaw 1912 until the pins 1941, 1943 and 1944 and the unshown pin are able to engage the populated JEDEC tray. Once the populated JEDEC tray is removed from the tray-transfer device opening 1832, the threaded shaft 1920 is turned in the opposite way to lower the tray from the opening 1832 in the tray-transfer device 1800. The tray-transfer device or the plate 1830 of the tray-transfer device is then removed from between the jaws 1910 and 1912 of the tray inverter or flipping mechanism 1900.

After the tray-transfer device 1800 is clear of the tray inverter 1900, the threaded shaft is rotated so that the populated tray held by jaw 1910 approaches and engages the unpopulated tray held by jaw 1912. The sensors 1957 and 1959 assure that the two JEDEC trays properly engage one another so that electronic devices held within the two JEDEC trays will not spill during the inversion process. Once-the sensors 1957 and 1959 indicate that the two JEDEC trays are properly engaged, the rotator 1960 and the rotator motor 1962 are used to flip the JEDEC trays 180 degrees. Once inverted, the now populated tray is removed from the jaw 1912 using the tray-transfer device 1802.

The threaded shaft is used to lower the now populated JEDEC tray having flipped-over devices to a point where the second tray-transfer device 1802 can be moved over the jaw with the JEDEC tray thereon. The threaded shaft then moves the JEDEC tray up and into engagement with the opening 1831, associated with the second tray-transfer device 1802. A pin mechanism also engages the side of the tray. It should be noted that the pins of the jaws are spaced to grab a different set of openings in the JEDEC tray than the pins of the tray-transfer devices. The tray-transfer device is then used to move the tray to the inspection station 1814 where the dimensions of the semiconductor devices are checked. The previously populated JEDEC tray now becomes the new empty tray which is in the upper jaw. The process is repeated over and over as the JEDEC trays move down the line.

It should be noted that the JEDEC trays move in a direction which is parallel to the short dimension of the JEDEC trays. This, too, is an additional advantage is keeping the footprint of the machine-vision system 1600 at a minimum. In other words, by transferring the trays along a direction parallel to the short direction of the JEDEC trays, the linear dimension of the machine-vision system 1600 is shortened.

Figure 19E:
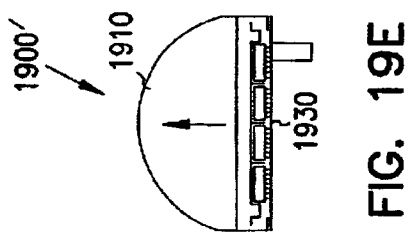
Figure 19D:
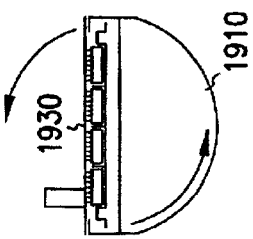
Figure 19C:
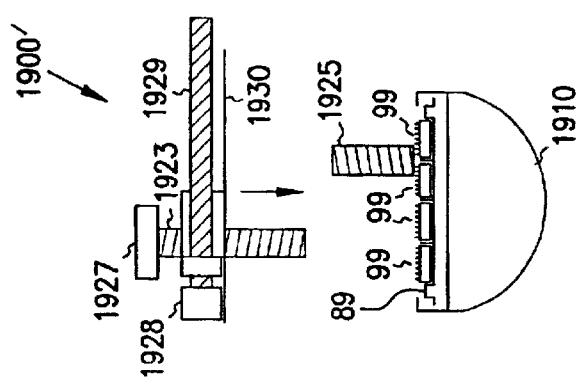

Now turning to FIGS. 19C, 19D, 19E, 19F, and 19G, and FIGS. 19H, 19I, 19J, 19K, and 19L, the tray inverter mechanism 1900' will be further detailed. FIGS. 19C–19G are end views of the tray inverter mechanism or flipper 1900' in various stages of operation. FIGS. 19H-19L are corresponding side views of the respective FIGS. 19C–19G. FIG. 19C shows a jaw 1910 having a tray 89 populated with a plurality of devices 99. Jaw 1930 of FIG. 19C replaces jaw 1912 of FIG. 19A, and is operated in a similar manner, except as described in more detail below. In one embodiment, jaw 1930 has an operative surface that is a thin stiff sheet of a suitable metal. Tray 89 is held in jaw 1910 as described above for FIG. 19A. Jaw 1930 is lowered (and/or jaw 1910 is raised) until it is near or touching the upper surfaces of devices 99, as is shown in FIG. 19D. FIG. 19H shows a side-view schematic diagram of the embodiment of invertor mechanism 1900'. In this embodiment, jaw motor 1926 rotates threaded shaft 1925 to raise and lower jaw 1910. Jaw motor 1927 rotates threaded shaft 1923 to lower and raise jaw 1930. Slider motor 1928 rotates threaded shaft 1929 to move jaw 1930 laterally in order to slide it out from under devices 99, as further described below for FIG. 19G. Some of the details are omitted in FIGS. 19C–19L for clarity of explanation.

Referring to the end view FIG. 19D (and corresponding side view of FIG. 19I), both jaws, now in engagement, are rotated (e.g., using rotator motors 1961 and 1962, shown schematically) in order to invert all the devices 99, resulting in the orientation shown in FIG. 19E (and corresponding side view of FIG. 19J). Jaw 1910 is raised (and/or jaw 1930 is raised) until the two jaws are sufficiently separated, thus leaving the devices 99 resting with the previously upper surfaces of devices 99 now downward on jaw 1930, and tray 89 held in jaw 1910 away from the devices, resulting in the orientation shown in FIG. 19F (and corresponding side view of FIG. 19K). Jaw 1910 is then inverted and moved to a position below jaw 1930 resulting in the orientation shown in FIG. 19G (and corresponding side view of FIG. 19L). In one embodiment, jaw 1930 is then slid laterally using slider motor 1928 and screw 1929, with a holder or pusher 1931 holding the devices in position above tray 89 as jaw 1930 is moved out of the way. As jaw 1930 is slid out of the way, the devices 99 drop into tray 89, with their orientation inverted as compared to FIG. 19C. The jaws each then return to their respective original positions, using their respective motors 1926, 1927, 1928 1961 and 1962, resulting in the orientation shown in FIG. 19C (and corresponding side view of FIG. 19H), and the tray of inverted parts is removed from jaw 1910, in a manner similar to that described above. In this embodiment (shown in FIGS. 19C–19L), the second tray (as used in FIGS. 19A and 19B) is not used, but rather a quite similar inverting operation is used to invert all the devices and place them back into the same tray as they started in. In some embodiments, tray 89 is a pocketed tray, with a separate pocket associated with and holding each device. In other embodiments, a container or tray without pockets is used.

In yet another embodiment, a configuration otherwise substantially the same as shown in FIGS. 19C–19L is used, except that no tray is used. A first conveyor moves a plurality of devices 99 onto lower jaw 1910 (similar to FIG. 19C, but without tray 89). Jaw 1930 is lowered onto the devices (similar to FIG. 19D, but without tray 89), and the two engaged jaws rotate to invert all of the devices in a single operation (similar to FIG. 19E, but without tray 89). A conveyor (either the first conveyor, or a second conveyor) then removes the devices from jaw 1930.

Figure 20:
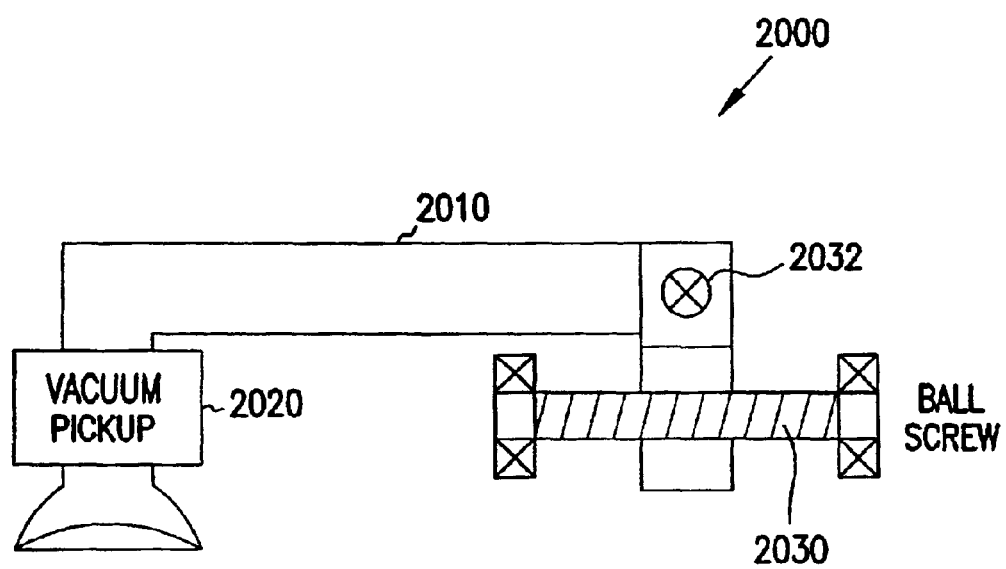
FIG. 20 shows picker for replacing devices.

Now turning to FIG. 20, the picker and placer 2000 will be further detailed. FIG. 20 shows a pick and placer for replacing bad devices on JEDEC trays located at inspection station 1620 with good devices found in JEDEC trays at station 1622. The pick-and-place robot includes an arm 2010 and a vacuum pickup 2020. The vacuum pickup 2020 is placed on one end of the arm 2010. The other end of the arm includes a first ball screw device 2030 and a second ball screw device 2032. The first ball screw device translates the arm 2010 and the attached vacuum pickup 2020 along the length of the JEDEC trays at the pick-and-place stations 1620 or 1622. The second ball screw device 2032 moves the arm 2010 and the attached vacuum pickup 2020 up and down with respect to the inspection surface and up and down with respect to the devices within the JEDEC trays. The pick-and-place mechanism can also be moved controllably along the short dimensions of the trays so that the pick-and-place device 2000 can remove bad parts from the inspection station 1620 and place them in the bad trays located at station 1622, and then pick up a good part from station 1622 and replace the previously bad part in the JEDEC tray at station 1620.

Advantageously, the footprint of the machine-vision system for inspecting parts is smaller since an additional station is not needed for loading trays to the first inspection station. In addition, the trays are loaded onto a tray-transfer device so that the direction of travel along the tray-transfer device is along the shorter dimension of the trays. This provides for a shorter line and a smaller footprint. Another advantage is that the inspection can take place automatically without the intervention of a human. This lessens the chance for operator error during the inspection process.

Figure 21:
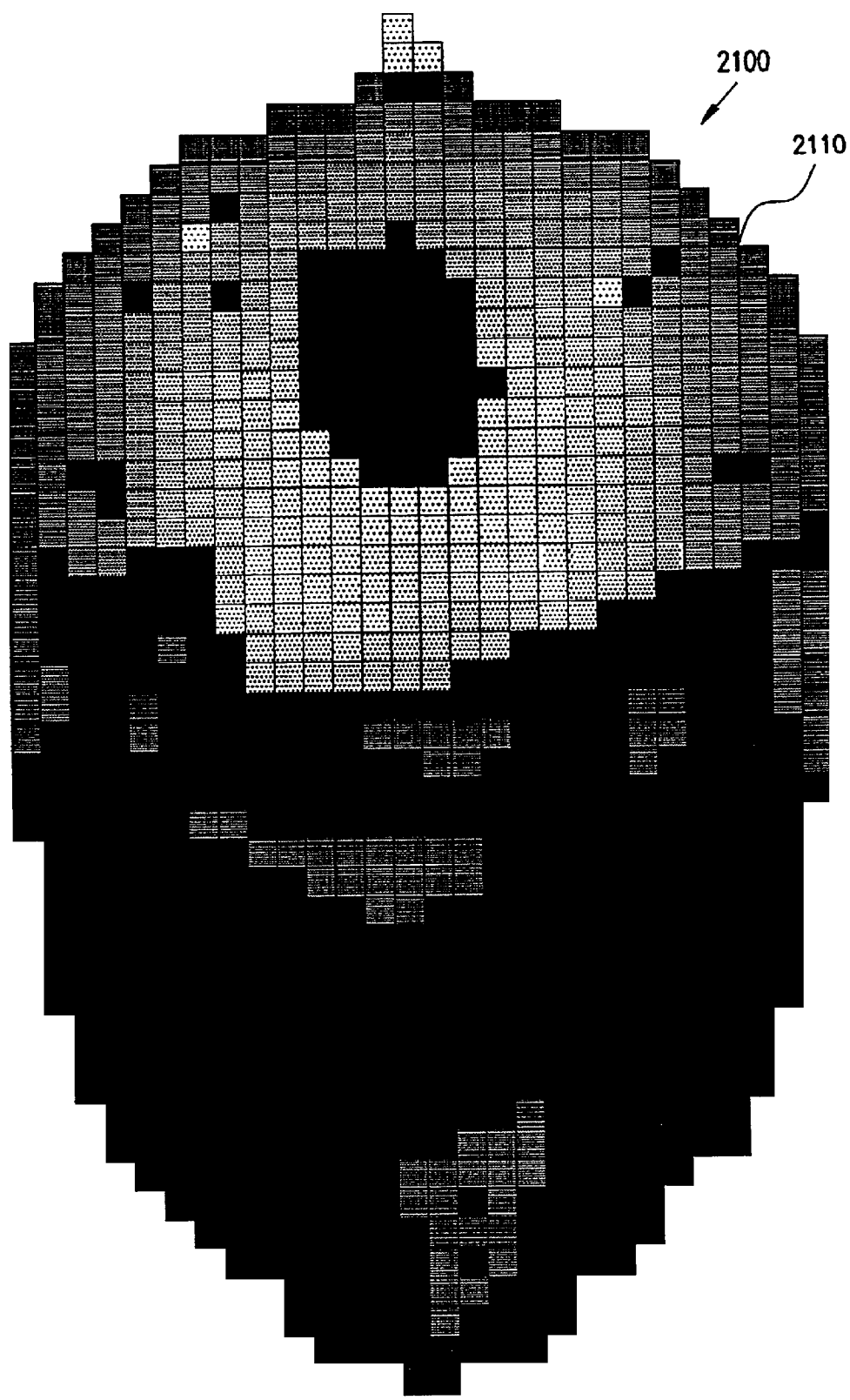
FIG. 21 shows an acquired image showing various heights of a ball being inspected.

FIG. 21 shows an acquired image 2100 showing various heights of a ball 2110 being inspected. The ball 2110 includes shadowed portions depicted by the black areas in the acquired image.

CONCLUSION

Advantageously, these inventions solve or lessen many of the problems associated In summary, the present invention provides a method and apparatus for identifying and handling device tilt in a three-dimensional machine-vision image which is generated from an inspection of a device under test. The device tilt is determined and compensated for, so that various problems previously associated with device tilt are substantially diminished if not entirely eliminated from the device inspection and production line.

It will be apparent to those skilled in the art that the disclosed invention can be modified in numerous ways and can assume many embodiments other than the preferred form specifically set out and described above.

For example, it will be understood by one of ordinary skill in the art that the selection of specific parameters, numbers of samples, tolerances, and so forth is a matter of design and operational optimization and fine tuning and will depend upon the particular environment and context in which the apparatus and method of the present invention are practiced. In one embodiment the process shown in the flow charts of the FIGS. and in the computer program listings appended hereto are performed in a different order than that indicated.

It will also be understood that while a preferred embodiment of the invention is described as being implemented in part on a stored program digital computer, the invention may also be implemented, in other embodiments, with special-purpose electronic circuits.

It will be further understood that other embodiments of the invention may be implemented using a different type of voting scheme, such as ballot box memory for example, than that shown herein for determining the most likely amount of tilt in the measured plane.

The following alpha-numbered paragraphs represent various embodiments and combinations according to various aspects of the present invention.

A1. One embodiment of the invention includes a machine-vision head for measuring a three-dimensional geometry of a device having a surface to be measured, including: a projector, the projector including: a first light source having a projection optical axis that intersects the device; a projection-imaging element positioned along the projection optical axis and spaced from the first light source; and a projection-pattern element positioned between the first light source and the projection imaging element along the projection optical axis, the projection-pattern element having a repeating sine-wave light-modulation pattern as measured along a line on the projection-pattern element; and an imager, the imager having a reception optical axis that intersects the device substantially at the projection optical axis.

A2. Some embodiments include the machine-vision head according to alpha-numbered paragraph A1, wherein the projection-pattern element light-modulation pattern includes a repeating pattern of grid lines having substantially constant density along lines in a direction parallel to the grid lines and a sine-wave density along lines in a direction perpendicular to the grid lines.

A3. Some embodiments include the machine-vision head according to alpha-numbered paragraph A2, wherein the first light source includes a elongated incandescent filament having a dimension along a longitudinal axis substantially longer than a width, wherein the longitudinal axis of the filament is substantially perpendicular to the projection optical axis and substantially parallel to the grid lines of the projection-pattern element.

A4. Some embodiments include the machine-vision head according to alpha-numbered paragraph A2, further including a projection mask having an elongated aperture having a dimension along a length axis substantially longer than a dimension along a width axis perpendicular to the length axis, and wherein the length axis is substantially parallel to the grid lines of the projection-pattern element.

A5. Some embodiments include the machine-vision head according to alpha-numbered paragraph A4, wherein the projection mask limits the projected light to less than about three sine-wave cycles of the sine-wave pattern.

A6. Some embodiments include the machine-vision head according to alpha-numbered paragraph A4, further including a projection-mask actuator operable to adjust a position of the projection mask.

A7. Some embodiments include the machine-vision head according to alpha-numbered paragraph A1, further including a light-intensity controller, coupled to receive intensity information regarding light output from the first light source, that outputs a control signal based on a measured intensity of light from the first light source.

A8. Some embodiments include the machine-vision head according to alpha-numbered paragraph A7, wherein the control signal is operatively coupled to the first light source to control light output based on the measured light intensity in a feedback manner.

A9. Some embodiments include the machine-vision head according to alpha-numbered paragraph A7, wherein the control signal is operatively coupled to the imager to control an amount of light received in an imaging cycle of the imager.

A10. Some embodiments include the machine-vision head according to alpha-numbered paragraph Al, further including a condensing imaging element positioned between the first light source and the projection-pattern element along the projection optical axis.

A11. Some embodiments include the machine-vision head according to alpha-numbered paragraph A1, further including a focussing reflector that substantially focusses an image of the first light source adjacent to the first light source.

A12. Some embodiments include the machine-vision head according to alpha-numbered paragraph A11, wherein the reception optical axis is oriented to be at substantially a right angle to a direction of scanning, and the projection optical axis is oriented to be at substantially a forty-five-degree angle to the direction of scanning.

A13. Some embodiments include the machine-vision head according to alpha-numbered paragraph A12, wherein a major plane of the projection-imaging element is oriented substantially perpendicular to the projection optical axis and a major plane of the projection-pattern element is oriented substantially perpendicular to the projection optical axis.

A14. Some embodiments include the machine-vision head according to alpha-numbered paragraph A1, further including a second light source that directs substantially unpatterned light onto the device, the second light source being activated to obtain two-dimensional intensity data about the device from the imager.

A15. One embodiment of the invention includes a machine-vision system for inspecting a device, including: (1) an inspection station, the inspection station including: (a) a projector, the projector including: a first light source having a projection optical axis that intersects the device; a projection-imaging element positioned along the projection optical axis and spaced from the first light source; and a projection-pattern element positioned between the first light source and the projection imaging element along the projection optical axis, the projection-pattern element having a repeating sine-wave light-modulation pattern as measured along a line on the projection-pattern element; and (b) an imager, the imager having a reception optical axis that intersects the device when the inspection station is in operation, the imager maintained in a substantially fixed relationship to the pattern projector, the imager including at least three lines of semiconductor imaging pixels; (2) a scanner mechanism that moves the imager relative to the device such that different portions of the device are successively imaged by the imager, wherein the first light source is activated in conjunction with the imager to obtain three-dimensional device geometry data regarding the device; and (3) a comparator coupled to the imager, the comparator comparing one or more characteristics of the acquired three-dimensional device geometry data with an intended predetermined geometry to produce a signal indicative of any device geometry departure of an actual device geometry from the intended predetermined geometry.

A16. Some embodiments include the system according to alpha-numbered paragraph A15, wherein the projection-pattern element light-modulation pattern includes a repeating pattern of grid lines having substantially constant density along lines in a direction parallel to the grid lines and a sine-wave density along lines in a direction perpendicular to the grid lines.

A17. Some embodiments include the system according to alpha-numbered paragraph A16, wherein the first light source includes a elongated incandescent filament having a dimension along a longitudinal axis substantially longer than a width, wherein the longitudinal axis of the filament is substantially perpendicular to the projection optical axis and substantially parallel to the grid lines of the projection-pattern element.

A18. Some embodiments include the system according to alpha-numbered paragraph A15, further including a projection mask having an elongated aperture having a dimension along a length axis substantially longer than a dimension along a width axis perpendicular to the length axis, and wherein the length axis is substantially parallel to the grid lines of the projection-pattern element.

A19. Some embodiments include the system according to alpha-numbered paragraph A18, wherein the projection mask limits the projected light to less than about three sine-wave cycles of the sine-wave pattern.

A20. Some embodiments include the system according to alpha-numbered paragraph A15, further including a light-intensity controller, coupled to receive intensity information regarding light output from the light source, that outputs a control signal based on a measured intensity of light from the light source, wherein the control signal is operatively coupled to the imager to control an amount of light received in an imaging cycle of the imager.

A21. Some embodiments include the system according to alpha-numbered paragraph A15, further including a focussing reflector that substantially focusses an image of the light source adjacent to the light source.

A22. Some embodiments include the system according to alpha-numbered paragraph A15, further including a condensing imaging element positioned between the first light source and the projection-pattern element along the projection optical axis.

A23. Some embodiments include the system according to alpha-numbered paragraph A15, wherein a major plane of the projection-imaging element is oriented substantially perpendicular to the projection optical axis and a major plane of the projection-pattern element is oriented substantially perpendicular to the projection optical axis.

A24. Some embodiments include the system according to alpha-numbered paragraph A15, further including a second light source that directs substantially unpatterned light onto the device, the second light source being activated in conjunction with the imager to obtain two-dimensional intensity data about the device from the imager.

A25. One embodiment of the invention includes a method for measuring a three-dimensional geometry of a device having a surface to be measured, including: projecting patterned light having a spatial-modulation pattern; the projecting pattern light including: (a) projecting substantially unpatterned light, (b) spatially modulating the unpatterened light with a sine-wave spatial modulation pattern to produce spatial-modulation patterned light, and (c) imaging the spatial-modulation patterned light onto the device; scanning the device within the spatial-modulation patterned light; and receiving reflected light from the device into at least three linear imager regions.

A26. Some embodiments include the method according to alpha-numbered paragraph A25, wherein the spatially modulating includes modulating with a repeating pattern of grid lines having substantially constant density along lines in a direction parallel to the grid lines and a sine-wave density along lines in a direction perpendicular to the grid lines.

A27. Some embodiments include the method according to alpha-numbered paragraph A26, wherein the projecting substantially unpatterned light source includes a elongated light beam, wherein a longitudinal axis of the beam is perpendicular to the direction of projection and parallel to the grid lines.

A28. Some embodiments include the method according to alpha-numbered paragraph A26, further including projection masking to an elongated aperture having a length axis substantially greater that a width axis, and wherein the length axis is substantially parallel to the grid lines of the pattern.

A29. Some embodiments include the method according to alpha-numbered paragraph A28, wherein the projection masking limits the projected light to less than about three sine-wave cycles of the sine-wave pattern.

A30. Some embodiments include the method according to alpha-numbered paragraph A28, further including a adjusting a position of the projection masking.

A31. Some embodiments include the method according to alpha-numbered paragraph A25, further including generating a light-intensity control signal based on intensity information regarding the projected light.

A32. Some embodiments include the method according to alpha-numbered paragraph A31, further including controlling a light source to control light output based on the measured light intensity in a feedback manner.

A33. Some embodiments include the method according to alpha-numbered paragraph A31, further including controlling an imager to control an amount of light received in an imaging cycle of the imager.

A34. Some embodiments include the method according to alpha-numbered paragraph A25, further including condensing light onto the projection-pattern along the projection optical axis.

A35. Some embodiments include the method according to alpha-numbered paragraph A25, further including reflectively focussing to substantially focus an image of the light source adjacent to the light source.

A36. Some embodiments include the method according to alpha-numbered paragraph A25, wherein the reception optical axis is oriented to be at substantially a right angle to a direction of scanning, and the projection optical axis is oriented to be at substantially a forty-five-degree angle to the direction of scanning.

A37. One embodiment of the invention includes a machine-vision head for measuring a three-dimensional geometry of a device having a surface to be measured, including: a projector, the projector including: a first light source having a projection optical axis that intersects the device; a condensing imaging element positioned along the projection optical axis and spaced from the light source by a distance $D_4$; a projection imaging element positioned along the projection optical axis and spaced from the condensing imaging element by a distance $D_3$; and a projection-pattern element 1 positioned along the projection optical axis and between the condensing imaging element and the projection imaging element and spaced from the projection imaging element by a distance $D_2$, the projection-pattern element having a repeating light-modulation pattern that modulates light from the first light source to generate a patterned light useful for determining three-dimensional geometry of the device, wherein a projection-imaging-element-to-device distance $D_1$ and the distance $D_2$ are configured to focus an image of projection-pattern element at the surface of device, and the distance $D_3$ and the distance $D_4$ are configured so as focus an image of the light source onto the projection-pattern imaging element; and an imager, the imager having a reception optical axis that intersects the device substantially at the projection optical axis, the imager receiving the patterned light as reflected by the device.

A38. Some embodiments include the machine-vision head according to alpha-numbered paragraph A37, wherein the projection-pattern element light-modulation pattern includes a repeating pattern of grid lines having substantially constant density along lines in a direction parallel to the grid lines and a sine-wave density along lines in a direction perpendicular to the grid lines.

A39. Some embodiments include the machine-vision head according to alpha-numbered paragraph A37, wherein the first light source includes a elongated incandescent filament having a dimension along a longitudinal axis substantially longer than a width, wherein the longitudinal axis of the filament is substantially perpendicular to the projection optical axis and substantially parallel to a pattern feature of the projection-pattern element.

A40. Some embodiments include the machine-vision head according to alpha-numbered paragraph A39, further including a projection mask having an elongated aperture having a dimension along a length axis substantially longer than a dimension along a width axis perpendicular to the length axis, and wherein the length axis is substantially parallel to the pattern feature of the projection-pattern element.

A41. Some embodiments include the machine-vision head according to alpha-numbered paragraph A40, wherein the projection-pattern element light-modulation pattern includes a repeating pattern of grid lines having substantially constant density along lines in a direction parallel to the grid lines and a sine-wave density along lines in a direction perpendicular to the grid lines, the pattern feature being the grid lines, and wherein the projection mask limits the projected light to less than about three sine-wave cycles of the sine-wave pattern.

A42. Some embodiments include the machine-vision head according to alpha-numbered paragraph A40, further including a projection-mask actuator operable to adjust a position of the projection mask.

A43. Some embodiments include the machine-vision head according to alpha-numbered paragraph A37, further including a light-intensity controller, coupled to receive intensity information regarding light output from the first light source, that outputs a control signal based on a measured intensity of light from the first light source.

A44. Some embodiments include the machine-vision head according to alpha-numbered paragraph A43, wherein the control signal is operatively coupled to the first light source to control light output based on the measured light intensity in a feedback manner.

A45. Some embodiments include the machine-vision head according to alpha-numbered paragraph A43, wherein the control signal is operatively coupled to the imager to control an amount of light received in an imaging cycle of the imager.

A46. Some embodiments include the machine-vision head according to alpha-numbered paragraph A37, further including a condensing imaging element positioned between the first light source and the projection-pattern element along the projection optical axis.

A47. Some embodiments include the machine-vision head according to alpha-numbered paragraph A37, further including a focussing reflector that substantially focusses an image of the first light source adjacent to the first light source.

A48. Some embodiments include the machine-vision head according to alpha-numbered paragraph A47, wherein the reception optical axis is oriented to be at substantially a right angle to a direction of scanning, and the projection optical axis is oriented to be at substantially a forty-five-degree angle to the direction of scanning.

A48. Some embodiments include the machine-vision head according to alpha-numbered paragraph A48, wherein a major plane of the projection-imaging element is oriented substantially perpendicular to the projection optical axis and a major plane of the projection-pattern element is oriented substantially perpendicular to the projection optical axis.

A50. Some embodiments include the machine-vision head according to alpha-numbered paragraph A37, further including a second light source that directs substantially unpatterned light onto the device, the second light source being activated to obtain two-dimensional intensity data about the device from the imager.

A51. One embodiment of the invention includes a machine-vision system for inspecting a device, including: (1) an inspection station, the inspection station including: (a) a projector, the projector including a first light source having a projection optical axis that intersects the device, a condensing imaging element positioned along the projection optical axis and spaced from the light source by a distance $D_4$, a projection imaging element positioned along the projection optical axis and spaced from the condensing imaging element by a distance $D_3$, and a projection-pattern element 1 positioned along the projection optical axis and between the condensing imaging element and the projection imaging element and spaced from the projection imaging element by a distance $D_2$, the projection-pattern element having a repeating light-modulation pattern that modulates light from the first light source to generate a patterned light useful for determining three-dimensional geometry of the device, wherein a projection-imaging-element-to-device distance $D_1$ and the distance $D_2$ are configured to focus an image of projection-pattern element at the surface of device, and the distance $D_3$ and the distance $D_4$ are configured so as focus an image of the light source onto the projection-pattern imaging element; and (b) an imager, the imager having a reception optical axis that intersects the device substantially at the projection optical axis, the imager receiving the patterned light as reflected by the device; (2) a scanner mechanism that moves the imager relative to the device such that different portions of the device are successively imaged by the imager, wherein the first light source is activated in conjunction with the imager to obtain three-dimensional device geometry data regarding the device; and (3) a comparator coupled to the imager, the comparator comparing one or more characteristics of the acquired three-dimensional device geometry data with an intended predetermined geometry to produce a signal indicative of any device geometry departure of an actual device geometry from the intended predetermined geometry.

A52. Some embodiments include the system according to alpha-numbered paragraph A51, wherein the projection-pattern element light-modulation pattern includes a repeating pattern of grid lines having substantially constant density along lines in a direction parallel to the grid lines and a sine-wave density along lines in a direction perpendicular to the grid lines.

A53. Some embodiments include the system according to alpha-numbered paragraph A52, wherein the first light source includes a elongated incandescent filament having a dimension along a longitudinal axis substantially longer than a width, wherein the longitudinal axis of the filament is substantially perpendicular to the projection optical axis and substantially parallel to the grid lines of the projection-pattern element.

A54. Some embodiments include the system according to alpha-numbered paragraph A51, further including a projection mask having an elongated aperture having a dimension along a length axis substantially longer than a dimension along a width axis perpendicular to the length axis, and wherein the length axis is substantially parallel to the grid lines of the projection-pattern element.

A55. Some embodiments include the system according to alpha-numbered paragraph A54, wherein the projection mask limits the projected light to less than about three sine-wave cycles of the sine-wave pattern.

A56. Some embodiments include the system according to alpha-numbered paragraph A51, further including a light-intensity controller, coupled to receive intensity information regarding light output from the light source, that outputs a control signal based on a measured intensity of light from the light source, wherein the control signal is operatively coupled to the imager to control an amount of light received in an imaging cycle of the imager.

A57. Some embodiments include the system according to alpha-numbered paragraph A51, further including a focussing reflector that substantially focusses an image of the light source adjacent to the light source.

A58. Some embodiments include the system according to alpha-numbered paragraph A51, further including a condensing imaging element positioned between the first light source and the projection-pattern element along the projection optical axis.

A59. Some embodiments include the system according to alpha-numbered paragraph A51, wherein a major plane of the projection-imaging element is oriented substantially perpendicular to the projection optical axis and a major plane of the projection-pattern element is oriented substantially perpendicular to the projection optical axis.

A60. Some embodiments include the system according to alpha-numbered paragraph A51, further including a second light source that directs substantially unpatterned light onto the device, the second light source being activated in conjunction with the imager to obtain two-dimensional intensity data about the device from the imager.

A61. One embodiment of the invention includes a method for measuring a three-dimensional geometry of a device having a surface to be measured, including: (a) projecting patterned light having a spatial-modulation pattern; the projecting pattern light including projecting substantially unpatterned light, spatially modulating the unpatterned light with a sine-wave spatial modulation pattern to produce spatial-modulation patterned light, and imaging the spatial-modulation patterned light onto the device; (b) scanning the device within the spatial-modulation patterned light; and (c) receiving reflected light from the device into at least three linear imager regions.

A62. Some embodiments include the method according to alpha-numbered paragraph A61, wherein the spatially modulating includes modulating with a repeating pattern of grid lines having substantially constant density along lines in a direction parallel to the grid lines and a sine-wave density along lines in a direction perpendicular to the grid lines.

A63. Some embodiments include the method according to alpha-numbered paragraph A62, wherein the projecting substantially unpatterned light source includes a elongated light beam, wherein a longitudinal axis of the beam is perpendicular to the direction of projection and parallel to the grid lines.

A64. Some embodiments include the method according to alpha-numbered paragraph A62, further including projection masking to an elongated aperture having a length axis substantially greater that a width axis, and wherein the length axis is substantially parallel to the grid lines of the pattern.

A65. Some embodiments include the method according to alpha-numbered paragraph A64, wherein the projection masking limits the projected light to less than about three sine-wave cycles of the sine-wave pattern.

A66. Some embodiments include the method according to alpha-numbered paragraph A65, further including a adjusting a position of the projection masking.

A67. Some embodiments include the method according to alpha-numbered paragraph A66, further including generating a light-intensity control signal based on intensity information regarding the projected light.

A68. Some embodiments include the method according to alpha-numbered paragraph A67, further including controlling a light source to control light output based on the measured light intensity in a feedback manner.

A69. Some embodiments include the method according to alpha-numbered paragraph A68, further including controlling an imager to control an amount of light received in an imaging cycle of the imager.

A70. Some embodiments include the method according to alpha-numbered paragraph A69, further including condensing light onto the projection-pattern along the projection optical axis.

A71. Some embodiments include the method according to alpha-numbered paragraph A61, further including reflectively focussing to substantially focus an image of the light source adjacent to the light source.

A72. Some embodiments include the method according to alpha-numbered paragraph A61, wherein the reception optical axis is oriented to be at substantially a right angle to a direction of scanning, and the projection optical axis is oriented to be at substantially a forty-five-degree angle to the direction of scanning.

A73. One embodiment of the invention includes a machine-vision system for inspecting a device, the machine-vision system including: a light source for propagating light to the device; an image detector that receives light from the device; a light sensor assembly receiving a portion of the light from the light source, the light sensor assembly producing an output responsive to the intensity of the light received at the light sensor assembly; and a controller for controlling the amount of light received by the image detector, the controller controlling the amount of light within a desired range in response to the output from the light sensor.

A74. Some embodiments include the system of alpha-numbered paragraph A73 wherein the light sensor assembly further includes: a beam splitter positioned between the light source and the device; and a light sensor positioned to receive light from the beam splitter.

A75. Some embodiments include the system of alpha-numbered paragraph A74 wherein the beam splitter filters infrared light from the light source.

A76. Some embodiments include the system of alpha-numbered paragraph A73 further including a power supply which supplies power to the light source, the controller controlling the amount of light received by the image detector by controlling the amount of power output from the power supply.

A77. Some embodiments include the system of alpha-numbered paragraph A73 wherein the controller controls the amount of light received by the image detector by controlling the amount time the image detector receives light to acquire an image.

A78. Some embodiments include the system of alpha-numbered paragraph A73 wherein the image detector further includes an array of imaging pixels, wherein the controller controls the amount of light received by the image detector by controlling the amount time the array of imaging pixels receives light to acquire an image.

A79. Some embodiments include the system of alpha-numbered paragraph A78 further including a memory device which stores correction values for at least one of the pixels in the array of imaging pixels, wherein the value associated with the at least one of the pixels is corrected with a correction value stored in the memory.

A80. Some embodiments include the system of alpha-numbered paragraph A73 wherein the light sensor assembly further includes a photo diode.

A81. One embodiment of the invention includes a machine-vision system for inspecting a device, the machine-vision system including: a light source for propagating light to the device; an image detector that receives light from the device; and a cooling element attached to the imaging device, the cooling element removing heat produced by the image detector to keep the image detector within a selected temperature range.

A82. Some embodiments include the system of alpha-numbered paragraph A81, wherein the cooling element is a thermoelectric semiconductor unit.

A83. Some embodiments include the system of alpha-numbered paragraph A81, wherein the image detector is an array of imaging pixels.

A84. Some embodiments include the system of alpha-numbered paragraph A81, wherein the image detector is an array of semiconductor imaging pixels, the thermoelectric semiconductor unit further including: a temperature sensor for sensing the temperature of the array of semiconductor imaging pixels; a cool portion attached to the array of semiconductor imaging pixels to form a thermally conductive path between the array of semiconductor imaging pixels and the thermoelectric semiconductor unit; a heat rejection portion; and a controller for controlling the amount of power input to the thermoelectric semiconductor to keep the image detector within a selected temperature range.

A85. One embodiment of the invention includes a machine-vision system for inspecting a device, the machine-vision system including: a strobed light source for propagating light to the device; an image detector that receives light from the device, the image detector remaining in a fixed position with respect to the strobed light source; and translation element that moves the strobed light source and image detector with respect to the device.

A86. Some embodiments include the machine-vision system for inspecting a device of alpha-numbered paragraph A85 including a ring light source.

A87. Some embodiments include the machine-vision system for inspecting a device of alpha-numbered paragraph A85 further including a strobed light controller which controls the strobed light source to produce light having a first level and to produce light having a second level, the first level different from the first level.

A88. Some embodiments include the machine-vision system for inspecting a device of alpha-numbered paragraph A86 wherein the image detector further includes: an array of imaging pixels; and an imaging pixel controller which controls the amount of light received by the image detector by controlling the amount time the array of imaging pixels receives light to acquire an image.

A89. Some embodiments include the system of alpha-numbered paragraph A87 further including a memory device which stores correction values for at least one of the pixels in the array of imaging pixels, wherein the value associated with the at least one of the pixels is corrected with a correction value stored in the memory.

A90. Some embodiments include the system of alpha-numbered paragraph A87 further including a memory device which stores a first correction value associated with the first level of light from the strobed light source, and a second correction value associated with the second level of light from the strobed light source for at least one of the pixels in the array of imaging pixels, wherein the values associated with the at least one of the pixels is corrected with the first and second correction values stored in the memory.

A91. Some embodiments include the machine-vision system for inspecting a device of alpha-numbered paragraph A86 wherein the strobed light controller controls the strobed light source to produce light having a first level and alternated with light having a second level.

A92. Some embodiments include the machine-vision system for inspecting a device of alpha-numbered paragraph A86 including a strobed ring light source, the strobed light controller controlling the strobed light source and the strobed ring light source.

A93. Some embodiments include the machine-vision system for inspecting a device of alpha-numbered paragraph A92 wherein the strobed light controller controls the strobed ring light source to strobe alternatively with the strobed light at the first level and at the second level.

A94. Some embodiments include the machine-vision system for inspecting a device of alpha-numbered paragraph A86 wherein the image detector is included of a first line of pixels and a second line of pixels, the machine vision system further including a strobed ring light source, wherein the strobed light controller controls the strobed ring light source to produce light for the first line of pixels and the second line of pixels.

A95. One embodiment of the invention includes a method for acquiring physical information associated with of a device using a machine-vision station having a light source and having an image detector, the method including: projecting light from the light source to the device; receiving light reflected from the device into an image detector; and controlling the amount of light received at the image detector to a value within a desired range.

A96. Some embodiments include the method of alpha-numbered paragraph A95, wherein controlling the amount of light received at the image detector further includes: sensing the projected from the light source; and controlling the amount of power input to the light source in response to the value produced by the sensing step.

A97. Some embodiments include the method of alpha-numbered paragraph A95, wherein the image detector further includes an array of pixels which produce a signal dependent on the length of time the pixel is exposed to the reflected light, wherein the controlling the amount of light received at the image detector further includes sensing the projected from the light source; and controlling the length of time the image detector is exposed to reflected light in response to the value produced by the sensing step.

A98. Some embodiments include the method of alpha-numbered paragraph A95 wherein controlling the amount of light received at the image detector further includes sensing the reflected from the device and controlling the amount of power input to the light source in response to the value produced by the sensing step.

A99. Some embodiments include the method of alpha-numbered paragraph A24 wherein the image detector further includes an array of pixels which produce a signal dependent on the length of time the pixel is exposed to the reflected light, wherein controlling the amount of light received at the image detector further includes sensing the reflected from the device; and controlling the length of time the image detector is exposed to reflected light in response to the value produced by the sensing step.

A100. One embodiment of the invention includes a method for acquiring physical information associated with of a device using a machine-vision station having a light source and having an image detector, the method including projecting light from the light source to the device; receiving light reflected from the device into an image detector; and removing heat produced by the image detector to keep the image detector within a selected temperature range.

A101. Some embodiments include the method of alpha-numbered paragraph A29, wherein removing heat produced by the image detector further includes attaching a thermoelectric semiconductor unit to the image detector.

A102. One embodiment of the invention includes a method for acquiring physical information associated with of a device using a machine-vision station having a light source and having an image detector, the method including fixing the relationship between the light source and the image detector; moving the light source and the image detector with respect to the device; projecting strobed light from the light source to the device; and receiving light reflected from the device into an image detector.

A103. Some embodiments include the method of alpha-numbered paragraph A102 wherein the wherein projecting strobed light from the light source to the device further includes: producing a first level of strobed light from the light source; and producing a second level of strobed light from the light source.

A104. Some embodiments include the method of alpha-numbered paragraph A103 further including producing a strobed light from a ring light.

A115. Some embodiments include the method of alpha-numbered paragraph A104 wherein the wherein projecting strobed light from the light source to the device further includes: producing a first level of strobed light from the light source; producing a second level of strobed light from the light source; and alternating the strobed light of the first level with the strobed light of the second level.

A106. One embodiment of the invention includes a manufacturing system, including: a semiconductor part fabrication unit that fabricates a part for a semiconductor device; and an inspection station, the inspection station further including: (a) a light source projecting light onto the device; (b) an image detector which receives light reflected from the device, the image detector including a plurality of lines of semiconductor imaging pixels; (c) a light sensor assembly receiving a portion of the light from the light source, the light sensor assembly producing an output responsive to the intensity of the light received at the light sensor assembly; and (d) a controller for controlling the amount of light received by the image detector, the controller controlling the amount of light within a desired range in response to the output from the light sensor.

A107. Some embodiments include the manufacturing system of alpha-numbered paragraph A106 wherein the inspection station further includes memory for storing correction values associated with at least one of the pixels in the image detector.

A108. Some embodiments include the manufacturing system of alpha-numbered paragraph A106, wherein the inspection station further includes a light source controller for producing strobed light of a first level and strobed light of a second level.

A109. Some embodiments include the manufacturing system of alpha-numbered paragraph A108 wherein the inspection station further includes a ring light.

A110. Some embodiments include the manufacturing system of alpha-numbered paragraph A106 wherein the inspection station further includes: a ring light; and a ring light controller for strobing the ring light, the ring light controller strobing the ring light for each of the plurality of lines of pixels in the image detector.

A111. One embodiment of the invention includes a machine-vision system for inspecting at least one device, the machine-vision system including a first inspection station, the first inspection station including: a surface for inspecting at least one device, the surface having an opening therein; an inspection device positioned on one side of the inspection surface; and an elevator that places at least one device within the opening in the surface from another side of the inspection surface opposite the one side of the inspection surface, the elevator presenting at least one device to the surface for inspecting at least one device.

A112. Some embodiments include the system of alpha-numbered paragraph A111, wherein the elevator further includes a compartment for holding at least one device, the elevator placing at least one device within the opening in the surface and presenting the device to the surface for inspecting the device.

A113. Some embodiments include the system of alpha-numbered paragraph A112, the first inspection station further including: a light source that propagates light to the device when the device is positioned on the surface for inspecting the device; and an image detector that receives light from the device.

A114. Some embodiments include the system of alpha-numbered paragraph A112 wherein the elevator and the compartment for holding a at least one device is aligned with the opening.

A115. Some embodiments include the system of alpha-numbered paragraph A111 wherein the elevator is aligned with the opening.

A116. Some embodiments include the system of alpha-numbered paragraph A111 further including a first tray for holding at least one device; a first tray for holding at least one device; a tray-transfer mechanism; and a second inspection station, the tray-transfer mechanism operating to move at least one device from the first inspection station to a second inspection station.

A117. Some embodiments include the system of alpha-numbered paragraph A116 wherein the tray-transfer mechanism further includes an inverting mechanism inverts the first tray and the second tray so as to position the at least one device within the second tray so that another side of the at least one device can be inspected.

A118. Some embodiments include the system of alpha-numbered paragraph A116 wherein one side of the at least one device is inspected at the first inspection position and wherein another side of the at least one device is inspected at the second inspection position.

A119. Some embodiments include the system of alpha-numbered paragraph A117 further including: a third inspection station; and a fourth inspection station, the tray-transfer device moving the device between the first and third inspection stations, and between the second and fourth inspection stations.

A120. Some embodiments include the system of alpha-numbered paragraph A119 wherein the inverting mechanism is positioned between the third inspection station and the second inspection station.

A121. One embodiment of the invention includes a machine-vision system for inspecting a plurality of devices positioned within a plurality of device-carrying trays, the machine-vision system including: a first slide clamp adapted to hold a first tray and a second tray, the first slide clamp moving the first tray from a first inspection station to a second inspection station, and moving the second tray from the second inspection station to a flip station; and a second slide clamp adapted to hold a third tray and a fourth tray, the second slide clamp moving the third tray from the flip station to a third inspection station, and moving the fourth tray from the third inspection station to a fourth station.

A122. Some embodiments include the machine-vision system of alpha-numbered paragraph A121 wherein the first slide clamp has two openings therein, each opening sized to receive one of the first device-carrying tray, or the second device-carrying tray, the first slide clamp further including: a registration surface for registering the a surface of one of the first device-carrying tray, or the second device-carrying tray; and a clamp for clamping one of the first device-carrying tray, or the second device-carrying tray in a desired position, the clamp positioned to clamp one of the first device-carrying tray, or the second device-carrying tray with respect to the two openings in the first slide clamp.

A123. Some embodiments include the machine-vision system of alpha-numbered paragraph A121 further including a machine-vision inspection head for scanning the devices within one of the first device-carrying tray, or the second device-carrying tray at the first inspection station, the inspection head further including: a light source that propagates light to the device when positioned on the surface for inspecting the device; and an image detector that receives light from the device.

A124. Some embodiments include the machine-vision system of alpha-numbered paragraph A121 wherein the first tray and a second tray have a substantially rectangular footprint, and wherein the first slide clamp moves at least one of the first tray and the second tray in a direction substantially parallel to the short sides of the at least one of the first tray and the second tray.

A125. Some embodiments include the machine-vision system of alpha-numbered paragraph A124 further including a picker for picking devices which fail inspection from a tray.

A126. Some embodiments include the machine-vision system of alpha-numbered paragraph A125 further including a source of devices that have passed inspection, the picker substituting devices that have passed inspection for the devices that have failed inspection.

A127. Some embodiments include the machine-vision system of alpha-numbered paragraph A125 further including a source of devices that have passed inspection and have not passed inspection, the picker substituting devices that have passed inspection from the source for the devices that have failed inspection to produce a fourth tray filled with devices all of which have not passed inspection.

A128. Some embodiments include the machine-vision system of alpha-numbered paragraph A127 further including: a first location for the devices that have failed inspection; and a second location for devices that have not passed inspection.

A129. One embodiment of the invention includes a machine-vision system for inspecting a tray populated with a plurality of devices, the machine-vision system including: a first inspection station having a first inspection surface; a compartment positioned adjacent the first inspection station, the compartment holding a plurality of trays; and an elevator for elevating at least one of the trays from the compartment to the first inspection surface.

A130. Some embodiments include the machine-vision system for inspecting a tray populated with a plurality of devices of alpha-numbered paragraph A19 wherein the first inspection surface has an opening therein, the opening accommodating one of the plurality of trays.

A131. Some embodiments include the machine-vision system for inspecting a tray populated with a plurality of devices of alpha-numbered paragraph A129 wherein the first inspection surface has an opening therein, the opening accommodating one of the plurality of trays, the trays having a rectangular shape, the machine-vision system further including finger elements positioned near the opening, the finger elements engaging the long dimension side of the tray.

A132. Some embodiments include the machine-vision system for inspecting a tray populated with a plurality of devices of alpha-numbered paragraph A129 wherein the first inspection surface has an opening therein, the opening accommodating one of the plurality of trays, the trays having a rectangular shape, the machine-vision system further including finger elements positioned near the opening, the finger elements engaging the short dimension side of the tray.

A133. Some embodiments include the machine-vision system for inspecting a tray populated with a plurality of devices of alpha-numbered paragraph A128 further including a second inspection station having a second inspection surface; an elevator for moving at least one of the trays from the between a first position at the second inspection surface and a second position away from the second inspection surface.

A134. Some embodiments include the machine-vision system for inspecting a tray populated with a plurality of devices of alpha-numbered paragraph A129 wherein the compartment further includes: a door which folds from a closed position to an open position; a first guide rail positioned on the inner surface of the door; and a second guide rail positioned on the inner surface of the door, the first guide rail and the second guide rail spaced to receive at least one tray so that the tray can be placed between the first and second guide rails and guided into the compartment.

A135. One embodiment of the invention includes a machine-vision system for inspecting a tray populated with a plurality of devices, the machine-vision system including: an inspection station including an inspection surface; means for determining if at least one of the plurality of devices in a tray at the inspection station does not pass an inspection test; and a failed device station for holding trays which hold devices having devices which have passed inspection and devices which have not passed inspection at which trays are formed in which all of the plurality of devices do not pass inspection.

A136. Some embodiments include the machine-vision system for inspecting a tray populated with a plurality of devices of alpha-numbered paragraph A135 further including a first picker for moving at least one of the plurality of devices between the inspection station and the failed device station.

A137. Some embodiments include the machine-vision system for inspecting a tray populated with a plurality of devices of alpha-numbered paragraph A136 wherein the first picker for moving at least one of the plurality of devices between the inspection station and the failed device station accommodates differently spaced devices within trays.

A138. Some embodiments include the machine-vision system for inspecting a tray populated with a plurality of devices of alpha-numbered paragraph A136 further including a second picker for moving at least one of the plurality of devices between the inspection station and the failed device station.

A139. Some embodiments include the machine-vision system for inspecting a tray populated with a plurality of devices of alpha-numbered paragraph A138 wherein the first picker and the second picker for moving at least one of the plurality of devices between the inspection station and the failed device station accommodates differently spaced devices within trays.

A140. Some embodiments include the machine-vision system for inspecting a tray populated with a plurality of devices of alpha-numbered paragraph A135 further including a compartment near the failed device station for housing trays in which all of the plurality of devices do not pass inspection.

A141. One embodiment of the invention includes a machine-vision system for inspecting a rectangular tray populated with a plurality of devices, the machine-vision system including: an inspection station including an inspection surface; and means for holding the rectangular tray which engage the sides of the tray with the shorter dimension.

A142. Some embodiments include the machine-vision system for inspecting a tray populated with a plurality of devices of alpha-numbered paragraph A141 wherein means for holding the rectangular tray which engage the sides of the tray with the shorter dimension includes a set of pins which engage detents in the shorter side of the tray.

A143. Some embodiments include the machine-vision system for inspecting a tray populated with a plurality of devices of alpha-numbered paragraph A142 wherein the pins force the tray to a datum registration surface.

A144. Some embodiments include the machine-vision system for inspecting a tray populated with a plurality of devices of alpha-numbered paragraph A141 further including means for moving the rectangular tray in a direction substantially parallel to the shorter dimension of the rectangular tray.

A145. Some embodiments include the machine-vision system for inspecting a tray populated with a plurality of devices of alpha-numbered paragraph A144 further including means for inspecting the rectangular tray in a direction substantially parallel to the longer dimension of the rectangular tray.

A146. One embodiment of the invention includes a machine-vision system for inspecting a rectangular tray populated with a plurality of devices, the machine-vision system including: an inspection station including an inspection surface; a 3D inspection device; and a 2D inspection device.

A147. Some embodiments include the machine-vision system for inspecting a tray populated with a plurality of devices of alpha-numbered paragraph A146 wherein the 3D device and 2D device inspect the inspection surface synchronously.

A148. Some embodiments include the machine-vision system for inspecting a tray populated with a plurality of devices of alpha-numbered paragraph A147 wherein the inspection surface holds a first tray and a second tray.

A149. Some embodiments include the machine-vision system for inspecting a tray populated with a plurality of devices of alpha-numbered paragraph A146 wherein the 3D device and 2D device inspect the inspection surface asynchronously.

A150. Some embodiments include the machine-vision system for inspecting a tray populated with a plurality of devices of alpha-numbered paragraph A149 wherein the inspection surface holds a first tray and a second tray.

A151. One embodiment of the invention includes a method for acquiring physical information associated with a plurality of devices placed in a tray, the method including: loading at least one tray into a compartment adjacent a first inspection station; and elevating the tray to the first inspection surface.

A152. Some embodiments include the method of alpha-numbered paragraph A151 further including: inspecting a first side of at least one of a plurality of devices within a first tray; moving the first tray to a flip station; and inspecting a second side of at least one of a plurality of devices within the second tray.

A153. Some embodiments include the method of alpha-numbered paragraph A152, further including removing at least one of a plurality of devices from the second tray if the at least one of a plurality of devices fails inspection.

A154. Some embodiments include the method of alpha-numbered paragraph A152 further including replacing at least one of a plurality of devices in the second tray that failed inspection with a device that passed inspection.

A155. One embodiment of the invention includes a machine-vision system for inspecting a device, the machine-vision system including: an initial inspection station, the initial inspection station including: a surface for inspecting the device, the surface having an opening therein; and an elevator that places the device within the opening in the surface and presents the device to the surface for inspecting the device.

A156. Some embodiments include the system of alpha-numbered paragraph A155 wherein the elevator further includes a compartment for holding a plurality of devices, the elevator placing at least one of the plurality of devices within the opening in the surface and presenting the device to the surface for inspecting the device.

A157. Some embodiments include the system of alpha-numbered paragraph A156, the initial inspection station further including: a light source that propagates light to the device when the device is positioned on the surface for inspecting the device; and an image detector that receives light from the device.

A158. Some embodiments include the system of alpha-numbered paragraph A156 wherein the elevator and the compartment for holding a plurality of devices are aligned with the opening.

A159. Some embodiments include the system of alpha-numbered paragraph A155 wherein the elevator is aligned with the opening.

A160. Some embodiments include the system of alpha-numbered paragraph A155 further including a tray-transfer device that operates to move the device from the initial inspection station to a second inspection station.

A161. Some embodiments include the system of alpha-numbered paragraph A160 further including an inverting mechanism that operates to invert the device so that the another side of the device can be inspected.

A162. Some embodiments include the system of alpha-numbered paragraph A161 wherein one side of the device is inspected in the first inspection position and wherein another side of the device is inspected in the second inspection position.

A161. Some embodiments include the system of alpha-numbered paragraph A160 further including a third inspection station and a fourth inspection station, the tray-transfer device moving the device between the first and third inspection stations, and between the second and fourth inspection stations. A162. Some embodiments include the system of alpha-numbered paragraph A9 wherein the inverting mechanism is positioned between the third inspection position and the second inspection position.

A163. One embodiment of the invention includes a machine-vision system for inspecting a plurality of devices positioned within a plurality of device-carrying trays the machine-vision system including:

a first slide clamp for holding at least two trays, the slide clamp moving a first tray from a first inspection station to a second inspection station, and moving a second tray from the second inspection station to a flip station; and a second slide clamp for holding at least two trays, the slide clamp moving a third tray from the flip station to a third inspection station, and moving a fourth tray from the third inspection station to a fourth station.

A164. Some embodiments include the machine-vision system of alpha-numbered paragraph A163 wherein the first slide clamp has two openings therein, each opening sized to receive a device-carrying tray, the first slide clamp further including:

a registration surface for registering the a surface of the device-carrying tray; and a clamp for clamping the tray in a desired position, the clamp positioned to clamp the tray with respect to the opening in the slide clamp.

A165. Some embodiments include the machine-vision system of alpha-numbered paragraph A163 further including a machine-vision inspection head for scanning the devices within the trays at the first inspection station, the inspection head further including: a light source that propagates light to the device when positioned on the surface for inspecting the device; and an image detector that receives light from the device.

A166. Some embodiments include the machine-vision system of alpha-numbered paragraph A163 wherein the flip station further includes a mechanism for flipping the devices carried in a tray, the mechanism further including: a first jaw having a surface for receiving a tray; a second jaw having a surface for receiving a tray; a mover for moving the first jaw, a first tray having a plurality of devices, a second tray, and the second jaw into engagement with each other, the first tray associated with the first jaw and the second tray associated with the second jaw; and a rotator for rotating the first and second jaw.

A167. Some embodiments include the machine-vision system of alpha-numbered paragraph A166 wherein the mover moves the first jaw in a direction substantially perpendicular to the surface for receiving a tray associated with the first jaw.

A168. Some embodiments include the machine-vision system of alpha-numbered paragraph A166 wherein the mover moves the first jaw and the second jaw in a direction substantially perpendicular to the surface for receiving a tray associated with the first jaw.

A169. Some embodiments include the machine-vision system of alpha-numbered paragraph A166 further including a picker for picking devices which fail inspection from a tray.

A170. Some embodiments include the machine-vision system of alpha-numbered paragraph A168 further including a source of devices that have passed inspection, the picker substituting devices that have passed inspection for the devices that have failed inspection.

A171. One embodiment of the invention includes a machine-vision system for inspecting a plurality of devices and for transferring the plurality of devices from being positioned in a first tray to being positioned in a second tray, the machine-vision system including: a first jaw having a surface for receiving the first tray; a second jaw having a surface for receiving the second tray; a mover for moving the first jaw, the first tray having a plurality of devices, the second tray, and the second jaw into engagement with each other, the first tray associated with the first jaw and the second tray associated with the second jaw; and a rotator for rotating the first and second jaw.

A172. Some embodiments include the machine-vision system of alpha-numbered paragraph A171 further including: a first conveyer for moving the first tray having a plurality of devices therein to the surface of the first jaw; and a second conveyer for moving the second tray having a plurality of devices therein from surface of the second jaw.

A173. Some embodiments include the machine-vision system of alpha-numbered paragraph A172 wherein one of the first or second jaws is capable of holding, in any position, a tray devoid of devices.

A174. One embodiment of the invention includes a machine-vision system for inspecting a tray populated with a plurality of devices, the machine-vision system including: a first inspection station having a first inspection surface; a compartment positioned adjacent the first inspection station, the compartment holding a plurality of trays; and an elevator for elevating at least one of the trays from the compartment to the first inspection surface.

A175. Some embodiments include the machine-vision system for inspecting a tray populated with a plurality of devices of alpha-numbered paragraph A174 wherein the first inspection surface has an opening therein, the opening accommodating one of the plurality of trays.

A176. Some embodiments include the machine-vision system for inspecting a tray populated with a plurality of devices of alpha-numbered paragraph A174 wherein the first inspection surface has an opening therein, the opening accommodating one of the plurality of trays, the trays having a rectangular shape, the machine-vision system further including finger elements positioned near the opening, the finger elements engaging the long dimension side of the tray.

A177. Some embodiments include the machine-vision system for inspecting a tray populated with a plurality of devices of alpha-numbered paragraph A174 wherein the first inspection surface has an opening therein, the opening accommodating one of the plurality of trays, the trays having a rectangular shape, the machine-vision system further including finger elements positioned near the opening, the finger elements engaging the short dimension side of the tray.

A178. Some embodiments include the machine-vision system for inspecting a tray populated with a plurality of devices of alpha-numbered paragraph A174 further including a second inspection station having a second inspection surface; an elevator for moving at least one of the trays from the between a first position at the second inspection surface and a second position away from the second inspection surface.

A179. Some embodiments include the machine-vision system for inspecting a tray populated with a plurality of devices of alpha-numbered paragraph A22 wherein the compartment further includes: a door which folds from a closed position to an open position; a first guide rail positioned on the inner surface of the door; a second guide rail positioned on the inner surface of the door, the first guide rail and the second guide rail spaced to receive at least one tray so that the tray can be placed between the first and second guide rails and guided into the compartment.

A180. One embodiment of the invention includes a method for acquiring physical information associated with a plurality of devices placed in a tray, the method including loading at least one tray into a compartment adjacent a first inspection station; and elevating the tray to the first inspection surface.

A181. Some embodiments include the method of alpha-numbered paragraph A180 further including inspecting a first side of a device within a first tray; moving the tray to a flip station; flipping the devices and placing the flipped devices within a second tray; and inspecting a second side of the device within the second tray.

A182. Some embodiments include the method of alpha-numbered paragraph A181, further including removing a device from the second tray if it fails inspection.

A183. Some embodiments include the method of alpha-numbered paragraph A181, further including replacing a device in the second tray that failed inspection with a device that passed inspection.

A184. One embodiment of the invention includes a machine-vision system for inspecting a plurality of devices and for inverting the plurality of devices from being positioned in a first tray, the machine-vision system including: a first jaw having a surface for receiving the first tray; a second jaw having a surface; a mover for moving the first jaw, the first tray having a plurality of devices, and the second jaw into engagement with each other, the first tray associated with the first jaw; and a rotator for rotating the first and second jaw.

A185. Some embodiments include the machine-vision system of alpha-numbered paragraph A184 further including: a first conveyer for moving the first tray having a plurality of devices therein to the first jaw; and a second conveyer for moving the first tray having a plurality of devices therein from the first jaw.

A186. Some embodiments include the machine-vision system of alpha-numbered paragraph A184 wherein the first jaw is capable of holding, in any position, a tray devoid of devices.

A187. Some embodiments include the machine-vision system of alpha-numbered paragraph A184 further including: a slider for transferring the inverted devices from the second jaw into the first tray.

A188. One embodiment of the invention includes a machine-vision system for inspecting at least one device, the machine-vision system including: a first inspection station, wherein the first inspection station includes a surface for inspecting at least one device, the surface having an opening therein; an inspection device positioned on one side of the inspection surface; and an elevator that places at least one device within the opening in the surface from another side of the inspection surface opposite the one side of the inspection surface, the elevator presenting at least one device to the surface for inspecting at least one device.

A189. Some embodiments include the system of alpha-numbered paragraph A188 wherein the elevator further includes a compartment for holding at least one device, the elevator placing at least one device within the opening in the surface and presenting the device to the surface for inspecting the device.

A190. Some embodiments include the system of alpha-numbered paragraph A189, the first inspection station further including a light source that propagates light to the device when the device is positioned on the surface for inspecting the device; and an image detector that receives light from the device.

A191. Some embodiments include the system of alpha-numbered paragraph A189 wherein the elevator and the compartment for holding a at least one device is aligned with the opening.

A192. Some embodiments include the system of alpha-numbered paragraph A188 wherein the elevator is aligned with the opening.

A193. Some embodiments include the system of alpha-numbered paragraph A188 further including a first tray for holding at least one device; a first tray for holding at least one device; a tray-transfer mechanism; and a second inspection station, the tray-transfer mechanism operating to move at least one device from the first inspection station to a second inspection station.

A194. Some embodiments include the system of alpha-numbered paragraph A193 wherein the tray-transfer mechanism further includes an inverting mechanism inverts the first tray and the second tray so as to position the at least one device within the second tray so that another side of the at least one device can be inspected.

A195. Some embodiments include the system of alpha-numbered paragraph A193 wherein one side of the at least one device is inspected at the first inspection position and wherein another side of the at least one device is inspected at the second inspection position.

A196. Some embodiments include the system of alpha-numbered paragraph A194 further including a third inspection station; and a fourth inspection station, the tray-transfer device moving the device between the first and third inspection stations, and between the second and fourth inspection stations.

A197. Some embodiments include the system of alpha-numbered paragraph A195 wherein the inverting mechanism is positioned between the third inspection station and the second inspection station.

A198. One embodiment of the invention includes a machine-vision system for inspecting a plurality of devices positioned within a plurality of device-carrying trays, the machine-vision system including: a first slide clamp adapted to hold a first tray and a second tray, the first slide clamp moving the first tray from a first inspection station to a second inspection station, and moving the second tray from the second inspection station to a flip station; and a second slide clamp adapted to hold a third tray and a fourth tray, the second slide clamp moving the third tray from the flip station to a third inspection station, and moving the fourth tray from the third inspection station to a fourth station.

A199. Some embodiments include the machine-vision system of alpha-numbered paragraph A198 wherein the first slide clamp has two openings therein, each opening sized to receive one of the first device-carrying tray, or the second device-carrying tray, the first slide clamp further including: a registration surface for registering the a surface of one of the first device-carrying tray, or the second device-carrying tray; and a clamp for clamping one of the first device-carrying tray, or the second device-carrying tray in a desired position, the clamp positioned to clamp one of the first device-carrying tray, or the second device-carrying tray with respect to the two openings in the first slide clamp.

A200. Some embodiments include the machine-vision system of alpha-numbered paragraph A198 further including a machine-vision inspection head for scanning the devices within one of the first device-carrying tray, or the second device-carrying tray at the first inspection station, the inspection head further including: a light source that propagates light to the device when positioned on the surface for inspecting the device; and an image detector that receives light from the device.

A201. Some embodiments include the machine-vision system of alpha-numbered paragraph A198 wherein the first tray and a second tray have a substantially rectangular footprint, and wherein the first slide clamp moves at least one of the first tray and the second tray in a direction substantially parallel to the short sides of the at least one of the first tray and the second tray.

A202. Some embodiments include the machine-vision system of alpha-numbered paragraph A201 further including a picker for picking devices which fail inspection from a tray.

A203. Some embodiments include the machine-vision system of alpha-numbered paragraph A202 further including a source of devices that have passed inspection, the picker substituting devices that have passed inspection for the devices that have failed inspection.

A204. Some embodiments include the machine-vision system of alpha-numbered paragraph A202 further including a source of devices that have passed inspection and have not passed inspection, the picker substituting devices that have passed inspection from the source for the devices that have failed inspection to produce a fourth tray filled with devices all of which have not passed inspection.

A205. Some embodiments include the machine-vision system of alpha-numbered paragraph A204 further including: a first location for the devices that have failed inspection; and a second location for devices that have not passed inspection.

A206. One embodiment of the invention includes a machine-vision system for inspecting a tray populated with a plurality of devices, the machine-vision system including: a first inspection station having a first inspection surface; a compartment positioned adjacent the first inspection station, the compartment holding a plurality of trays; and an elevator for elevating at least one of the trays from the compartment to the first inspection surface.

A207. Some embodiments include the machine-vision system for inspecting a tray populated with a plurality of devices of alpha-numbered paragraph A206 wherein the first inspection surface has an opening therein, the opening accommodating one of the plurality of trays.

A208. Some embodiments include the machine-vision system for inspecting a tray populated with a plurality of devices of alpha-numbered paragraph A206 wherein the first inspection surface has an opening therein, the opening accommodating one of the plurality of trays, the trays having a rectangular shape, the machine-vision system further including finger elements positioned near the opening, the finger elements engaging the long dimension side of the tray.

A209. Some embodiments include the machine-vision system for inspecting a tray populated with a plurality of devices of alpha-numbered paragraph A206 wherein the first inspection surface has an opening therein, the opening accommodating one of the plurality of trays, the trays having a rectangular shape, the machine-vision system further including finger elements positioned near the opening, the finger elements engaging the short dimension side of the tray.

A210. Some embodiments include the machine-vision system for inspecting a tray populated with a plurality of devices of alpha-numbered paragraph A208 further including a second inspection station having a second inspection surface; an elevator for moving at least one of the trays from the between a first position at the second inspection surface and a second position away from the second inspection surface.

A211. Some embodiments include the machine-vision system for inspecting a tray populated with a plurality of devices of alpha-numbered paragraph A19 wherein the compartment further includes: a door which folds from a closed position to an open position; a first guide rail positioned on the inner surface of the door; and a second guide rail positioned on the inner surface of the door, the first guide rail and the second guide rail spaced to receive at least one tray so that the tray can be placed between the first and second guide rails and guided into the compartment.

A212. One embodiment of the invention includes a machine-vision system for inspecting a tray populated with a plurality of devices, the machine-vision system including: an inspection station including an inspection surface; means for determining if at least one of the plurality of devices in a tray at the inspection station does not pass an inspection test; and a failed device station for holding trays which hold devices having devices which have passed inspection and devices which have not passed inspection at which trays are formed in which all of the plurality of devices do not pass inspection.

A213. Some embodiments include the machine-vision system for inspecting a tray populated with a plurality of devices of alpha-numbered paragraph A212 further including a first picker for moving at least one of the plurality of devices between the inspection station and the failed device station.

A214. Some embodiments include the machine-vision system for inspecting a tray populated with a plurality of devices of alpha-numbered paragraph A213 wherein the first picker for moving at least one of the plurality of devices between the inspection station and the failed device station accommodates differently spaced devices within trays.

A215. Some embodiments include the machine-vision system for inspecting a tray populated with a plurality of devices of alpha-numbered paragraph A212 further including a second picker for moving at least one of the plurality of devices between the inspection station and the failed device station.

A216. Some embodiments include the machine-vision system for inspecting a tray populated with a plurality of devices of alpha-numbered paragraph A215 wherein the first picker and the second picker for moving at least one of the plurality of devices between the inspection station and the failed device station accommodates differently spaced devices within trays.

A217. Some embodiments include the machine-vision system for inspecting a tray populated with a plurality of devices of alpha-numbered paragraph A215 further including a compartment near the failed device station for housing trays in which all of the plurality of devices do not pass inspection.

A218. One embodiment of the invention includes a machine-vision system for inspecting a rectangular tray populated with a plurality of devices, the machine-vision system including: an inspection station including an inspection surface; and a holder mechanism that holds the rectangular tray and engages the sides of the tray with the shorter dimension.

A219. Some embodiments include the machine-vision system for inspecting a tray populated with a plurality of devices of alpha-numbered paragraph A218 wherein means for holding the rectangular tray which engage the sides of the tray with the shorter dimension includes a set of pins which engage detents in the shorter side of the tray.

A220. Some embodiments include the machine-vision system for inspecting a tray populated with a plurality of devices of alpha-numbered paragraph A219 wherein the pins force the tray to a datum registration surface.

A221. Some embodiments include the machine-vision system for inspecting a tray populated with a plurality of devices of alpha-numbered paragraph A218 further including means for moving the rectangular tray in a direction substantially parallel to the shorter dimension of the rectangular tray.

A222. Some embodiments include the machine-vision system for inspecting a tray populated with a plurality of devices of alpha-numbered paragraph A34 further including means for inspecting the rectangular tray in a direction substantially parallel to the longer dimension of the rectangular tray.

A223. One embodiment of the invention includes a machine-vision system for inspecting a rectangular tray populated with a plurality of devices, the machine-vision system including: an inspection station including an inspection surface; a 3D inspection device; and a 2D inspection device.

A224. Some embodiments include the machine-vision system for inspecting a tray populated with a plurality of devices of alpha-numbered paragraph A223 wherein the 3D device and 2D device inspect the inspection surface synchronously.

A225. Some embodiments include the machine-vision system for inspecting a tray populated with a plurality of devices of alpha-numbered paragraph A224 wherein the inspection surface holds a first tray and a second tray.

A226. Some embodiments include the machine-vision system for inspecting a tray populated with a plurality of devices of alpha-numbered paragraph A225 wherein the 3D device and 2D device inspect the inspection surface asynchronously.

A227. Some embodiments include the machine-vision system for inspecting a tray populated with a plurality of devices of alpha-numbered paragraph A226 wherein the inspection surface holds a first tray and a second tray.

A228. One embodiment of the invention includes a method for acquiring physical information associated with a plurality of devices placed in a tray, the method including: loading at least one tray into a compartment adjacent a first inspection station; and elevating the tray to the first inspection surface.

A229. Some embodiments include the method of alpha-numbered paragraph A228 further including: inspecting a first side of at least one of a plurality of devices within a first tray; moving the first tray to a flip station; and inspecting a second side of at least one of a plurality of devices within the second tray.

A230. Some embodiments include the method of alpha-numbered paragraph A229, further including removing at least one of a plurality of devices from the second tray if the at least one of a plurality of devices fails inspection.

A231. Some embodiments include the method of alpha-numbered paragraph A229, further including replacing at least one of a plurality of devices in the second tray that failed inspection with a device that passed inspection.

A232. One embodiment of the invention includes a machine-vision system for inspecting a device, the machine-vision system including: a light source that propagates light to the device; a pattern that generates a moire pattern; an image detector that receives light from the device; a light-sensor assembly that receives a portion of the light from the light source and that produces an output responsive to the intensity of the light received at the light-sensor assembly; and a computer and comparison system for manipulating a plurality of outputs from the light-sensor.

A233. Some embodiments include the system of alpha-numbered paragraph A232 wherein the computer and comparison system for manipulating a plurality of outputs from the light-sensor is of sufficient granularity to allow the data obtained to be manipulated to detect various features.

A234. Some embodiments include the system of alpha-numbered paragraph A233 wherein the data can be used to determine coplanarity of features on a device.

A235. Some embodiments include the system of alpha-numbered paragraph A233 wherein the data can be used to determine warpage of a subtrate on a device.

A236. Some embodiments include the system of alpha-numbered paragraph A233 wherein the data can be used to locate random features on a device.

A237. Some embodiments include the system of alpha-numbered paragraph A233 wherein the data can be used to locate features on a device that is randomly situated.

A238. Some embodiments include the system of alpha-numbered paragraph A233 further including: a mover that moves the light source and the device with respect to one another, and a detector that detects the velocity of a the light source with respect to the device.

A239. Some embodiments include the system of alpha-numbered paragraph A238 further including a linear postion encoder for specifying the times at which line scans are taken.

A240. Some embodiments include the system of alpha-numbered paragraph A239 wherein the computer and comparison system measures the distance over which a portion of the device moves over one or more line scans and determines the velocity of the device.

A241. Some embodiments include the system of alpha-numbered paragraph A233 wherein the pattern for generating the moire pattern includes a projection pattern element having a sine-wave element at the light source.

A242. Some embodiments include the system of alpha-numbered paragraph A233 wherein the pattern for generating the moire pattern includes: a first striped pattern; and a second striped pattern, the first striped pattern parallel to and offset from the plane of the second striped pattern, the first striped pattern and the second striped pattern positioned between the light source and the device.

A243. One embodiment of the invention includes a method for acquiring physical information associated with of a device using a machine-vision station having a light source and having an image detector, the method including: projecting light from the light source to the device; producing a moire pattern at the device; gathering data with sufficient granularity such that a device can be randomly placed on an inspection surface for gathering data; and manipulating the gathered data with a computer and comparator to identify various features of the device.

A244. One embodiment of the invention includes a method for acquiring physical information associated with of a device using a machine-vision station having a light source and having an image detector, the method including: projecting light from the light source to the device; producing a moire pattern at the device; gathering data with sufficient granularity such that data can be gathered on randomly placed features on the device positioned on an inspection surface; and manipulating the gathered data with a computer and comparator to identify various features of the device.

A245. Some embodiments include the method of alpha-numbered paragraph A244 wherein manipulating the data can be used to determine coplanarity of a plurality of points on the device.

A246. Some embodiments include the method of alpha-numbered paragraph A244 wherein manipulating the data can be used to determine position of a fiducial mark on a device at two separate times, the method further including calculating the velocity of the device with respect to the light source using the measured position and time.

A247. Some embodiments include the method of alpha-numbered paragraph A244 wherein manipulating the data can be used to determine position of a feature on a device at a first scan time and at a second scan time, the method further including: encoding the position of the feature at the first scan time; encoding the position of the feature at the second scan time; and calculating the velocity of the device with respect to the light source using the measured position and time.

A248. One embodiment of the invention includes a machine-vision head for inspecting a device, including: (a) a pattern projector to provide projected illumination, the pattern projector including: a light source, the light source providing light propagating generally along a projection optical axis, the projection optical axis intersecting the device when the machine-vision head is in operation; a projection pattern element that spatially modulates the light and located so that the projection optical axis intersects the projection pattern element; and a pattern projector imaging element located so that the projection optical axis intersects the pattern projector imaging element; and (b) an imager, the imager having a reception optical axis, the reception optical axis intersecting the device when the machine-vision head is in operation, the imager maintained in a substantially fixed relationship to the pattern projector, the imager including at least three lines of semiconductor imaging pixels; wherein a major plane of the projection pattern element, a major plane of the pattern projector imaging element, and a third plane are tilted one to another to substantially satisfy Schiempflug's condition that these three planes intersect at substantially one line.

A249. Some embodiments include the machine-vision head of alpha-numbered paragraph A248, wherein the third plane contains the reception optical axis or lies substantially parallel to the reception optical axis.

A250. Some embodiments include the machine-vision head of alpha-numbered paragraph A248, wherein the projection pattern element is maintained in a substantially fixed relationship to both the pattern projector and the imager when the machine-vision head is in operation.

A251. Some embodiments include the machine-vision head of alpha-numbered paragraph A2481, wherein the pattern projection element includes a pattern whose intensity along a line segment varies as a sine wave.

A252. One embodiment of the invention includes a machine-vision system for inspecting a device, including: (I) an inspection station, the inspection station including: (a) a pattern projector, the pattern projector including a light source, the light source providing light propagating generally along a projection optical axis, the projection optical axis intersecting the device when the inspection station is in operation, a projection pattern element that spatially modulates the light and located so that the projection optical axis intersects the projection pattern element, and a pattern projector imaging element located so that the projection optical axis intersects the pattern projector imaging element; and (b) an imager, the imager having a reception optical axis, the reception optical axis intersecting the device when the inspection station is in operation, the imager maintained in a substantially fixed relationship to the pattern projector, the imager including at least three lines of semiconductor imaging pixels; wherein a major plane of the projection pattern element, a major plane of the pattern projector imaging element, and a third plane are tilted one to another to substantially satisfy Schiempflug's condition that these three planes intersect at substantially one line, and wherein the imager provides acquired three-dimensional device geometry data regarding the device; (2) a comparator coupled to the imager, the comparator comparing one or more characteristics of the acquired three-dimensional device geometry data with an intended predetermined geometry to produce a signal indicative of any device geometry departure of an actual device geometry from the intended predetermined geometry.

A253. Some embodiments include the system of alpha-numbered paragraph A252, wherein the third plane contains the reception optical axis or lies substantially parallel to the reception optical axis.

A254. Some embodiments include the system of alpha-numbered paragraph A252, wherein the projection pattern element is maintained in a substantially fixed relationship to both the pattern projector and the imager when the inspection station is in operation.

A255. Some embodiments include the system of alpha-numbered paragraph A252, i wherein the pattern projection element includes a pattern whose intensity along a line segment varies as a sine wave.

A256. One embodiment of the invention includes a method for high-speed scanning phase measurement of a device at a machine-vision station to acquire physical information associated with the device, the method including: projecting light generally along a projection optical axis, the projection optical axis intersecting the device; spatially modulating the light with a projection pattern located so that the projection optical axis intersects the projection pattern; and imaging the spatially modulated light onto the device; and receiving light reflected from the device along a reception optical axis with an imager maintained in a substantially fixed relationship to the projected spatially modulated light, the imager including at least three lines of semiconductor imaging pixels, the reception optical axis intersecting the device; generating data representing acquired three-dimensional device geometry data regarding the device from signals from the imager; wherein spatially modulating and imaging the spatially modulated light provide a light pattern that is focused along a region of a third plane, wherein one of the at least three lines of semiconductor imaging pixels lies substantially within the third plane, and wherein a plane associated with the spatially modulating and a plane associated with the imaging the spatially modulated light, and a third plane are tilted one to another to substantially satisfy Schiempflug's condition that these three planes intersect at substantially one line, and wherein the reception optical axis lies within the third plane or is substantially parallel to the third plane.

A257. Some embodiments include the method of alpha-numbered paragraph A256, wherein spatially modulating includes modulating with a pattern whose intensity along a line segment varies as a sine wave.

A258. Some embodiments include the method of alpha-numbered paragraph A256, further including comparing the acquired three-dimensional device geometry data with an intended predetermined geometry to produce a signal indicative of any device geometry departure of an actual device geometry from the intended predetermined geometry; and controlling a manufacturing operation of the device to compensate for the device-geometry departure.

A259. One embodiment of the invention includes a machine-vision head for inspecting a device, including: (a) a pattern projector, the pattern projector including: a light source, the light source providing light propagating generally along a projection optical axis, the projection optical axis intersecting the device when the machine-vision head is in operation; a projection pattern element that spatially modulates the light and located so that the projection optical axis intersects the projection pattern element; and a pattern projector imaging element located so that the projection optical axis intersects the pattern projector imaging element; and (b) an imager, the imager having a reception optical axis, the reception optical axis intersecting the device when the machine-vision head is in operation, the imager including: at least three lines of semiconductor imaging pixels; and a telecentric imaging element that focusses an image of the device onto the at least three lines of semiconductor imaging pixels.

A260. One embodiment of the invention includes a method for high speed, scanning phase measurement of a device at a machine-vision station to acquire physical information associated with the device, the method including: projecting light generally along a projection optical axis, the projection optical axis intersecting the device when the machine-vision head is in operation; spatially modulating the light with a projection pattern located so that the projection optical axis intersects the projection pattern; imaging the spatially modulated light onto the device; receiving light reflected from the device into an imager, the imager having a reception optical axis, the reception optical axis intersecting the device, the imager maintained in a substantially fixed relationship to the pattern projector, the imager including three lines of semiconductor imaging pixels, wherein receiving includes telecentrically focussing an image of the device onto the at least three lines of semiconductor imaging pixels; and generating data representing acquired three-dimensional device geometry data regarding the device.

A261. Some embodiments include the method of alpha-numbered paragraph A260, further including: comparing the acquired three-dimensional device geometry data with an intended predetermined geometry to produce a signal indicative of any device geometry departure of an actual device geometry from the intended predetermined geometry; and controlling a manufacturing operation of the device to compensate for the device geometry departure, and wherein spatially modulating includes modulating with a projection pattern whose intensity along a line segment varies as a sine wave.

A262. Some embodiments include the method of alpha-numbered paragraph A260, further including: blocking an infra-red component of the light.

A263. One embodiment of the invention includes a machine-vision head for inspecting a device, including: (a) a pattern projector, the pattern projector including a light source, the light source providing light propagating generally along a projection optical axis, the projection optical axis intersecting the device when the machine-vision head is in operation, a projection pattern element that spatially modulates the light and located so that the projection optical axis intersects the projection pattern element, and a telecentric pattern projector imaging element that focusses an image of projection pattern element onto the device when the machine-vision head is in operation, and located so that the projection optical axis intersects the pattern projector imaging element; and (b) an imager, the imager having a reception optical axis, the reception optical axis intersecting the device when the machine-vision head is in operation.

A264. Some embodiments include the machine-vision head of alpha-numbered paragraph A263, wherein the imager further includes at least three lines of semiconductor imaging pixels, and wherein a major plane of the projection pattern element, a major plane of the pattern projector imaging element, and a third plane are tilted one to another to substantially satisfy Schiempflug's condition that these three planes intersect at substantially one line.

A265. One embodiment of the invention includes a machine-vision system for inspecting a device, the device having a first side and a second side, the machine-vision system including: a first inspection station for inspecting a first side of a device; a second inspection station for inspecting a second side of a device; and a tray-transfer device that operates to move the device from the first inspection station to the second inspection station, the tray-transfer device further including an inverting mechanism that operates to invert the device so that the first second side of the device can be inspected at the first inspection station and the second side of the device can be inspected at the second inspection station.

A266. Some embodiments include the system of alpha-numbered paragraph A265 wherein the inverting mechanism is positioned between the first inspection position and the second inspection position.

A267. Some embodiments include the machine-vision system of alpha-numbered paragraph A265 wherein the inverting mechanism further includes a mechanism for flipping the devices carried in a tray, the mechanism further including: a first jaw having a surface for receiving a first tray; a second jaw having a surface for receiving a second tray; a mover for moving the first jaw, the first tray having a plurality of devices, the second tray, and the second jaw into engagement with each other, the first tray associated with the first jaw and the second tray associated with the second jaw; and a rotator for rotating the first and second jaw.

A268. Some embodiments include the machine-vision system of alpha-numbered paragraph A267 wherein the mover moves the first jaw in a direction substantially perpendicular to the surface for receiving a tray associated with the first jaw.

A269. Some embodiments include the machine-vision system of alpha-numbered paragraph A267 wherein the mover moves the first jaw and the second jaw in a direction substantially perpendicular to the surface for receiving a tray associated with the first jaw.

A270. Some embodiments include the machine-vision system of alpha-numbered paragraph A267 wherein the inverting mechanism moves the plurality of devices to the second tray such that the second sides of a plurality of devices are presented for inspection.

A271. Some embodiments include the machine-vision system of alpha-numbered paragraph A267 wherein the rotator of the inverting mechanism moves the plurality of devices to the second tray such that the second sides of a plurality of devices are presented for inspection.

A272. Some embodiments include the machine-vision system of alpha-numbered paragraph A271 wherein the mover of the inverting mechanism is adapted to place the plurality of devices in the second tray at the second inspection station.

A273. Some embodiments include the machine-vision system of alpha-numbered paragraph A272 wherein the tray transfer device includes means for moving the second inspection station with respect to the inverting mechanisim.

A274. Some embodiments include the machine-vision system of alpha-numbered paragraph A273 further including a picker for picking devices which fail inspection from the second tray.

A275. One embodiment of the invention includes a machine-vision system for inspecting a plurality of devices positioned within a plurality of device-carrying trays, the machine-vision system including: a first tray adapted to carry a plurality of devices; a second tray adapted to carry a plurality of devices; a flip station for flipping the plurality of devices carried in a first tray from a first inspection position in the first tray to a second inspection position in the second tray.

A276. Some embodiments include the machine-vision system of alpha-numbered paragraph A275 wherein the flip station further includes: a first jaw having a surface for receiving a first tray; a second jaw having a surface for receiving a tray; a mover for moving the first jaw, a first tray having a plurality of devices, a second tray, and the second jaw into engagement with each other, the first tray associated with the first jaw and the second tray associated with the second jaw; and a rotator for rotating the first and second jaw.

A277. Some embodiments include the machine-vision system of alpha-numbered paragraph A276 further including:

a first slide clamp for holding at least the first tray, the first slide clamp moving the first tray from a first inspection station to a flip station; and a second slide clamp for holding at least the second tray, the second slide clamp moving the second tray from the flip station to the second inspection station.

A278. Some embodiments include the machine-vision system of alpha-numbered paragraph A275 wherein the flip station further includes a mechanism for flipping the devices carried in a tray, the mechanism further including means for limiting the motion of the rotator.

A279. Some embodiments include the machine-vision system of alpha-numbered paragraph A276 wherein the mover moves the first jaw in a direction substantially perpendicular to the surface for receiving a tray associated with the first jaw.

A280. Some embodiments include the machine-vision system of alpha-numbered paragraph A276 wherein the mover moves the first jaw and the second jaw in a direction substantially perpendicular to the surface for receiving a tray associated with the first jaw.

A281. One embodiment of the invention includes a flipping mechanism for transferring a plurality of devices from a position in a first tray to a position in a second tray, the flipping mechanism including: a first jaw having a surface adapted to receive the first tray; a second jaw having a surface adapted to receive the second tray; a mover for moving the first jaw, the first tray, the second tray, and the second jaw into engagement with each other, the first tray associated with the first jaw and the second tray associated with the second jaw; and a rotator for rotating the first and second jaw.

A282. Some embodiments include the machine-vision system of alpha-numbered paragraph A281 wherein the mover can be controlled to remove the first tray from a first inspection surface.

A283. Some embodiments include the machine-vision system of alpha-numbered paragraph A281 wherein the mover can be controlled to place the second tray at a second inspection surface.

A284. One embodiment of the invention includes a method for acquiring physical information associated with a plurality of devices placed in a tray, the method including: inspecting a first side of a device within a first tray; removing the first tray from a first surface and placing the first tray at a flip station; moving a second tray to a position near the first tray; flipping the first tray and second tray to move the device from the first tray to the second tray and place the device in the second tray so that a second side of the device is presented in the second tray; and inspecting a second side of the device within the second tray.

A285. Some embodiments include the method of alpha-numbered paragraph A284, further including moving the second tray to a second inspection surface.

A286. One embodiment of the invention includes a machine-vision system for inspecting a plurality of devices and for inverting the plurality of devices from being positioned in a first tray, the machine-vision system including: a first jaw having a surface for receiving the first tray; a second jaw having a surface; a mover for moving the first jaw, the first tray having a plurality of devices, and the second jaw into engagement with each other, the first tray associated with the first jaw; and a rotator for rotating the first and second jaw.

A287. Some embodiments include the machine-vision system of alpha-numbered paragraph A286 further including: a first conveyer for moving the first tray having a plurality of devices therein to the first jaw; and a second conveyer for moving the first tray having a plurality of devices therein from the first jaw.

A288. Some embodiments include the machine-vision system of alpha-numbered paragraph A286 wherein the first jaw is capable of holding, in any position, a tray devoid of devices.

A289. Some embodiments include the machine-vision system of alpha-numbered paragraph A286 further including: a slider for transferring the inverted devices from the second jaw into the first tray.

with current vision inspection systems. A feedback loop is used to control the intensity of the light received at a light receiver. This reduces the variability of the light intensity received at the light receiver. This eases the task of correlating signals generated by the receiver. Within a CCD the individual sources of light may be controlled to control the gain and bias resulting from manufacturing variances. This also eases the task of correlating data obtained from one sensor or another sensor since light of different intensities is not being produced by the source. A thermoelectric device is added to the light receiver to moderate temperature changes. This reduces signal shift or variation. An infrared filter in the path before the sensor also aids in keeping the signal from the sensor correlatable since the effects of IR light are reduced. In addition, the source of light is strobed to eliminate blurred or smeared images.

It is to be understood that the above description is intended to be illustrative, and not restrictive. Many other embodiments will be apparent to those of skill in the art upon reviewing the above description. The scope of the invention should, therefore, be determined with reference to the appended claims, along with the fill scope of equivalents to which such claims are entitled.

What is claimed is:

1. A machine-vision head for measuring a three-dimensional geometry of a device having a surface to be measured, comprising:
   a projector, the projector including:
      a first light source having a projection optical axis that intersects the device;
      a projection-imaging element positioned along the projection optical axis and spaced from the first light source; and
      a projection-pattern element positioned between the first light source and the projection imaging element along the projection optical axis, the projection-pattern element having a repeating sine-wave light-modulation pattern as measured along a line on the projection-pattern element; and
   an imager, the imager having a reception optical axis that intersects the device substantially at the projection optical axis, wherein the projection-pattern element light-modulation pattern includes a repeating pattern of grid lines having substantially constant density along lines in a direction parallel to the grid lines and a sine-wave density along lines in a direction perpendicular to the grid lines, wherein the first light source includes a elongated incandescent filament having a dimension along a longitudinal axis substantially longer than a width, wherein the longitudinal axis of the filament is substantially perpendicular to the projection optical axis and substantially parallel to the grid lines of the projection-pattern element; and a projection mask having an elongated aperture having a dimension along a length axis substantially longer than a dimension along a width axis perpendicular to the length axis, and wherein the length axis is substantially parallel to the grid lines of the projection-pattern element, wherein the projection mask limits the projected light to less than about three sine-wave cycles of the sine-wave pattern.

2. The machine-vision head according to claim 1, further comprising a light-intensity controller, coupled to receive intensity information regarding light output from the first light source, that outputs a control signal based on a measured intensity of light from the first light source.

3. The machine-vision head according to claim 2, wherein the control signal is operatively coupled to the first light source to control light output based on the measured light intensity in a feedback manner.

4. The machine-vision head according to claim 1, further comprising a condensing imaging element positioned between the first light source and the projection-pattern element along the projection optical axis.

5. The machine-vision head according to claim 1, further comprising a focussing reflector that substantially focusses an image of the first light source adjacent to the first light source.

6. The machine-vision head according to claim 5, wherein the reception optical axis is oriented to be at substantially a right angle to a direction of scanning, and the projection optical axis is oriented to be at substantially a forty-five-degree angle to the direction of scanning.

7. The machine-vision head according to claim 6, wherein a major plane of the projection-imaging element is oriented substantially perpendicular to the projection optical axis and a major plane of the projection-pattern element is oriented substantially perpendicular to the projection optical axis.

8. The machine-vision head according to claim 1, further comprising a second light source that directs substantially unpatterned light onto the device, the second light source being activated to allow the imager to obtain two-dimensional intensity data about the device.

9. A machine-vision head for measuring a three-dimensional geometry of a device having a surface to be measured, comprising:
   a projector, the projector including:
      a first light source having a projection optical axis that intersects the device;
      a projection-imaging element positioned along the projection optical axis and spaced from the first light source; and
      a projection-pattern element positioned between the first light source and the projection imaging element along the projection optical axis, the projection-pattern element having a repeating sine-wave light-modulation pattern as measured along a line on the projection-pattern element; and
   an imager, the imager having a reception optical axis that intersects the device substantially at the projection optical axis, wherein the projection-pattern element light-modulation pattern includes a repeating pattern of grid lines having substantially constant density along lines in a direction parallel to the grid lines and a sine-wave density along lines in a direction perpendicular to the grid lines, wherein the first light source includes a elongated incandescent filament having a dimension along a longitudinal axis substantially longer than a width, wherein the longitudinal axis of the filament is substantially perpendicular to the projection optical axis and substantially parallel to the grid lines of the projection-pattern element; and
   a projection mask having an elongated aperture having a dimension along a length axis substantially longer than a dimension along a width axis perpendicular to the length axis, and wherein the length axis is substantially parallel to the grid lines of the projection-pattern element; and
   a projection-mask actuator operable to adjust a position of the projection mask.

10. A machine-vision head for measuring a three-dimensional geometry of a device having a surface to be measured, comprising:
    a projector, the projector including:
       a first light source having a projection optical axis that intersects the device;
       a projection-imaging element positioned along the projection optical axis and spaced from the first light source, and
       a projection-pattern element positioned between the first light source and the projection imaging element along the projection optical axis, the projection-pattern element having a repeating sine-wave light-modulation pattern as measured along a line on the projection-pattern element;
    an imager, the imager having a reception optical axis that intersects the device substantially at the projection optical axis; and
    a light-intensity controller, coupled to receive intensity information regarding light output from the first light source, that outputs a control signal based on a measured intensity of light from the first light source, wherein the control signal is operatively coupled to the imager to control an amount of light received in an imaging cycle of the imager.

11. A machine-vision system for inspecting a device, comprising:
    an inspection station, the inspection station including:
       a projector, the projector including:
          a first light source having a projection optical axis that intersects the device;
          a projection-imaging element positioned along the projection optical axis and spaced from the first light source; and
          a projection-pattern element positioned between the first light source and the projection imaging element along the projection optical axis, the projection-pattern element having a repeating sine-wave light-modulation pattern as measured along a line on the projection-pattern element; and
       an imager, the imager having a reception optical axis that intersects the device when the inspection station is in operation, the imager maintained in a substantially fixed relationship to the pattern projector, the imager including at least three lines of semiconductor imaging pixels;
    a scanner mechanism that moves the imager relative to the device such that different portions of the device are successively imaged by the imager, wherein the first light source is activated in conjunction with the imager to obtain three-dimensional device geometry data regarding the device;
    a comparator coupled to the imager, the comparator comparing one or more characteristics of the acquired three-dimensional device geometry data with an intended predetermined geometry to produce a signal indicative of any device geometry departure of an actual device geometry from the intended predetermined geometry; and a projection mask having an elongated aperture having a dimension along a length axis substantially longer than a dimension along a width axis perpendicular to the length axis, wherein the length axis is substantially parallel to the grid lines of the projection-pattern element, and wherein the projection mask limits the projected light to less than about three sine-wave cycles of the sine-wave pattern.

12. The system according to claim 11, wherein the projection-pattern element light-modulation pattern includes a repeating pattern of grid lines having substantially constant density along lines in a direction parallel to the grid lines and a sine-wave density along lines in a direction perpendicular to the grid lines.

13. The system according to claim 12, wherein the first light source includes a elongated incandescent filament having a dimension along a longitudinal axis substantially longer than a width, wherein the longitudinal axis of the filament is substantially perpendicular to the projection optical axis and substantially parallel to the grid lines of the projection-pattern element.

14. The system according to claim 11, further comprising a light-intensity controller, coupled to receive intensity information regarding light output from the light source, that outputs a control signal based on a measured intensity of light from the light source, wherein the control signal is operatively coupled to the imager to control an amount of light received in an imaging cycle of the imager.

15. The system according to claim 11, further comprising a focussing reflector that substantially focusses an image of the light source adjacent to the light source.

16. The system according to claim 11, further comprising a condensing imaging element positioned between the first light source and the projection-pattern element along the projection optical axis.

17. The system according to claim 11, wherein a major plane of the projection-imaging element is oriented substantially perpendicular to the projection optical axis and a major plane of the projection-pattern element is oriented substantially perpendicular to the projection optical axis.

18. The system according to claim 11, further comprising a second light source that directs substantially unpatterned light onto the device, the second light source being activated in conjunction with the imager to obtain two-dimensional intensity data about the device from the imager.

19. A method for measuring a three-dimensional geometry of a device having a surface to be measured, comprising:
   projecting patterned light having a spatial-modulation pattern; the projecting pattern light including:
   projecting substantially unpatterned light;
   spatially modulating the unpatterened light with a sine-wave spatial modulation pattern to produce spatial-modulation patterned light; and
   imaging the spatial-modulation patterned light onto the device;
   scanning the device with the spatial-modulation patterned light;
   receiving reflected light from the device into at least three linear imager regions, wherein the spatially modulating includes modulating with a repeating pattern of grid lines having substantially constant density along lines in a direction parallel to the grid lines and a sine-wave density along lines in a direction perpendicular to the grid lines; and
   projection masking to an elongated aperture having a length axis substantially greater that a width axis, and wherein the length axis is substantially parallel to the grid lines of the pattern wherein the projection masking limits the projected light to less than about three sine-wave cycles of the sine-wave pattern.

20. The method according to claim 19, wherein the projecting substantially unpatterned light source includes a elongated light beam, wherein a longitudinal axis of the beam is perpendicular to the direction of projection and parallel to the grid lines.

21. The method according to claim 19, further comprising a adjusting a position of the projection masking.

22. The method according to claim 19, further comprising generating a light-intensity control signal based on intensity information regarding the projected light.

23. The method according to claim 19, further comprising controlling a light source to control light output based on the measured light intensity in a feedback manner.

24. The method according to claim 22, further comprising controlling an imager to control an amount of light received in an imaging cycle of the imager.

25. The method according to claim 19, further comprising condensing light onto the projection-pattern along the projection optical axis.

26. The method according to claim 19, further comprising reflectively focussing to substantially focus an image of the light source adjacent to the light source.

27. The method according to claim 19, wherein the reception optical axis is oriented to be at substantially a right angle to a direction of scanning, and the projection optical axis is oriented to be at substantially a forty-five-degree angle to the direction of scanning.

28. A computer-readable medium having computer-executable instructions thereon to cause a suitably configured information-handling system to perform a method comprising:
   projecting patterned light having a spatial-modulation pattern; the projecting pattern light including:
   projecting substantially unpatterned light;
   spatially modulating the unpatterened light with a sine-wave spatial modulation pattern to produce spatial-modulation patterned light; and
   imaging the spatial-modulation patterned light onto the device;
   scanning the device within the spatial-modulation patterned light;
   receiving reflected light from the device into at least three linear imager regions, wherein the spatially modulating includes modulating with a repeating pattern of grid lines having substantially constant density along lines in a direction parallel to the grid lines and a sine-wave density along lines in a direction perpendicular to the grid lines; and
   projection masking to an elongated aperture having a length axis substantially greater that a width axis, and wherein the length axis is substantially parallel to the grid lines of the pattern wherein the projection masking limits the projected light to less than about three sine-wave cycles of the sine-wave pattern.

29. The medium of claim 28, further comprising instructions that cause the method to further include adjusting a position of the projection masking.

30. The medium of claim 28, further comprising instructions that cause the method to further include generating a light-intensity control signal based on intensity information regarding the projected light.

31. The medium of claim 28, further comprising instructions that cause the method to further include controlling a light source to control light output based on the measured light intensity in a feedback manner.

32. The medium of claim 28, further comprising instructions that cause the method to further include controlling an imager to control an amount of light received in an imaging cycle of the imager.

33. The medium of claim 28, further comprising instructions that cause the method further include controlling an imager to control an amount of light received in an imaging cycle of the imager.

* * * * *

UNITED STATES PATENT AND TRADEMARK OFFICE
CERTIFICATE OF CORRECTION

PATENT NO. : 6,956,963 B2
DATED : October 18, 2005
INVENTOR(S) : Franz W. Ulrich et al.

It is certified that error appears in the above-identified patent and that said Letters Patent is hereby corrected as shown below:

Column 12,
Line 9, delete "form" and insert -- from --.
Lines 11 and 31, delete "a" and insert -- an --.

Column 19,
Line 19, delete "that" and insert -- than --.

Column 24,
Line 4, delete "that" and insert -- than --.

Column 25,
Line 58, insert -- . -- after "data".

Column 34,
Line 11, delete "that" and insert -- than --.

Column 44,
Line 49, delete "a" and insert -- an --.

Column 46,
Line 18, delete "a" and insert -- an --.

Column 47,
Line 3, delete "pattern" and insert -- patterned --.
Line 19, delete "a" and insert -- an --.
Line 26, delete "that" and insert -- than --.

Column 48,
Line 32, delete "a" and insert -- an --.

Column 50,
Line 17, delete "includes a elongated" and insert -- includes an elongated --.

UNITED STATES PATENT AND TRADEMARK OFFICE
CERTIFICATE OF CORRECTION

PATENT NO.   : 6,956,963 B2
DATED        : October 18, 2005
INVENTOR(S)  : Franz W. Ulrich et al.

It is certified that error appears in the above-identified patent and that said Letters Patent is hereby corrected as shown below:

Column 51,
Line 2, delete "pattern" and insert -- patterned --.
Line 18, delete "a" and insert -- an --.
Line 25, delete "that" and insert -- than --.

Column 74,
Line 62, delete "a" and insert -- an --.

Column 75,
Line 64, delete "a" and insert -- an --.

Column 77,
Line 18, delete "a" and insert -- an --.

Column 78,
Lines 2 and 56, delete "that" and insert -- than --.
Line 8, delete "a" and insert -- an --.
Line 49, delete "pattern" and insert -- patterned --.

Column 80,
Line 6, insert -- to -- after "method".

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,956,963 B2
DATED : October 18, 2005
INVENTOR(S) : Franz W. Ulrich et al.

It is certified that error appears in the above-identified patent and that said Letters Patent is hereby corrected as shown below:

Column 12,
Line 9, delete "form" and insert -- from --.
Lines 11 and 31, delete "a" and insert -- an --.

Column 19,
Line 19, delete "that" and insert -- than --.

Column 24,
Line 4, delete "that" and insert -- than --.

Column 25,
Line 58, insert -- . -- after "data".

Column 34,
Line 11, delete "that" and insert -- than --.

Column 44,
Line 49, delete "a" and insert -- an --.

Column 46,
Line 18, delete "a" and insert -- an --.

Column 47,
Line 3, delete "pattern" and insert -- patterned --.
Line 19, delete "a" and insert -- an --.
Line 26, delete "that" and insert -- than --.

Column 48,
Line 32, delete "a" and insert -- an --.

Column 50,
Line 17, delete "includes a elongated" and insert -- includes an elongated --.

Column 51,
Line 2, delete "pattern" and insert -- patterned --.
Line 18, delete "a" and insert -- an --.
Line 25, delete "that" and insert -- than --.

Column 74,
Line 62, delete "a" and insert -- an --.

UNITED STATES PATENT AND TRADEMARK OFFICE
CERTIFICATE OF CORRECTION

PATENT NO. : 6,956,963 B2
DATED : October 18, 2005
INVENTOR(S) : Franz W. Ulrich et al.

It is certified that error appears in the above-identified patent and that said Letters Patent is hereby corrected as shown below:

<u>Column 75,</u>
Line 64, delete "a" and insert -- an --.

<u>Column 77,</u>
Line 18, delete "a" and insert -- an --.

<u>Column 78,</u>
Lines 2 and 56, delete "that" and insert -- than --.
Line 8, delete "a" and insert -- an --.
Line 49, delete "pattern" and insert -- patterned --.

<u>Column 80,</u>
Line 6, insert -- to -- after "method".

Signed and Sealed this

Twenty-first Day of March, 2006

JON W. DUDAS
*Director of the United States Patent and Trademark Office*